US011279829B2

(12) United States Patent
Koenemann et al.

(10) Patent No.: US 11,279,829 B2
(45) Date of Patent: Mar. 22, 2022

(54) 1,6,7,12-TETRA-(2-ISOPROPYLPHENOXY)-SUBSTITUTED PERYLENE TETRACARBOXYLIC ACID DIIMIDES AS COLOR CONVERTERS

(71) Applicant: BASF SE, Ludwigshafen am Rhein (DE)

(72) Inventors: Martin Koenemann, Ludwigshafen (DE); Gerhard Wagenblast, Wachenheim (DE); Hannah Stephanie Mangold, Ludwigshafen (DE); Sorin Ivanovici, Ludwigshafen (DE)

(73) Assignee: BASF SE ( * ) Notice: Subject to any disclaimer, the term of this patent is extended or adjusted under 35 U.S.C. 154(b) by 33 days.

(21) Appl. No.: 16/477,750

(22) PCT Filed: Jan. 17, 2018

(86) PCT No.: PCT/EP2018/051123
§ 371 (c)(1),
(2) Date: Jul. 12, 2019

(87) PCT Pub. No.: WO2018/134263
PCT Pub. Date: Jul. 26, 2018

(65) Prior Publication Data
US 2019/0359829 A1 Nov. 28, 2019

(30) Foreign Application Priority Data

Jan. 18, 2017 (EP) .................................... 17151931
Aug. 24, 2017 (EP) .................................... 17187765

(51) Int. Cl.
C09B 5/62 (2006.01)
F21V 9/32 (2018.01)
(Continued)

(52) U.S. Cl.
CPC ............... C09B 5/62 (2013.01); C09D 11/03 (2013.01); C09D 11/328 (2013.01); C09D 11/50 (2013.01);
(Continued)

(58) Field of Classification Search
CPC ............... C09B 5/62; C09D 11/00–54; C09K 2211/00–1096; C07D 471/06; B41M 3/14–148
See application file for complete search history.

(56) References Cited

U.S. PATENT DOCUMENTS 2,551,731 A 5/1951 Gordon et al.
3,357,985 A 12/1967 Fuchs et al.
(Continued)

FOREIGN PATENT DOCUMENTS

EP 3 072 887 A1 9/2016
JP 11144870 A * 5/1999
(Continued)

OTHER PUBLICATIONS

Definition of "quantum dot" [retrieved from https://www.merriam-webster.com/dictionary/quantum%20dot on Oct. 7, 2020] (Year: 2020).*
(Continued)

Primary Examiner — Eric R Smith
(74) Attorney, Agent, or Firm — Faegre Drinker Biddle & Reath LLP

(57) ABSTRACT

The present invention relates to 1,6,7,12-tetra-(2-isopropylphenoxy)-substituted perylene tetracarboxylic acid diimides of the formula (I) wherein $R^1$ and $R^2$ independently of each other are selected from hydrogen, $C_1$-$C_{24}$-alkyl, $C_1$-$C_{24}$-haloalkyl, $C_3$-$C_{24}$-cycloalkyl, $C_6$-$C_{24}$-aryl and $C_6$-$C_{24}$-aryl-$C_1$-$C_{10}$-alkylene, where the rings of cydoalkyi, aryl, and aryl-alkylene in the three last-mentioned radicals are unsubstituted or substituted as defined in the claims and in the description. Moreover, the present invention relates to the use of said perylene compounds, in particular to the use of said perylene compound(s) in color converters, for data transmission and in security inks for security printing. The present invention also relates to the use of said color converters, to their use in lighting devices, to lighting devices comprising at least one LED and at least said color converter and to a device producing electric power upon illumination comprising a photovoltaic cell and said color converter.

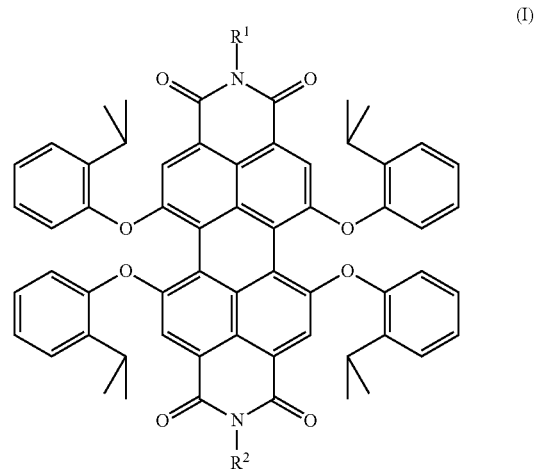

18 Claims, No Drawings

(51) Int. Cl.

| | | |
|---|---|---|
| *C09D 11/03* | (2014.01) | |
| *C09D 11/328* | (2014.01) | |
| *C09D 11/50* | (2014.01) | |
| *C09K 11/06* | (2006.01) | |
| *H01L 31/0232* | (2014.01) | |
| *H01L 51/00* | (2006.01) | |
| *H01L 51/42* | (2006.01) | |
| *H01L 51/50* | (2006.01) | |
| *H01L 31/055* | (2014.01) | |
| *F21Y 115/10* | (2016.01) | |
| *H01L 33/32* | (2010.01) | |

(52) U.S. Cl.
CPC ............... *C09K 11/06* (2013.01); *F21V 9/32* (2018.02); *H01L 31/02322* (2013.01); *H01L 31/055* (2013.01); *H01L 51/0064* (2013.01); *H01L 51/42* (2013.01); *H01L 51/50* (2013.01); *C09K 2211/1007* (2013.01); *C09K 2211/1014* (2013.01); *C09K 2211/1018* (2013.01); *F21Y 2115/10* (2016.08); *H01L 33/32* (2013.01)

(56) References Cited

U.S. PATENT DOCUMENTS

| | | | |
|---|---|---|---|
| 4,845,223 | A | 7/1989 | Seybold et al. |
| 5,470,502 | A | 11/1995 | Hahn et al. |
| 6,472,050 | B1 | 10/2002 | Buoni |
| 8,071,775 | B2 | 12/2011 | Konemann et al. |
| 9,236,535 | B2 | 1/2016 | Wagenblast et al. |
| 9,406,848 | B2 | 8/2016 | Konemann et al. |
| 9,711,665 | B2 | 7/2017 | Wagenblast et al. |
| 9,790,423 | B2 | 10/2017 | Konemann et al. |
| 9,919,999 | B2 | 3/2018 | Konemann et al. |
| 10,230,023 | B2 | 3/2019 | Konemann et al. |
| 2008/0167467 | A1 | 7/2008 | Konemann et al. |
| 2011/0253198 | A1* | 10/2011 | Patrick ................. H01L 31/055 136/247 |
| 2011/0282020 | A1 | 11/2011 | Sipos |
| 2011/0306804 | A1 | 12/2011 | Cortright |
| 2014/0076397 | A1 | 3/2014 | Wagenblast et al. |
| 2014/0336349 | A1 | 11/2014 | Sipos et al. |
| 2017/0183295 | A1* | 6/2017 | Koenemann .......... C07C 255/52 |
| 2018/0062766 | A1* | 3/2018 | Ooi ....................... H04B 10/564 |

FOREIGN PATENT DOCUMENTS

| | | | |
|---|---|---|---|
| WO | WO 2004/029028 | A2 | 4/2004 |
| WO | WO 2007/006717 | A1 | 1/2007 |
| WO | WO 2009/037283 | A1 | 3/2009 |
| WO | WO 2010/132740 | A2 | 11/2010 |
| WO | WO 2011/043660 | A2 | 4/2011 |
| WO | WO 2011/043661 | A1 | 4/2011 |
| WO | WO 2012/042438 | A1 | 4/2012 |
| WO | WO 2012/152812 | A1 | 11/2012 |
| WO | WO 2012/168395 | A1 | 12/2012 |
| WO | WO 2014/122549 | A1 | 8/2014 |
| WO | WO 2014/131628 | A1 | 9/2014 |
| WO | WO 2015/019270 | A1 | 2/2015 |
| WO | WO 2015/062916 | A1 | 5/2015 |
| WO | WO 2015/137804 | A1 | 9/2015 |
| WO | WO 2015/169935 | A1 | 11/2015 |
| WO | WO 2016/151068 | A1 | 9/2016 |
| WO | WO 2017/121833 | A1 | 7/2017 |
| WO | WO 2018/065502 | A1 | 4/2018 |

OTHER PUBLICATIONS

Machine translation of JP11-144870A (Year: 1999).*
International Search Report dated Feb. 20, 2018 in PCT/EP2018/051123, 4 pages.
U.S. Appl. No. 16/339,653, filed Apr. 4, 2019, Martin Konemann, et al.
U.S. Appl. No. 16/069,954, filed Jul. 13, 2018, US 2019-0023905, Martin Konemann, et al.
U.S. Appl. No. 16/478,380, filed Jul. 16, 2019, Martin Konemann, et al.

* cited by examiner

1,6,7,12-TETRA-(2-ISOPROPYLPHENOXY)-SUBSTITUTED PERYLENE TETRACARBOXYLIC ACID DIIMIDES AS COLOR CONVERTERS

The present invention relates to 1,6,7,12-tetra-(2-isopropyl phenoxy)-substituted perylene tetracarboxylic acid diimides and to their use. In particular, the present invention relates to the use of said perylene compound(s) in color converters, for data transmission and in security inks for security printing. The present invention also relates to the use of said color converters, to their use in lighting devices, to lighting devices comprising at least one LED and at least said color converter and to a device producing electric power upon illumination comprising a photovoltaic cell and said color converter.

BACKGROUND OF THE INVENTION

Nowadays, light emitting diodes (LEDs) are replacing existing lighting sources such as incandescent lamps and fluorescent lamps to an ever increasing extent. LEDs offer several advantages such as low power consumption, low cost, high luminance efficiency, ease in color rendering, and long lifetime. Efficient LEDs are often based on blue light emitting materials. To produce a LED illumination device that creates a desired color output, for example a white color output, a suitable color converter, which generally comprises at least one polymer layer and one or more wavelength converting material(s), is used which converts some or all of the LED's output into longer wavelengths.

There are different methods to produce white light from LEDs sources. According to one method, the wavelength converting material (also known as (a) phosphor(s)) may be applied directly on the LED die. This method is also referred to as "phosphor on chip". In phosphor on chip LEDs, the phosphor is generally an inorganic one due to its high thermal and radiative stability. According to this method, a light source that appears to be white to a human observer can be constructed from a blue LED covered with a phosphor such as cerium-doped yttrium aluminium garnet (Ce:YAG). Ce:YAG absorbs part of the blue LED emission and re-emits a yellow spectrum. If the ratio of blue to yellow light is chosen correctly, the resultant light source appears white to the human observer. LED-based sources that generate white light should also have a good color-rendering index (CRI). The CRI is widely used to measure how accurately a lighting source renders the color of objects. Illumination devices according to the phosphor on chip concept generate cool white light having a correlated color temperature CCT of greater than 6 000 K and their average color rendering index (CRI) is often low, usually about 70 to 85. Therefore, the light of a standard Ce:YAG-based white LED is often seen as unattractive since generation of warm-white light is not possible with that configuration (without adding a red light emitting phosphor). To create a pleasant white light output, it is necessary to use a combination of green/yellow phosphor and red phosphor. However, inorganic phosphors have many disadvantages, e.g. they are relatively expensive and environmentally unfriendly. Furthermore, their quantum efficiency is often unsatisfactory.

To provide a more pleasing and natural white light having a CCT below 6 000 K, another method may be used. According to this method, the color converter comprising the phosphor dissolved or dispersed in a polymeric matrix is at a certain distance from the blue LED chip. This concept is referred to as "remote phosphor" concept. LEDs according to the "remote phosphor" concept are more energy-efficient than those according to the "phosphor on chip" concept. The spatial distance reduces the stress resulting from heat and radiation to such an extent that the requirements on the stability can be achieved by many organic phosphors. The organic phosphor may be a single organic phosphor or a mixture of different organic phosphors to broaden the spectrum. For CCT of less than 6000 K, e.g. in the range of 2700 to 5000 K, with a CRI of 80 or higher, most blue LED illumination devices with remote phosphor configuration comprise a mixture of an organic phosphor emitting in the yellow-green spectral range and an organic phosphor emitting in the red spectral range. The composition/hue of the light can be precisely adjusted by applying optimized amounts of organic phosphors. Thus, the resulting light has a richer and broader wavelength spectrum and produces a higher color-quality light.

White light illumination devices with a correlated color temperature (CCT) of less than 6 000 K may also be constructed from a phosphor-on chip LED made of a blue light emitting LED and an inorganic yellow phosphor such as cerium-doped yttrium aluminium garnet in combination with a color converter comprising at least one organic phosphor, often a combination of an organic phosphor emitting in the yellow-green spectral range and an organic phosphor emitting in the red spectral range, where the phosphor-on chip LED and the color converter are in a spatial distance (remote phosphor arrangement). High CRI values of 80 and above may be achieved for mixtures of organic phosphor(s) with the emission in the yellow-green to red spectral range.

In general, organic phosphors exhibit much higher absorptivity compared to inorganic phosphors, which means that considerably less material is required for efficient wavelength conversion than in the case of inorganic phosphors. In addition, organic phosphors are available at low cost. No expensive materials such as rare-earth metals are needed.

Nowadays, there is also a great need for phosphors for color converters, which can combine illumination with data transmission. A new technology, which utilizes white LEDs for both illumination and data transmission, is known as visible-light communication (VLC). VLC is a rapid growing technological field that aims to implement fast and safe wireless communication to replace or complement existing wireless technologies. Organic phosphor that can be used inter alia as color converters in remote phosphor LEDs offer many potential advantages for VLC due to their visible band gaps, short radiative lifetime, and high fluorescence quantum yield. LiFi (Light Fidelity) is the term established for the transmission of data through illumination using LED lighting that varies in its intensity for high speed wireless communication. Together with the widespread use of LED lighting in offices, streetlights and homes, LiFi is an added benefit to the existing lighting infrastructure.

A special field of application for some organic phosphors regards inks for printing processes which are used for printing currency and other security documents, also referred to as "security printing".

U.S. Pat. No. 4,845,223 describe aryloxy-substituted perylene-3,4,9,10-tetracarboxylic acid diimides and their use for concentrating light.

WO 2007/006717 describes aryloxy-substituted rylene derivatives.

WO 2012/042438 describes color converters comprising perylene tetracarboxylic acid diimides in a polymeric material comprising a polyester having an aromatic moiety incorporated in the polymer backbone. The perylene tetracarboxylic acid diimides carry up to four substituents at the bay-positions of the perylene core, the substituents being selected from fluorine, methoxy, unsubstituted $C_1$-$C_{16}$-alkyl and phenoxy which is optionally substituted by fluorine, methoxy or $C_1$-$C_{16}$-alkyl.

WO 2017/121833 describes perylene bisimides with rigid 2,2'-biphenoxy bridges in the bay positions (1-,6-,7-,12-positions) that are useful as fluorescent dye in a color converter or can also be used in security inks for security printing.

Unpublished EP 16192617.5 (unpublished PCT/EP2017/075274) describes perylene bisimides carrying in each bay position (1-,6-,7-,12-positions) of the conjugated perylene core a 2-phenylphenoxy substituent and their use, especially in color converters, and in security inks for security printing.

None of these documents concretely describes perylene bisimide compounds carrying a 2-diisopropylphenoxy substituent in each by position (1-, 6-, 7-, 12-positon) of the perylene skeleton.

The present application claims priority of unpublished EP 17151931. Unpublished EP 17151931.7 describes fluorescent colorants based on cyanoaryl-substituted naphthoylenebenzimidazole compounds. This reference also describes color converters comprising a mixture of a yellow colorant, an orange colorant and a red colorant, where the red colorant is i.a. N,N'-bis(2,6-diisopropylphenyl)-1,6,7,12-tetra-(2-isoproyl)phenoxyperylene-3,4;9,10-tetracarboxylic acid diimide.

Nowadays, there is a great demand for white LEDs with low correlated color temperatures, preferably in the range from 2700 to 5000 K, and good color reproduction, in particular the CRI should be at least 85, preferably 90, and at the same time for high efficiency and stability. These objects may be achieved by combining a blue LED or white LED with an organic phosphor emitting in the yellow/green spectral range and an organic phosphor emitting in the red spectral range. Although a great variety of organic red phosphors have been available, they often exhibit unsufficient fluorescence quantum yields and/or unsufficient stabilities under LED irradiation conditions and/or are sensitive to moisture and oxygen.

Therefore, there is a great demand in organic phosphors emitting in the orange/red spectal range having high quantum yields in polymers and excellent stabilities under the practical application conditions. Further, it should at the same time be possible to provide a LED lighting device having a good color reproduction and color temperature. Preferably the LED lighting device should have a CCT below 6 000 K and an average color rendering index CRI of greater than 85.

There is also a great demand in phosphors for data transmission that have fluorescent lifetimes in the order of a few nanoseconds and preferably even lower while maintaining good emission efficiency. Further, it should at the same time be possible to provide a lighting device having a good color reproduction and color temperature.

There is also a great demand in compounds suitable for security printing.

Some of the organic phosphors known from prior art, with a view to their stability, are unsatisfactory or have other disadvantage such as low fluorescence quantum yields or too long fluorescence lifetimes which restricts modulation frequency and hence the transmission rate in LiFi applications. It is therefore an object of the present invention to provide organic phosphors, especially for use in color converters, which overcome the above-mentioned disadvantages and which exhibit high color reproduction, when used in combination with further phosphors. Alternatively or additionally, it is an object of the present invention to provide organic phosphors for use in color converters for LiFi applications. Alternatively or additionally, it is an object of the present invention to provide compounds that meet the technical stability requirements (chemical stability, heat stability and/or light stability) for security printing.

Preferably, the organic phosphors should feature one or more of the following characteristics:
- high fluorescence quantum yield (QY);
- short fluorescent lifetimes in the order of a few nanoseconds;
- long lifetime;
- high light stability under blue and/or white light irradiation conditions;
- high heat stability under blue and/or white light irradiation conditions;
- high chemical stability with respect to moisture and oxygen;
- high chemical stability, in particular fastness to bleaching with hypochlorite and fastness to solvents (like toluene, acetone or dichloromethane;
- high chemical stability to boiling water;
- high compatibility with a multiplicity of formulations, in particular printing ink formulations used in security printing and thermoplastic polymer formulations used for laser-welding.

It has been found that, surprisingly, the compounds of formula (I) described hereinafter achieve these objects and therefore are advantageously suitable for use in color converters for creating white light with low correlated color temperatures in the range from 2700 to 6000 K and good color reproduction; in converters for data transmission in light fidelity applications; and in security inks for security printing.

SUMMARY OF THE INVENTION

Hence, in a first aspect, the invention provides a novel perylene bisimide compound of the formula (I)

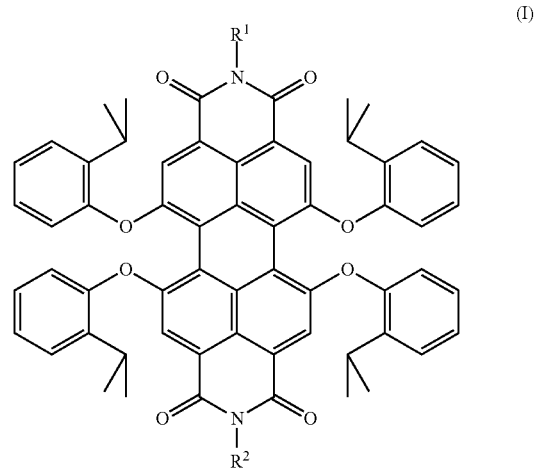

wherein
$R^1$ and $R^2$ independently of each other are selected from the group consisting of hydrogen, $C_1$-$C_{24}$-alkyl, $C_1$-$C_{24}$-haloalkyl, $C_3$-$C_{24}$-cycloalkyl, $C_6$-$C_{24}$-aryl and $C_6$-$C_{24}$-aryl-$C_1$-$C_{10}$-alkylene, where the rings of cycloalkyl, aryl, and aryl-alkylene in the three last-mentioned radicals are unsubstituted or substituted with 1, 2, 3, 4 or 5 identical or different radicals $R^a$, and where $C_1$-$C_{24}$-alkyl, $C_1$-$C_{24}$-haloalkyl and the alkylene moiety of $C_6$-$C_{24}$-aryl-$C_1$-$C_{10}$-alkylene may be interrupted by one or more heteroatoms or heteroatomic groups selected from O, S and $NR^b$; where $R^a$ is $C_1$-$C_{24}$-alkyl, $C_1$-$C_{24}$-fluoroalkyl, $C_1$-$C_{24}$-alkoxy, fluorine, chlorine or bromine; and $R^b$ is hydrogen, $C_1$-$C_{20}$-alkyl, $C_3$-$C_{24}$-cycloalkyl, heterocycloalkyl, hetaryl or $C_6$-$C_{24}$-aryl.

The compounds of formula (I) are distinguished by their high stability, especially chemical and photochemical stability, and very short fluorescence decay times.

A further aspect of the invention relates to a color converter comprising at least one polymer as a matrix and at least one perylene bisimide compound of formula (I) as defined above as a fluorescent colorant, wherein the at least one polymer consists essentially of polystyrene, polycarbonate, polyacrylate, polymethylmethacrylate, polymethacrylate, polyvinylpyrrolidone, polyvinyl acetate, polyvinyl chloride, polybutene, silicone, epoxy resin, polyvinyl alcohol, poly(ethylene vinylalcohol)-coplymer, polyacrylonitrile, polyvinylidene chloride, polystyrene acrylonitrile, polybutylene terephthalate, polyethylene terephthalate, a 2,5-furandicarboxylate polyester, polyvinyl butyrate, polyvinyl chloride, polyamides, polyoxymethylenes, polyimides, polyetherimides or mixtures thereof.

A further aspect of the invention relates to the use of a color converter as defined above for conversion of light generated by a blue LED with a center wavelength of emission between 400 nm and 480 nm to provide white light or for conversion of light generated by a cool white LED having a correlated color temperature between 3 000 K and 20 000 K, especially 4 000 and 20 000 K, to provide white light having a lower correlated color temperature.

Still a further aspect of the invention relates to the use of a color converter as defined above in displays.

A further aspect of the invention relates to a lighting device comprising
(i) at least one LED selected from a blue LED with a center wavelength of emission from 400 nm to 480 nm and a cool white LED having a correlated color temperature between 3 000 K and 20 000 K, especially 4 000 and 20 000 K; and
(ii) at least one color converter as defined above, wherein the at least one color converter is in a remote arrangement from the at least one LED.

A further aspect of the invention relates to a device producing electric power upon illumination comprising a photovoltaic cell and the color converter as defined above, where at least a part of the light not absorbed by the photovoltaic cell is absorbed by the color converter.

A further aspect of the invention relates to use of a perylene bisimide compound of the formula (I) as defined above in color converters for converting light emitted from a blue LED with a center wavelength of emission between 400 nm and 480 nm into light of a second, longer wavelength or for converting light emitted from a cool-white LED having a correlated color temperature between 3 000 K and 20 000 K, especially 4 000 and 20 000 K, to provide white light having a lower correlated color temperature, for coloring coatings, printing inks and plastics, producing aqueous polymer dispersions which absorb and/or emit electromagnetic radiation, for data storage, for data transmission, for optical labels, for security labels in documents and for brand protection or as a fluorescent label for biomolecules.

A further aspect of the invention relates to the use of a perylene bisimide compound of the formula (I) as defined herein in security inks for security printing.

A further aspect of the invention relates to a transmitter for transmitting data and for emitting electromagnetic radiation in the visible spectral range, said transmitter comprising:
a radiation source for generating and emitting first electromagnetic radiation and
a modulator being adapted to modulate the first electromagnetic radiation depending on the data to be transmitted generating modulated first electromagnetic radiation,
characterized in that the transmitter further comprises
a color converter as defined herein for converting at least a part of the modulated first electromagnetic radiation into modulated second electromagnetic radiation, said modulated second electromagnetic radiation being different from the modulated first electromagnetic radiation.

A further aspect of the invention relates to a printing ink formulation for security printing, comprising at least one compound of the formula (I) as defined herein.

DESCRIPTION OF THE INVENTION

In the context of the present invention, the term "luminescent material" is also referred to as phosphor(s) or colorant(s). The luminescent material may be inorganic solid(s) or organic fluorescent colorant(s).

In the context of the present invention, the terms organic "phosphor" and "colorant" are used interchangeably to describe an organic material which converts light of a first wavelength to light of a second wavelength.

Fluorescent colorants include all materials which are capable of absorbing light of a particular wavelength and converting it to light of another wavelength. Organic fluorescent colorants may be organic fluorescent pigments or organic fluorescent dyes. Preferably, they are organic fluorescent dyes.

The term "conversion material" refers to a material that is excited by a photon of a first wavelength and emits photons of a second, different wavelength.

A quantum dot is a nanocrystal made of semiconductor materials that is small enough to exhibit quantum mechanical properties. Quantum dots are showing remarkably narrow emission spectra, i.e. with extraordinary small FWHM (full width of half maximum). The color output of the dots can be tuned by controlling the size of the crystals. With a smaller size in quantum dots, the quantum dots emit light of a shorter wavelength.

In the context of the present invention, the term "color converter" is understood to mean all physical devices capable of absorbing light of particular wavelengths and converting it to light of a second wavelength. Color converters are, for example, part of lighting devices, especially those lighting devices which utilize UV light or LEDs or OLEDs as a light source, or of fluorescence conversion solar cells.

In the context of the present invention, the term "center wavelength" of a given spectral distribution $F(\lambda)$ is defined as the following average: $\lambda_c = \int \lambda \cdot F(\lambda) \, d\lambda / \int F(\lambda) \, d\lambda$.

In the context of the present invention, a "blue LED" is understood to mean an LED which emits light in the blue range of the electromagnetic spectrum with a center wavelength of emission in the range of 420 to 480 nm, preferably 440 to 470 nm, most preferably at 440 to 460 nm. Suitable semiconductor materials are silicon carbide, zinc selenide and nitrides such as aluminum nitride (AlN), gallium nitride (GaN), indium nitride (InN) and indium gallium nitride (InGaN). LEDs typically have a narrow wavelength distribution that is tightly centered about their peak wavelength. Standard InGaN-based blue LEDs are fabricated on a sapphire substrate and peak emission wavelength is usually centered at 445 to 455 nm.

In the context of the present invention, a "white LED" is understood to mean an LED illumination source that creates white color output. Examples are multi-LEDs (also called RGB LED system) consisting of a red, a green and a blue LED whose light emissions are mixed to form white light. Further examples are LEDs coated with a phosphor to convert a part of the light emitted from a blue or an ultraviolet LED to broad spectrum of white light.

An UV-LED is a light emitting diode emitting ultraviolet electromagnetic radiation, i. e. electromagnetic radiation having wavelengths below 400 nm.

In the context of the present invention, the term "white light" relates to light having a color correlation temperature (CCT) between 2 000 to 20 000 K, especially 2 500 to 20 000 K. A cool white LED commonly has a correlated color temperature of 4000 K or above, for example in the range of 4000 to 20000K.

In the context of the present invention, the term "blue light" relates to light having a wavelength in the range from 400 to 480 nm, especially 440 to 480 nm.

In the context of the present invention, an electromagnetic radiation comprising the visible spectral range is also designated as light.

LEDs are not blackbody or incandescent sources and thus have a correlated color temperature (CCT). CCT is the temperature of a blackbody radiator that is perceived by the human eye to emit the same white light as the LEDs. CCT describes the color appearance of white light emitted from electric light sources and is measured in Kelvin. It is determined according to the CIE international standard. CCT from a white light source usually is in the range from 1 500 K to 20 000 K, especially 2 000 K to 20 000 K. White light having higher CCT contains relatively higher intensity in the short wavelength region (blue) and relatively lower intensity in the longer wavelength region (red) compared to white light with lower CCT. Accordingly, higher CCTs generally indicate white light having a more significant blue component or a cool tone while lower CCTs generally indicate light having a more significant red tint or a warm tone. A white light having a CCT in the range from 4 500 K to 20 000 K is often referred to as cool white light, a white light having a CCT in the range from 2 700 K to 3 200 K is often referred to as warm-white light and a white light having a CCT in the range between 3 200 K to 4 500 K is often referred to as neutral white. Warmer color temperatures are especially suitable for living spaces.

Color rendering (CRI) is a measure how a light source makes the color of an object appear to the human eye and how well subtle variations in color shade are revealed. In general, CRI is considered to be a more important lighting quality than color temperature. According to CIE 17.4, International Lighting Vocabulary, color rendering (CRI) is defined as "the effect of an illuminant on the color appearance of objects by conscious or unconscious comparison with the color appearance under a reference illuminant". The average or general color rendering index Ra is calculated from the differences in the chromaticities of the eight pastel CIE standard (reference) color samples R1 to R8 (CIE 13.3-1995). Negative values are also possible. A reference source, such as black body radiation, is defined as having a CRI index (Ra) of 100 (which is the maximum), i.e. a value of 100 indicates that the source renders colors in a manner identical to the reference. The lower the CRI rating, the less accurately colors will be reproduced. For many general interior illumination applications, a CRI value (Ra) of greater than 80 is acceptable. For general lighting, the color rendering index should be above 85. In applications where accurate color rendering is required, a high CRI Ra of at least 90 is usually highly desirable, so that objects illuminated by the lighting source may appear to have more natural coloring to the human eye. CRI Ra does not include coefficients corresponding to six highly saturated colors (R9-R14). Of these, R9 corresponds to a strong red color, which may affect a red-green contrast that may be beneficial in rendering colors. Often, the ability to reproduce red colors well is essential for accurately rendering colors, as the color red is often found mixed into processed colors. Thus, if a light source cannot render red correctly, things that are reddish will turn dull. Accordingly, light sources with high CRI Ra and with positive R9 value tend to produce the most vivid colors.

According to the CIE 1931 standard colorimetric system, colors are perceived by human eye following specific color curves. The standard luminosity curve VA accounts for the wavelength dependence of the sensitivity of human eye. The luminosity curve has a maximum possible value of 683 lm/W, for the case of monochromatic light at a wavelength of 555 nm (green). Luminous flux is the measure of the perceived power of light.

The word "essentially" in the context of the present invention encompasses the words "completely", "wholly" and "all". The word encompasses a proportion of 90% or more, such as 95% or more, especially 99% or 100%.

The definitions of the variables specified in the above formulae use collective terms which are generally representative of the respective substituents. The definition $C_n$-$C_m$ gives the number of carbon atoms possible in each case in the respective substituent or substituent moiety The expression "halogen" denotes in each case fluorine, bromine, chlorine or iodine, particularly chlorine, bromide or iodine.

In the context of the invention, the expression "in each case unsubstituted or substituted alkyl, cycloalkyl and aryl" represents unsubstituted or substituted alkyl, unsubstituted or substituted cycloalkyl and unsubstituted or substituted aryl.

Likewise, in the context of the invention, the expression "in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkyloxy, $C_6$-$C_{24}$-aryl and $C_6$-$C_{24}$-aryloxy" represents 35 unsubstituted or substituted $C_1$-$C_{30}$-alkyl, unsubstituted or substituted polyalkyleneoxy, unsubstituted or substituted $C_1$-$C_{30}$-alkoxy, unsubstituted or substituted $C_1$-$C_{30}$-alkylthio, unsubstituted or substituted $C_3$-$C_{20}$-cycloalkyl, unsubstituted or substituted $C_3$-$C_{20}$-cycloalkyloxy, unsubstituted or substituted $C_6$-$C_{24}$-aryl and unsubstituted or substituted $C_6$-$C_{24}$-aryloxy.

For the purpose of the present invention, the term "aliphatic radical" refers to an acyclic saturated or unsaturated, straight-chain or branched hydrocarbon radical. Usually the aliphatic radical has 1 to 100 carbon atoms. Examples for an aliphatic radical are alkyl, alkenyl and alkynyl.

For the purpose of the present invention, the term "cycloaliphatic radical" refers to a cyclic, non-aromatic saturated or unsaturated hydrocarbon radical having usually 3 to 20 ring carbon atoms. Examples are cycloalkanes, cycloalkenes, and cycloalkynes. The cycloaliphatic radical may also comprise heteroatoms or heteroatom groups selected from N, O, S and $SO_2$.

The term "alkyl" as used herein and in the alkyl moieties of alkoxy, alkylthio, alkylsulfinyl, alkylsulfonyl, alkylamino, dialkylamino, alkylcarbonyl, alkoxycarbonyl and the like refers to saturated straight-chain or branched hydrocarbon radicals having usually 1 to 100 ("$C_1$-$C_{100}$-alkyl"), 1 to 30 ("$C_1$-$C_{30}$-alkyl"), 1 to 18 ("$C_1$-$C_{18}$-alkyl"), 1 to 12 ("$C_1$-$C_{12}$-alkyl"), 1 to 8 ("$C_1$-$C_8$-alkyl") or 1 to 6 ("$C_1$-$C_6$-alkyl") carbon atoms. Alkyl is preferably $C_1$-$C_{30}$-alkyl, more preferably $C_1$-$C_{20}$-alkyl. Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethylpentyl, n-octyl, 1-methylheptyl, 2-methylheptyl, 1-ethylhexyl, 2-ethylhexyl, 1-propylpentyl, 2-propylpentyl, n-nonyl, etc.

Substituted alkyl groups, depending on the length of the alkyl chain, have one or more (e.g. 1, 2, 3, 4, 5 or more than 5) substituents. These are preferably each independently of each other selected from unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —$COOR^{Ar1}$, $NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted alkyl groups have one or more, for example 1, 2 or 3 substituent(s) selected from unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

Special embodiments of substituted alkyl groups are alkyl groups, wherein one hydrogen atom has been replaced by an aryl radical ("aralkyl", also referred to hereinafter as aryl-alkyl or arylalkylene), in particular a phenyl radical. The aryl radical in turn may be unsubstituted or substituted, suitable substituents are the substituents mentioned below for aryl. Particular examples of aryl-$C_1$-$C_4$-alkyl include benzyl, 1-phenethyl, 2-phenetyl, 1-phenylpropyl, 2-phenylpropyl, 3-phenyl-1-propyl, 2-phenyl-2-propyl, naphthylmethyl, naphthylethyl, etc.

Further special embodiments of substituted alkyl groups are alkyl groups where some or all of the hydrogen atoms in these groups may be replaced by halogen atoms as mentioned above, for example $C_1$-$C_4$-haloalkyl.

The term "alkenyl" as used herein refers to straight-chain or branched hydrocarbon groups having usually 2 to 100 ("$C_2$-$C_{100}$-alkenyl"), 2 to 18 ("$C_2$-$C_{18}$-alkenyl"), 2 to 10 ("$C_2$-$C_{10}$-alkenyl"), 2 to 8 ("$C_2$-$C_8$-alkenyl"), or 2 to 6 ("$C_2$-$C_6$-alkenyl") carbon atoms and one or more, e.g. 2 or 3, double bonds in any position. Substituted alkenyl groups, depending on the length of the alkenyl chain, have one or more (e.g. 1, 2, 3, 4, 5 or more than 5) substituents. These are preferably each independently of each other selected from unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —$COOR^{Ar1}$, $NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted alkenyl groups have one or more, for example 1, 2 or 3 substituent(s) selected from unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

The term "alkynyl" as used herein (also referred to as alkyl whose carbon chain may comprise one or more triple bonds) refers to straight-chain or branched hydrocarbon groups having usually 2 to 100 ("$C_2$-$C_{100}$-alkynyl"), 2 to 18 ("$C_2$-$C_{18}$-alkynyl"), 2 to 10 ("$C_2$-$C_{10}$-alkynyl"), 2 to 8 ("$C_2$-$C_8$-alkynyl"), or 2 to 6 ("$C_2$-$C_6$-alkynyl") carbon atoms and one or more, e.g. 2 or 3, triple bonds in any position. Substituted alkynyl groups, depending on the length of the alkynyl chain, have one or more (e.g. 1, 2, 3, 4, 5 or more than 5) substituents. These are preferably each independently of each other selected from unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, alkylcarbonyloxy, formyl, acyl, COOH, carboxylate, —COOR$^{Ar1}$, NE$^1$E$^2$, —NR$^{Ar1}$COR$^{Ar2}$, —CONR$^{Ar1}$R$^{Ar2}$, —SO$_2$NR$^{Ar1}$R$^{Ar2}$ and —SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl. In particular, substituted alkynyl groups have one or more, for example 1, 2 or 3 substituent(s) selected from unsubstituted or substituted cycloalkyl, unsubstituted or substituted aryl, fluorine, chlorine, bromine, hydroxyl, alkoxy, polyalkyleneoxy, mercapto, alkylthio, cyano, nitro, NE$^1$E$^2$, —NR$^{Ar1}$COR$^{Ar2}$, —CONR$^{Ar1}$R$^{Ar2}$, —SO$_2$NR$^{Ar1}$R$^{Ar2}$, and —SO$_3$R$^{Ar2}$, where E$^1$, E$^2$, independently of each other, are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, each independently of each, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl. The term "alkoxy" as used herein refers to an alkyl group bound through an oxygen atom, that is, an "alkoxy" group may be represented as —O-alkyl where alkyl is as defined above. C$_1$-C$_2$-Alkoxy is methoxy or ethoxy. C$_1$-C$_4$-Alkoxy is, for example, methoxy, ethoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy).

Accordingly, the term "unsubstituted or substituted alkoxy" as used herein refers to —O-alkyl where alkyl is unsubstituted or substituted as defined above.

The term "polyoxyalkylene" as used herein refers to an alkyl group bound through an oxygen atom to the remainder of the molecule, where alkyl is interrupted by one or more non-adjacent oxygen atoms and alkyl is as defined above.

Accordingly, the term "unsubstituted or substituted polyalkyleneoxy" as used herein refers to —O-alkyl where alkyl is interrupted by one or more non-adjacent oxygen atoms and alkyl is unsubstituted or substituted as defined above.

The term "alkylthio" as used herein refers to an alkyl group bound through a sulfur atom, that is, an "alkylthio" group may be represented as —S-alkyl where alkyl is as defined above. C$_1$-C$_2$-Alkylthio is methylthio or ethylthio. C$_1$-C$_4$-Alkylthio is, for example, methylthio, ethylthio, n-propylthio, 1-methylethylthio (isopropylthio), butylthio, 1-methylpropylthio (sec-butylthio), 2-methylpropylthio (isobutylthio) or 1,1-dimethylethylthio (tert-butylthio).

Accordingly, the term "unsubstituted or substituted alkylthio" as used herein refers to —S-alkyl where alkyl is unsubstituted or substituted as defined above.

The term "cycloalkyl" as used herein refers to mono- or bi- or polycyclic saturated hydrocarbon radicals having usually 3 to 24 (C$_3$-C$_{24}$-cycloalkyl), 3 to 20 ("C$_3$-C$_{20}$-cycloalkyl") atoms, preferably 3 to 8 ("C$_3$-C$_8$-cycloalkyl") or 3 to 6 carbon atoms ("C$_3$-C$_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 to 12 carbon atoms comprise bicyclo[2.2.1]heptyl, bicyclo[3.1.1]heptyl, bicyclo[2.2.2]octyl, bicyclo[3.3.0]octyl, bicyclo[3.2.1]octyl, bicyclo[3.3.1]nonyl, bicyclo[4.2.1]nonyl, bicyclo[4.3.1]decyl, bicyclo[3.3.2]decyl, bicyclo[4.4.0]decyl, bicyclo[4.2.2]decyl, bicyclo[4.3.2] undecyl, bicyclo[3.3.3]undecyl, bicyclo[4.3.3]dodecyl, and perhydronaphthyl. Examples of polycyclic rings are perhydroanthracyl, perhydrofluorenyl, perhydrochrysenyl, perhydropicenyl, and adamantyl.

Substituted cycloalkyl groups may, depending on the ring size, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —COOR$^{Ar1}$, -NE$^1$E$^2$, —NR$^{Ar1}$COR$^{Ar2}$, —CONR$^{Ar1}$R$^{Ar2}$, —SO$_2$NR$^{Ar1}$R$^{Ar2}$ and —SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl. In particular, substituted cycloalkyl groups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, NE$^1$E$^2$, —NR$^{Ar1}$COR$^{Ar2}$, —CONR$^{Ar1}$R$^{Ar2}$, —SO$_2$NR$^{Ar1}$R$^{Ar2}$, and —SO$_3$R$^{Ar2}$, where E$^1$, E$^2$, independently of each other, are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, each independently of each, are hydrogen, unsubstituted or substituted C$_1$-C$_{18}$-alkyl, unsubstituted or substituted C$_3$-C$_{20}$- cycloalkyl, unsubstituted or substituted heterocyclyl, unsubstituted or substituted $C_6$-$C_{20}$-aryl or unsubstituted or substituted heteroaryl.

The term "cycloalkyloxy" as used herein refers to a cycloalkyl group bound through an oxygen atom, that is, a "cycloalkyloxy" group may be represented as —O-cycloalkyl where cycloalkyl is as defined above.

Accordingly, the term "unsubstituted or substituted cycloalkyloxy" as used herein refers to —O-cycloalkyl where cycloalkyl is unsubstituted or substituted as defined above.

The term "cycloalkylthio" as used herein refers to a cycloalkyl group bound through a sulfur atom, that is, a "cycloalkylthio" group may be represented as —S-cycloalkyl where cycloalkyl is as defined above.

Accordingly, the term "unsubstituted or substituted cycloalkylthio" as used herein refers to —S-cycloalkyl where cycloalkyl is unsubstituted or substituted as defined above.

The term "heterocycloalkyl" refers to nonaromatic, partially unsaturated or fully saturated, heterocyclic rings having generally 5 to 8 ring members, preferably 5 or 6 ring members, comprising besides carbon atoms as ring members, one, two, three or four heteroatoms or heteroatom-containing groups selected from O, N, $NR^{cc}$, S, SO and $S(O)_2$ as ring members, wherein $R^{cc}$ is hydrogen, $C_1$-$C_{20}$-alkyl, $C_3$-$C_{24}$-cycloalkyl, heterocycloalkyl, $C_6$-$C_{24}$-aryl or heteroaryl. Examples of heterocycloalkyl groups are especially pyrrolidinyl, piperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —$COOR^{Ar1}$, -$NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted heterocycloalkyl groups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

For the purpose of the present invention, the term "aryl" refers to phenyl and bi- or polycyclic carbocycles having 9 to 24 carbon atoms as ring members and having at least one fused phenylene ring, which is attached to the remainder of the molecule. Examples of bi- or polycyclic carbocycles having at least one phenylene ring include naphthyl, tetrahydronaphthyl, indanyl, indenyl, anthracenyl, fluorenyl etc. Preferably, the term "aryl" denotes phenyl and naphthyl.

Substituted aryls may, depending on the number and size of their ring systems, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —$COOR^{Ar1}$, -$NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted arylgroups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. A special embodiment relates to alkaryl groups, wherein alkyl is unsubstituted. Alkaryl is preferably phenyl which bears 1, 2, 3, 4 or 5, preferably 1, 2 or 3, more preferably 1 or 2 alkyl substituents. Aryl which bears one or more alkyl radicals, is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-n-propylphenyl, 2-, 3- and 4-isopropylphenyl, 2,4-, 2,5-, 3,5- and 2,6-di-n-propylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

$C_6$-$C_{24}$-aryloxy: $C_6$-$C_{24}$-aryl as defined above, which is bonded to the skeleton via an oxygen atom (—O—). Preference is given to phenoxy and naphthyloxy.

Accordingly, the term "unsubstituted or substituted aryloxy" as used herein refers to —O-aryl where aryl is unsubstituted or substituted as defined above.

$C_6$-$C_{24}$-arylthio: $C_6$-$C_{24}$-aryl as defined above, which is bonded to the skeleton via a sulfur atom (—S—). Preference is given to phenylthio and naphthylthio.

Accordingly, the term "unsubstituted or substituted arylthio" as used herein refers to —S-aryl where aryl is unsubstituted or substituted as defined above.

In the context of the present invention, the expression "hetaryl" (also referred to as heteroaryl) comprises heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl groups have 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

Substituted hetaryl groups may, depending on the number and size of their ring systems, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cycloalkyloxy, unsubstituted or substituted aryloxy, unsubstituted or substituted arylthio, cyano, nitro, unsubstituted or substituted alkylcarbonyloxy, formyl, acyl, COOH, carboxylate, —$COOR^{A1}$, -$NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted hetarylgroups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, $R^{Ar1}$ and $R^{Ar2}$ are as defined above. Fused ring systems can comprise alicyclic, aliphatic heterocyclic, aromatic and heteroaromatic rings and combinations thereof, hydroaromatic joined by fusion. Fused ring systems comprise two, three or more (e.g. 4, 5, 6, 7 or 8) rings. Depending on the way in which the rings in fused ring systems are joined, a distinction is made between ortho-fusion, i.e. each ring shares at least one edge or two atoms with each adjacent ring, and peri-fusion in which a carbon atom belongs to more than two rings. Preferred fused ring systems are ortho-fused ring systems.

When # or * appear in a formula showing a substructure of a compound of the present invention, it denotes the attachment bond in the remainder molecule.

Perylene bisimide compound of the formula (I)

In a preferred embodiment, $R^1$ and $R^2$, independently of each other, are selected from the group consisting of linear $C_1$-$C_{24}$-alkyl, branched $C_3$-$C_{24}$-alkyl, $C_6$-$C_{24}$-aryl and $C_6$-$C_{24}$-aryl-$C_1$-$C_{10}$-alkylene, where the rings of aryl, and aryl-alkylene in the two last-mentioned radicals are unsubstituted or substituted with 1, 2, 3, 4 or 5 identical or different radicals $R^a$.

More preferably, $R^1$ and $R^2$, independently of each other, are selected from the group consisting of linear $C_1$-$C_{24}$-alkyl, a radical of the formula (A.1), a radical of the formula (A.2), a radical (A.3), a radical of the formula (B.1), a radical of the formula (B.2) and a radical of the formula (B.3),

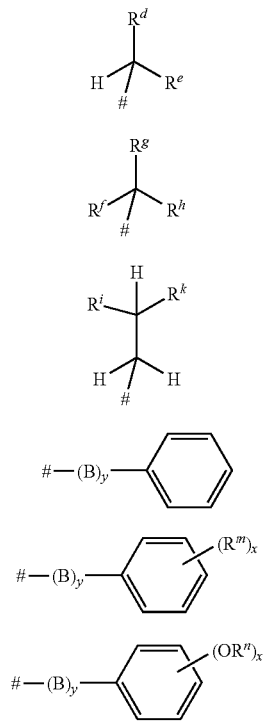

in which
\# represents the bonding site to the nitrogen atom;
$R^d$ and $R^e$, in the formula (A.1), independently from each other are selected from $C_1$-$C_{22}$-alkyl, where the sum of the carbon atoms of the $R^d$ and $R^e$ radicals is an integer from 2 to 23;
$R^f$, $R^g$ and $R^h$, in the formula (A.2) are independently selected from $C_1$- to $C_{21}$-alkyl, where the sum of the carbon atoms of the $R^f$, $R^g$ and $R^h$ radicals is an integer from 3 to 23;
$R^i$ and $R^k$, in the formula (A.3) are independently selected from $C_1$- to $C_{21}$-alkyl, where the sum of the carbon atoms of the $R^i$ and $R^k$ radicals is an integer from 2 to 22; B where present in the formulae (B.1), (B.2) and (B.3), is a $C_1$-$C_{10}$-alkylene group which may be interrupted by one or more nonadjacent groups selected from —O— and —S—;
y is 0 or 1;
$R^m$ is independently of one another selected from $C_1$-$C_{24}$-alkyl, $C_1$-$C_{24}$-fluoroalkyl, fluorine, chlorine or bromine;
$R^n$ is independently of one another selected from $C_1$-$C_{24}$-alkyl;
x in formulae B.2 and B.3 is 1, 2, 3, 4 or 5.

Specific examples of the radical of the formula (A.1) are:
1-methylethyl, 1-methylpropyl, 1-methylbutyl, 1-methylpentyl, 1-methylhexyl, 1-methylheptyl, 1-methyloctyl, 1-ethylpropyl, 1-ethylbutyl, 1-ethylpentyl, 1-ethylhexyl, 1-ethylheptyl, 1-ethyloctyl, 1-propylbutyl, 1-propylpentyl, 1-propylhexyl, 1-propylheptyl, 1-propyloctyl, 1-butylpentyl, 1-butylhexyl, 1-butylheptyl, 1-butyloctyl, 1-pentylhexyl, 1-pentylheptyl, 1-pentyloctyl, 1-hexylheptyl, 1-hexyloctyl, 1-heptyloctyl, especially 1-methylethyl.

Specific examples of the radical of the formula (A.2) are tert.-butyl and 1,1,3,3-tetramethylbutyl.

Specific examples of the radical of the formula (A.3) are isobutyl, 2-methylbutyl or 2-ethylbutyl.

Among the radicals of the formulae (B.1), (B.2) and (B.3), those are preferred, in which y is 0, i.e. the variable B is absent. The variable x in formulae (B.2) and (B.3) is preferably 1, 2 or 3. Irrespectively of its occurrence, $R^m$ is preferably selected from $C_1$-$C_{24}$-alkyl, more preferably linear $C_1$-$C_{10}$-alkyl or branched $C_3$-$C_{10}$-alkyl, especially isopropyl or tert-butyl. Irrespectively of its occurrence, $R^n$ is preferably selected from $C_1$-$C_{24}$-alkyl, more preferably linear $C_1$-$C_{10}$-alkyl or branched $C_3$-$C_{10}$-alkyl. In particular, the radicals of the formula (B.2) are preferred. Specific examples of radicals of the formula (B.2) are 2,6-dimethylphenyl, 2,4-di(tert-butyl)phenyl, 2,6-diisopropylphenyl or 2,6-di(tert-butyl)phenyl.

Preferably, $R^1$ and $R^2$ have the same meaning. In particular, $R^1$ and $R^2$ are both 2,4-di(tert-butyl)phenyl, 2,6-diisopropylphenyl or 2,6-di(tert-butyl)phenyl, especially 2,6-diisopropylphenyl.

Compounds of the formula (I) can be prepared by conventional processes, for example in analogy to methods described in U.S. Pat. No. 4,845,223. They can be prepared by reacting an appropriate chlorinated or brominated perylene bisimide of formula (1)

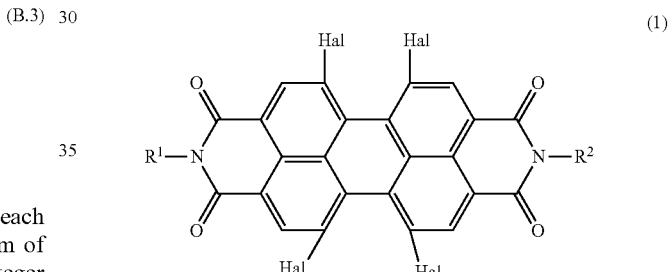

where
Hal is in each case bromine or in each case chlorine; and $R^1$ and $R^2$ are as defined above;
with 2-isopropylphenol.

The reaction is usually carried out in the presence of a base. Suitable bases are in particular inorganic alkali metal or alkaline earth metal bases, the alkali metal bases being particularly suitable. Examples of inorganic bases are the carbonates and hydrogencarbonates, hydroxides, hydrides and amides of alkali metals and alkaline earth metals. Preferred bases are the carbonates and hydrogencarbonates, particular preference being given to the carbonates. Preferred alkali metals are lithium, sodium, potassium and cesium; particularly suitable alkaline earth metals are magnesium and calcium. It will be appreciated that it is also possible to use base mixtures. Very particularly preferred bases are lithium carbonate, sodium carbonate, potassium carbonate and cesium carbonate.

The reaction is usually carried out in the presence of a polar, aprotic solvent. Suitable solvents are especially aliphatic carboxamides, preferably N,N-di-$C_1$-$C_4$-alkyl-$C_1$-$C_4$-carboxamides, lactams such as dimethylformamide, diethylformamide, dimethylacetamide, dimethylbutyramide and N-methyl-2-pyrrolidone (NMP), nitriles such as acetonitrile. It is also possible to use mixtures of polar, aprotic solvents. Particular preference is given to NMP.

The reaction temperature is generally within the range from room temperature to the boiling point of the solvent, preferably 40 to 160° C.

Compounds of formula (1) can be prepared according to literature methods, for example from compounds of formula (2), namely 1,6,7,12-tetrachloroperylene tetracarboxylic acid dianhydride or 1,6,7,12 tetrabromoperylene tetracarboxylic acid dianhydride

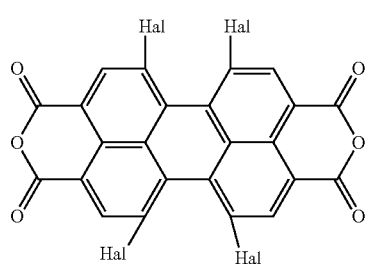

(2)

where
Hal is in each case bromine or in each case chlorine;
by condensation with a primary amine of formula $R^1$—$NH_2$ and, if appropriate a primary amine of formula $R^2$—$NH_2$, where $R^1$ and $R^2$ are as defined above, where $R^2$ may also be as defined for $R^1$ (if only one amine of the formula $R^1$—$NH_2$ is used for the imidation). The imidation reaction is carried out according to standard methods, e.g. as described by Bartholomew et al., in Chem. Commun., 2008, 6594-6596 including Supplementary Material (ESI) for Chemical Communications.

1,6,7,12-Tetrachloroperylene tetracarboxylic acid dianhydride is commercially available; 1,6,7,12-tetrabromoperylene tetracarboxylic acid dianhydride can be prepared as described by Bartholomew et al., in Chem. Commun., 2008, 6594-6596 including Supplementary Material (ESI). 2-Isopropylphenol is commercially available.

The compound of formula (I) is usually a red-fluorescent one.

The compound of the formula (I) and mixtures thereof may be incorporated without any problem into organic and inorganic materials and are therefore suitable for a whole series of end uses.

The inventive perylene bisimide compound of the formula (I) and mixtures thereof are especially notable as fluorescent colorants in color converters.

Color Converters

Accordingly, the present invention further provides a color converter comprising at least one polymer as a matrix and at least one perylene bisimide compound of formula (I) as defined above as a fluorescent colorant, wherein the at least one polymer consists essentially of polystyrene, polycarbonate, polyacrylate, polymethylmethacrylate, polymethacrylate, polyvinylpyrrolidone, polyvinyl acetate, polyvinyl chloride, polybutene, silicone, epoxy resin, polyvinyl alcohol, poly(ethylene vinylalcohol)-coplymer, polyacrylonitrile, polyvinylidene chloride, polystyrene acrylonitrile, polybutylene terephthalate, polyethylene terephthalate, a 2,5-furandicarboxylate polyester, polyvinyl butyrate, polyvinyl chloride, polyamides, polyoxymethylenes, polyimides, polyetherimides or mixtures thereof.

Especially, the at least one polymer consists essentially of polystyrene, polycarbonate, polyethylene terephthalate, polyethylene furanoate.

Polystyrene is understood here to mean, inter alia, all homo- or copolymers which result from polymerization of styrene and/or derivatives of styrene. Derivatives of styrene are, for example, alkylstyrenes such as alpha-methylstyrene, ortho-, meta-, para-methylstyrene, para-butylstyrene, especially para-tert-butylstyrene, alkoxystyrene such as para-methoxystyrene, para-butoxystyrene, para-tert-butoxystyrene. In general, suitable polystyrenes have a mean molar mass Mn of 10 000 to 1 000 000 g/mol (determined by GPC), preferably 20 000 to 750 000 g/mol, more preferably 30 000 to 500 000 g/mol.

In a preferred embodiment, the matrix of the color converter consists essentially or completely of a homopolymer of styrene or styrene derivatives. More particularly, the polymer completely consists of polystyrene.

In a further preferred embodiments of the invention, the matrix consists essentially or completely of a styrene copolymer, which are likewise regarded as polystyrene in the context of this application. Styrene copolymers may comprise, as further constituents, for example, butadiene, acrylonitrile, maleic anhydride, vinylcarbazole or esters of acrylic, methacrylic or itaconic acid as monomers. Suitable styrene copolymers generally comprise at least 20% by weight of styrene, preferably at least 40% and more preferably at least 60% by weight of styrene. In another embodiment, they comprise at least 90% by weight of styrene.

Preferred styrene copolymers are styrene-acrylonitrile copolymers (SAN) and acrylonitrile-butadiene-styrene copolymers (ABS), styrene-1,1'-diphenylethene copolymers, acrylic ester-styrene-acrylonitrile copolymers (ASA), methyl methacrylate-acrylonitrile-butadiene-styrene copolymers (MABS). A further preferred polymer is alpha-methylstyrene-acrylonitrile copolymer (AMSAN). The styrene homo- or copolymers can be prepared, for example, by free-radical polymerization, cationic polymerization, anionic polymerization or under the influence of organometallic catalysts (for example Ziegler-Natta catalysis). This can lead to isotactic, syndiotactic or atactic polystyrene or copolymers. They are preferably prepared by free-radical polymerization. The polymerization can be performed as a suspension polymerization, emulsion polymerization, solution polymerization or bulk polymerization. The preparation of suitable polystyrenes is described, for example, in Oscar Nuyken, Polystyrenes and Other Aromatic Polyvinyl Compounds, in Kricheldorf, Nuyken, Swift, New York 2005, p. 73-150 and references cited therein; and in Elias, Macromolecules, Weinheim 2007, p. 269-275.

In another preferred embodiment, the polymer consists essentially or completely of polyethylene terephthalate. Polyethylene terephthalate is obtainable by condensation of ethylene glycol with terephthalic acid. Preferably, the polymer completely consists of polyethylene terephthalate.

Likewise more particularly, the polymer consists essentially or completely of polycarbonate. More preferably, the polymer completely consists of polycarbonate. Polycarbonates are polyesters of carbonic acid with aromatic or aliphatic dihydroxyl compounds. Preferred dihydroxyl compounds are, for example, methylenediphenylene-dihydroxyl compounds, for example bisphenol A. One means of preparing polycarbonates is the reaction of suitable dihydroxyl compounds with phosgene in an interfacial polymerization. Another means is the reaction with diesters of carbonic acid such as diphenyl carbonate in a condensation polymerization. The preparation of suitable polycarbonates is described, for example, in Elias, Macromolecules, Weinheim 2007, p. 343-347.

Likewise more particularly, the polymer consists essentially or completely of 2,5-furandicarboxylate polyester. 2,5-furandicarboxylate polyesters are obtainable by reacting (i) at least one diol selected from an aliphatic $C_2$-$C_{20}$-diol and a cycloaliphatic $C_3$-$C_{20}$-diol, with (ii) 2,5-furandicarboxylic acid and/or an ester forming derivative thereof and (iii) optionally at least one further dicarboxylic acid selected from 1,2-cyclohexanedicarboxylic acid, 1,4-cyclohexanedicarboxylic acid, 3,4-furandicarboxylic acid, terephthalic acid and 2,6-naphthalic acid and/or an ester forming derivative thereof.

Suitable aliphatic $C_2$-$C_{20}$-diols are preferably linear or branched $C_2$-$C_{15}$-alkanediols, especially linear or branched $C_2$-$C_{10}$-alkanediols such as ethane-1,2-diol (ethylene glycol), propane-1,2-diol, propane-1,3-diol (propylene glycol), butane-1,3-diol, butane-1,4-diol (butylene glycol), 2-methyl-1,3-propanediol, pentane-1,5-diol, 2,2-dimethyl-1,3-propanediol (neopentyl glycol), hexane-1,6-diol, heptane-1,7-diol, octane-1,8-diol, nonane-1,9-diol, decane-1,10-diol, etc. Suitable cycloaliphatic $C_3$-$C_{20}$-diols are preferably $C_3$-$C_{10}$-cycloalkylenediols, such as 1,2-cyclopentanediol, 1,3-cyclopentanediol, 1,2-cyclohexanediol, 1,4-cyclohexanediol, 1,2-cycloheptanediol or 1,4-cycloheptanediol. Other suitable cycloaliphatic $C_3$-$C_{20}$-diols include 1,3-cyclohexane dimethanol and 1,4-cyclohexane dimethanol, or 2,2,4,4-tetramethyl-1,3-cyclobutanediol, or combinations thereof. Particularly preferred diols are $C_2$-$C_6$-alkanediols, in particular ethane-1,2-diol, propane-1,2-diol, propane-1,3-diol, butane-1,3-diol, butane-1,4-diol, pentane-1,5-diol, 2,2-dimethyl-1,3-propanediol and mixtures thereof. More particularly preferred are ethane-1,2-diol and propane-1,3-diol, especially ethane-1,2-diol.

More particularly preferred are also biologically derived ("bio-derived") $C_2$-$C_{10}$-alkanediols, especially $C_2$-$C_6$-alkanediols such as ethane-1,2-diol and propane-1,3-diol. Bio-based ethane-1,2-diol may be obtained from a lignocellulosic biomass source by the conversion of the carbohydrates therein contained. Methods for preparing $C_2$-$C_{10}$-alkanediols from biomass are known in the art, for example from US 2011/0306804.

Preferably, the diol component (i) is made up exclusively of one diol mentioned as preferred, especially ethane-1,2-diol. The diol component (i) may also comprise two, three or more than three different diols. If two, three or more than three different diols are used, preference is given to those mentioned above as being preferred. In this case, based on the total weight of component (i), ethane-1,2-diol is preferably the major component.

Ester forming derivatives of 2,5-furandicarboxylic acids are especially $C_1$-$C_{10}$-dialkyl esters of 2,5-furandicarboxylic acid. Particularly preferred diesters are $C_1$-$C_6$-dialkyl esters of 2,5-furandicarboxylic acid, especially the dimethyl ester and diethyl ester. Component (ii) may also comprise two, three or more than three different diesters of 2,5-furandicarboxylic acid. 2,5-Furandicarboxylic acid can be produced from bio-based sugars. Routes for the preparation of 2,5-furandicarboxylic acid using air oxidation of 2,5-disubstituted furans such as 5-hydroxymethylfurfural with catalysts comprising Co, Mn and/or Ce were reported recently in WO 2010/132740, WO 2011/043660, WO 2011/043661, US 2011/0282020, US 2014/0336349 and WO 2015/137804.

Routes for the preparation of dialkyl ester of 2,5-furandicarboxylic acid are also described for example in WO 2011/043661.

Preferably, the polymer is made up exclusively of (i) one diol selected from an aliphatic $C_2$-$C_{20}$-diol and a cycloaliphatic $C_3$-$C_{20}$-diol and (ii) a 2,5-furandicarboxylic acid or of diester(s) of 2,5-furandicarboxylic acid.

Preferably, the 2,5-furandicarboxylate polyester is selected from poly(ethylene-2,5-furandicarboxylate), poly(propylene-2,5-furandicarboxylate), poly(ethylene-co-propylene-2,5-furandicarboxylate), poly(butylene-2,5-furandicarboxylate), poly(pentylene-2,5-furandicarboxylate), poly(neopentylene-2,5-furandicarboxylate) and mixtures thereof. In particular, the polymeric matrix material for use in the color converter according to the invention can consist of or can consist essentially of from poly(ethylene-2,5-furandicarboxylate), poly(trimethylene-2,5-furandicarboxylate) and poly(butylene-2,5-furandicarboxylate). Especially, the polymeric matrix material for use in the color converter according to the invention consists of poly(ethylene-2,5-furan-dicarboxylate). In a further specific embodiment, the polymeric matrix material of the color converter comprises a mixture (blend) of different 2,5-furandicarboxylate polyesters as defined above, for example, a blend of poly(ethylene-2,5-furandicarboxylate) and poly(propylene-2,5-furandicarboxylate). Poly(propylene-2,5-furandicarboxylate) is also referred to as poly(trimethylene 2,5-furandicarboxylate); poly(butylene-2,5-furandicarboxylate) is also referred to as poly(tetramethylene 2,5-furandicarboxylate), poly(pentylene-2,5-furandicarboxylate) is also referred to as poly(pentamethylene 2,5-furan-dicarboxylate).

Likewise suitable are 2,5-furandicarboxylate polyesters obtainable by reacting at least one diol component (i) as defined above, component (ii) as defined above and at least one further diacid or diester component (iii) selected from 1,2-cyclohexanedicarboxylic acid, 1,4-cyclohexanedicarboxylic acid, 3,4-furandicarboxylic acid, terephthalic acid and 2,6-naphthalic acid and/or an ester forming derivative thereof. Ester forming derivative of 1,2-cyclohexanedicarboxylic acid, 1,4-cyclohexanedicarboxylic acid, 3,4-furandicarboxylic acid, terephthalic acid and 2,6-naphthalic acid are especially the $C_1$-$C_{10}$-dialkyl ester. Particularly preferred esters are $C_1$-$C_6$-dialkyl ester, especially the dimethyl ester and diethyl ester. When using a combination of component (ii) and component (iii), component (ii) is the major component based on the total weight of component (ii) and (iii). Examples are poly(ethylene-2,5-furandicarboxylate-co-1,2-cyclohexanedicarboxylate), poly(ethylene-2,5-furandicarboxylate-co-1,4-cyclohexanedicarboxylate), poly(ethylene-2,5-furandicarboxylate-co-terephthalate), poly(ethylene-2,5-furandicarboxylate-co-2,6-naphthalate) or poly(ethylene-2,5-furandicarboxylate-co-3,4-furandicarboxylate), preferably poly(ethylene-2,5-furandicarboxylate-co-terephthalate), poly(ethylene-2,5-furandicarboxylate-co-2,6-naphthalate) or poly(ethylene-2,5-furandicarboxylate-co-3,4-furandicarboxylate.

The 2,5-furandicarboxylate polyester (A) can be prepared as described in U.S. Pat. No. 2,551,731.

In particular, the polymer consists of polystyrene. Likewise in particular, the polymer consists of polycarbonate. Likewise in particular, the polymer consists of polyethylene terephthalate. Likewise in particular, the polymer consists of polyethylene furanoate.

In a preferred embodiment, polymers which have been polymerized with exclusion of oxygen are used. Preferably, the monomers during the polymerization comprised a total of not more than 1000 ppm of oxygen, more preferably not more than 100 ppm and especially preferably not more than 10 ppm.

Typically, the concentration of the compound of formula (I) is in the range from 0.0001 to 0.5% by weight, preferably 0.001 to 0.1% by weight, based on the amount of polymer used.

Suitable polymers may comprise, as further constituents, additives such as flame retardants, antioxidants, light stabilizers, UV absorbers, free-radical scavengers, antistats. Stabilizers of this kind are known to those skilled in the art.

Suitable antioxidants or free-radical scavengers are, for example, phenols, especially sterically hindered phenols such as butylhydroxyanisole (BHA) or butylhydroxytoluene (BHT), or sterically hindered amines (HALS). Stabilizers of this kind are sold, for example, by BASF under the Irganox® trade name. In some cases, antioxidants and free-radical scavengers can be supplemented by secondary stabilizers such as phosphites or phosphonites, as sold, for example, by BASF under the Irgafos® trade name.

Suitable UV absorbers are, for example, benzotriazoles such as 2-(2-hydroxyphenyl)-2H-benzotriazole (BTZ), triazines such as (2-hydroxyphenyl)-s-triazine (HPT), hydroxybenzophenones (BP) or oxalanilides. UV absorbers of this kind are sold, for example, by BASF under the Uvinul® trade name.

In a preferred embodiment of the invention, suitable polymers do not comprise any antioxidants or free-radical scavengers.

In a further embodiment of the invention, suitable polymers are transparent polymers.

In another embodiment, suitable polymers are opaque polymers.

According to a preferred embodiment, the color converter additionally comprises at least one inorganic white pigment as a scattering body.

Suitable scattering bodies are inorganic white pigments, for example titanium dioxide, barium sulphate, lithopone, zinc oxide, zinc sulphide, calcium carbonate with a mean particle size to DIN 13320 of 0.01 to 10 μm, preferably 0.1 to 1 μm, more preferably 0.15 to 0.4 μm, especially scattering bodies based on $TiO_2$.

Scattering bodies are included typically in an amount of 0.01 to 2.0% by weight, preferably 0.05 to 1% by weight, more preferably 0.1 to 0.5% by weight, based in each case on the polymer of the layer comprising scattering bodies.

The polymers mentioned above serve as a matrix material for the compounds of formula (I) and if present, other organic fluorescent colorants described hereinafter. The fluorescent colorant(s) of formula (I) but, optionally also other organic fluorescent colorants described hereinafter may either be dissolved in the polymer or may be in the form of a homogeneously distributed mixture. In a preferred embodiment, the color converters comprise, at least one inventive fluorescent colorant of the formula (I) or mixtures thereof and at least one further organic fluorescent colorant.

Preferably, the color converter comprises at least one further organic fluorescent colorant (B) selected from the groups:

(B1) a cyanated naphthoylbenzimidazole compound of formula (II)

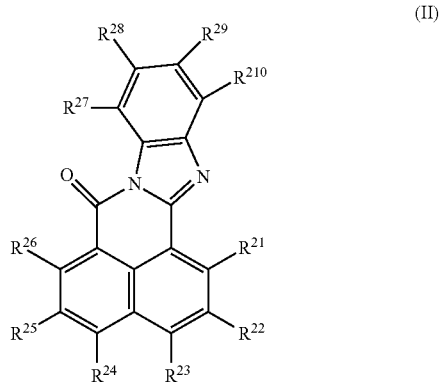

wherein
$R^{21}, R^{22}, R^{23}, R^{24}, R^{25}, R^{26}, R^{27}, R^{28}, R^{29}$ and $R^{210}$ are each independently hydrogen, cyano or aryl which is unsubstituted or has one or more identical or different substituents $R^{2Ar}$, where
each $R^{2Ar}$ is independently selected from cyano, hydroxyl, mercapto, halogen, $C_1$-$C_{20}$-alkoxy, $C_1$-$C_{20}$-alkylthio, nitro, $-NR^{2Ar2}R^{2Ar3}$, $-NR^{2Ar2}COR^{2Ar3}$, $-CONR^{2Ar2}R^{2Ar3}$, $-SO_2NR^{2Ar2}R^{2Ar3}$, $-COOR^{2Ar2}$, $-SO_3R^{2Ar2}$, $C_1$-$C_{30}$-alkyl, $C_2$-$C_{30}$-alkenyl, $C_2$-$C_{30}$-alkynyl, where the three latter radicals are unsubstituted or bear one or more $R^{2a}$ groups, $C_3$-$C_8$-cycloalkyl, 3- to 8-membered heterocyclyl, where the two latter radicals are unsubstituted or bear one or more $R^{2b}$ groups, aryl, U-aryl, heteroaryl and U-heteroaryl, where the four latter radicals are unsubstituted or bear one or more $R^{2b}$ groups, where
each $R^{2a}$ is independently selected from cyano, hydroxyl, oxo, mercapto, halogen, $C_1$-$C_{20}$-alkoxy, $C_1$-$C_{20}$-alkylthio, nitro, $-NR^{2Ar2}R^{Ar3}$, $-NR^{2Ar2}COR^{2Ar3}$, $-CONR^{2Ar2}R^{Ar3}$, $-SO_2NR^{2Ar2}R^{Ar3}$, $-COOR^{2Ar2}$, $-SO_3R^{2Ar2}$, $C_3$-$C_8$-cycloalkyl, 3- to 8-membered heterocyclyl, aryl and heteroaryl, where the cycloalkyl, heterocyclyl, aryl and heteroaryl radicals are unsubstituted or bear one or more $R^{2b}$ groups;

each $R^{2b}$ is independently selected from cyano, hydroxyl, oxo, mercapto, halogen, $C_1$-$C_{20}$-alkoxy, $C_1$-$C_{20}$-alkylthio, nitro, $-NR^{2Ar2}R^{2Ar3}$, $-NR^{2Ar2}COR^{2Ar3}$, $-CONR^{2Ar2}R^{2Ar3}$, $-SO_2NR^{2Ar2}R^{2Ar3}$, $-COOR^{2Ar2}$, $-SO_3R^{2Ar2}$, $C_1$-$C_{18}$-alkyl, $C_2$-$C_{18}$-alkenyl, $C_2$-$C_{18}$-alkynyl, $C_3$-$C_8$-cycloalkyl, 3- to 8-membered heterocyclyl, aryl and heteroaryl, where the four latter radicals are unsubstituted or bear one or more $R^{2b1}$ groups, each $R^{2b1}$ is independently selected from cyano, hydroxyl, mercapto, oxo, nitro, halogen, $-NR^{2Ar2}R^{2Ar3}$, $-NR^{2Ar2}COR^{2Ar3}$, $-CONR^{2Ar2}R^{2Ar3}$, $-SO_2NR^{2Ar2}R^{2Ar3}$, $-COOR^{2Ar2}$, $-SO_3R^{2Ar2}$, $-SO_3R^{2Ar2}$, $C_1$-$C_{18}$-alkyl, $C_2$-$C_{18}$-alkenyl, $C_2$-$C_{18}$-alkynyl, $C_1$-$C_{12}$-alkoxy, and $C_1$-$C_{12}$-alkylthio, U is an —O—, —S—, —NR$^{24r1}$-, —CO—, —SO— or —SO$_2$— moiety;

R$^{24r1}$, R$^{24r2}$, R$^{24r3}$ are each independently hydrogen, C$_1$-C$_{18}$-alkyl, 3- to 8-membered cycloalkyl, 3- to 8-membered heterocyclyl, aryl or heteroaryl, where alkyl is unsubstituted or bears one or more R$^{2a}$ groups, where 3- to 8-membered cycloalkyl, 3- to 8-membered heterocyclyl, aryl and heteroaryl are unsubstituted or bear one or more R$^{2b}$ groups;

with the proviso that the compound of formula II comprises at least one cyano group, and mixtures thereof;

(B2) a cyanated perylene compound of formula (III)

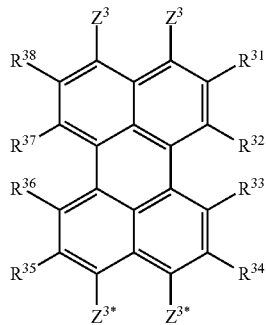

(III)

in which one of the Z$^3$ substituents is cyano and the other Z$^3$ substituent is CO$_2$R$^{39}$, CONR$^{310}$R$^{311}$, C$_1$-C$_{18}$-alkyl, C$_2$-C$_{18}$-alkenyl, C$_2$-C$_{18}$-alkynyl, C$_3$-C$_{12}$-cycloalkyl or C$_6$-C$_{14}$-aryl, where C$_1$-C$_{18}$-alkyl, C$_2$-C$_{18}$-alkenyl, C$_2$-C$_{18}$-alkynyl are unsubstituted or bear one or more identical or different Z$^{3a}$ substituents, C$_3$-C$_{12}$-cycloalkyl is unsubstituted or bears one or more identical or different Z$^{3b}$ substituents, and C$_6$-C$_{14}$-aryl is unsubstituted or bears one or more identical or different Z$^{3Ar}$ substituents;

one of the Z$^{3*}$ substituents is cyano and the other Z$^{3*}$ substituent is CO$_2$R$^{39}$, CONR$^{310}$R$^{311}$, C$_1$-C$_{18}$-alkyl, C$_2$-C$_{18}$-alkenyl, C$_2$-C$_{18}$-alkynyl, C$_3$-C$_{12}$-cycloalkyl or C$_6$-C$_{14}$-aryl, where C$_1$-C$_{18}$-alkyl, C$_2$-C$_{18}$-alkenyl, C$_2$-C$_{18}$-alkynyl are unsubstituted or bear one or more identical or different Z$^{3a}$ substituents, C$_3$-C$_{12}$-cycloalkyl is unsubstituted or bears one or more identical or different Z$^{3b}$ substituents, and C$_6$-C$_{14}$-aryl is unsubstituted or bears one or more identical or different Z$^{3Ar}$ substituents;

R$^{31}$, R$^{32}$, R$^{33}$, R$^{34}$, R$^{35}$, R$^{36}$, R$^{37}$ and R$^{38}$ are each independently selected from hydrogen, cyano, bromine and chlorine, with the proviso that 1, 2, 3, 4, 5, 6, 7 or 8 of the R$^{31}$, R$^{32}$, R$^{33}$, R$^{34}$, R$^{35}$, R$^{36}$, R$^{37}$ or R$^{38}$ substituents are cyano;

where

R$^{39}$ is hydrogen, C$_1$-C$_{10}$-alkyl, C$_2$-C$_{10}$-alkenyl, C$_2$-C$_{10}$-alkynyl, C$_3$-C$_{12}$-cycloalkyl or C$_6$-C$_{14}$-aryl, where C$_1$-C$_{10}$-alkyl, C$_2$-C$_{10}$-alkenyl, C$_2$-C$_{10}$-alkynyl are unsubstituted or bear one or more identical or different R$^{3a}$ substituents, C$_3$-C$_{12}$-cycloalkyl is unsubstituted or bears one or more identical or different R$^{3b}$ substituents and C$_6$-C$_{14}$-aryl is unsubstituted or bears one or more identical or different R$^{3Ar}$ substituents;

R$^{310}$ and R$^{311}$ are each independently hydrogen, C$_1$-C$_{10}$-alkyl, C$_2$-C$_{10}$-alkenyl, C$_2$-C$_{10}$-alkynyl, C$_3$-C$_{12}$-cycloalkyl or C$_6$-C$_{14}$-aryl, where C$_1$-C$_{10}$-alkyl, C$_2$-C$_{10}$-alkenyl, C$_2$-C$_{10}$-alkynyl are unsubstituted or bear one or more identical or different R$^{3a}$ substituents, C$_3$-C$_{12}$-cycloalkyl is unsubstituted or bears one or more identical or different R$^{3b}$ substituents and C$_6$-C$_{14}$-aryl is unsubstituted or bears one or more identical or different R$^{3Ar}$ substituents;

each Z$^{3a}$ is independently halogen, hydroxyl, NR$^{310a}$R$^{311a}$, C$_1$-C$_{10}$-alkoxy, C$_1$-C$_{10}$-haloalkoxy, C$_1$-C$_{10}$-alkylthio, C$_3$-C$_{12}$-cycloalkyl, C$_6$-C$_{14}$-aryl, C(=O)R$^{39a}$; C(=O)OR$^{39}$a or C(O)NR$^{310a}$R$^{311a}$, where C$_3$-C$_{12}$-cycloalkyl is unsubstituted or bears one or more identical or different R$^{3b}$ substituents and C$_6$-C$_{14}$-aryl is unsubstituted or bears one or more identical or different R$^{3Ar}$ substituents;

each Z$^{3b}$ and each Z$^{3Ar}$ is independently halogen, hydroxyl, NR$^{310a}$R$^{311a}$, C$_1$-C$_{10}$-alkyl, C$_1$-C$_{10}$-alkoxy, C$_1$-C$_{10}$-haloalkoxy, C$_1$-C$_{10}$-alkylthio, C(=O)R$^{39a}$; C(=O)OR$^{39a}$ or C(O)NR$^{310a}$R$^{311a}$;

each R$^{3a}$ is independently halogen, hydroxyl, C$_1$-C$_{10}$-alkoxy, C$_3$-C$_{12}$-cycloalkyl or C$_6$-C$_{14}$-aryl;

each R$^{3b}$ is independently halogen, hydroxyl, C$_1$-C$_{10}$-alkyl, C$_1$-C$_{10}$-alkoxy, C$_1$-C$_{10}$-haloalkoxy, C$_1$-C$_{10}$-alkylthio, C$_2$-C$_{10}$-alkenyl, C$_2$-C$_{10}$-alkynyl, C$_3$-C$_{12}$-cycloalkyl or C$_6$-C$_{14}$-aryl;

each R$^{3Ar}$ is independently halogen, hydroxyl, C$_1$-C$_{10}$-alkyl, C$_1$-C$_{10}$-alkoxy, C$_1$-C$_{10}$-haloalkoxy, C$_1$-C$_{10}$-alkylthio, C$_2$-C$_{10}$-alkenyl, C$_2$-C$_{10}$-alkynyl, C$_3$-C$_{12}$-cycloalkyl or C$_6$-C$_{14}$-aryl;

R$^{39a}$ is hydrogen, C$_1$-C$_{10}$-alkyl, C$_2$-C$_{10}$-alkenyl, C$_2$-C$_{10}$-alkynyl, C$_3$-C$_{12}$-cycloalkyl or C$_6$-C$_{14}$-aryl; and R$^{310a}$, R$^{311a}$ are each independently hydrogen, C$_1$-C$_{10}$-alkyl, C$_2$-C$_{10}$-alkenyl, C$_2$-C$_{10}$-alkynyl, C$_3$-C$_{12}$-cycloalkyl or C$_6$-C$_{14}$-aryl, and mixtures thereof;

(B3) a cyanated compound of formula (IV)

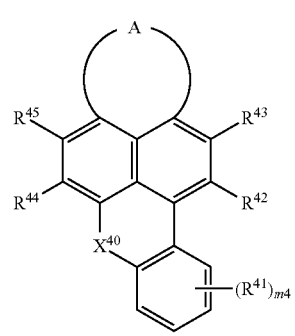

(IV)

wherein m4 is 0, 1, 2, 3 or 4;

each R$^{41}$ independently from each other is selected from bromine, chlorine, cyano, —NR$^{4a}$R$^{4b}$, C$_1$-C$_{24}$-alkyl, C$_1$-C$_{24}$-haloalkyl, C$_1$-C$_{24}$-alkoxy, C$_1$-C$_{24}$-haloalkoxy, C$_3$-C$_{24}$-cycloalkyl, heterocycloalkyl, heteroaryl, C$_6$-C$_{24}$-aryl, C$_6$-C$_{24}$-aryloxy, C$_6$-C$_{24}$-aryl-C$_1$-C$_{10}$-alkylene, where the rings of cycloalkyl, heterocycloalkyl, heteroaryl, aryl, aryloxy in the six last-mentioned radicals are unsubstituted or substituted with 1, 2, 3, 4 or 5 identical or different radicals $R^{41a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from O, S and $NR^{4c}$;

at least one of the radicals $R^{42}$, $R^{43}$, $R^{44}$ and $R^{45}$ is CN, and the remaining radicals, independently from each other, are selected from hydrogen, chlorine and bromine;

$X^{40}$ is O, S, SO or $SO_2$;

A is a diradical selected from diradicals of the general formulae (A.1), (A.2), (A.3), and (A.4)

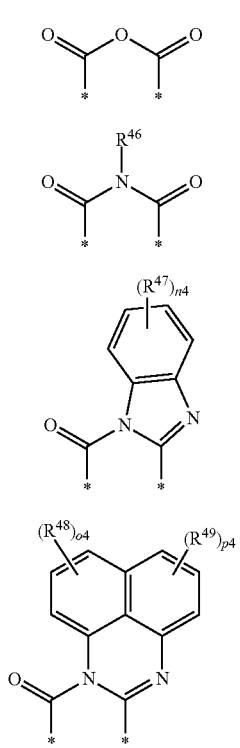

wherein
in each case denotes the point of attachments to the remainder of the molecule;
n4 is 0, 1, 2, 3 or 4;
o4 is 0, 1, 2 or 3;
p4 is 0, 1, 2 or 3;
$R^{46}$ is hydrogen, $C_1$-$C_{24}$-alkyl, $C_1$-$C_{24}$-haloalkyl, $C_3$-$C_{24}$-cycloalkyl, $C_6$-$C_{24}$-aryl or $C_6$-$C_{24}$-aryl-$C_1$-$C_{10}$-alkylene, where the rings of cycloalkyl, aryl, and aryl-alkylene in the three last-mentioned radicals are unsubstituted or substituted with 1, 2, 3, 4 or 5 identical or different radicals $R^{46a}$, and where $C_1$-$C_{24}$-alkyl, $C_1$-$C_{24}$-haloalkyl and the alkylene moiety of $C_6$-$C_{24}$-aryl-$C_1$-$C_{10}$-alkylene may be interrupted by one or more heteroatoms or heteroatomic groups selected from O, S and $NR^{4c}$;

each $R^{47}$ independently from each other is selected from bromine, chlorine, cyano, —$NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{47a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;

each $R^{48}$ independently from each other is selected from bromine, chlorine, cyano, $NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{48a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;

each $R^{49}$ independently from each other is selected from bromine, chlorine, cyano, $NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{49a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;

$R^{41a}$, $R^{46a}$, $R^{47a}$, $R^{48a}$, $R^{49a}$ are independently of one another selected from $C_1$-$C_{24}$-alkyl, $C_1$-$C_{24}$-fluoroalkyl, $C_1$-$C_{24}$-alkoxy, fluorine, chlorine and bromine;

$R^{4a}$, $R^{4b}$, $R^{4c}$ are independently of one another are selected from hydrogen, $C_1$-$C_{20}$-alkyl, $C_3$-$C_{24}$-cycloalkyl, heterocycloalkyl, heteroaryl and $C_6$-$C_{24}$-aryl;

and mixtures thereof;

(B4) a benz(othi)oxanthene compound of formula (V)

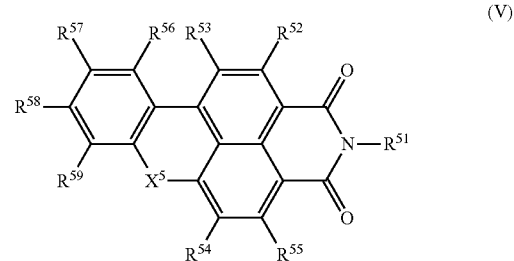

wherein
$X^5$ is oxygen or sulfur;
$R^{51}$ is phenyl which is unsubstituted or carries 1, 2, 3, 4, or 5 substituents selected from halogen, $R^{511}$, $OR^{552}$, $NHR^{552}$ and $NR^{552}R^{557}$;

$R^{52}$, $R^{53}$, $R^{54}$, $R^{55}$, $R^{56}$, $R^{57}$, $R^{58}$ and $R^{59}$ are independently of each other selected from hydrogen, halogen, $R^{553}$, $OR^{553}$, $NHR^{553}$ and $NR^{553}R^{554}$,
wherein
$R^{511}$ is selected from $C_1$-$C_{24}$-alkyl, $C_6$-$C_{24}$-aryl and heteroaryl;
$R^{552}$ and $R^{557}$ are independently of each other selected from $C_1$-$C_{18}$-alkyl, $C_6$-$C_{24}$-aryl and heteroaryl; and
$R^{553}$ and $R^{554}$ are independently of each other selected from $C_1$-$C_{18}$-alkyl, $C_6$-$C_{24}$-aryl and heteroaryl;
and mixtures thereof;
(B5) a benzimidazoxanthenisoquinoline compound of formulae (VIA) or (VIB)

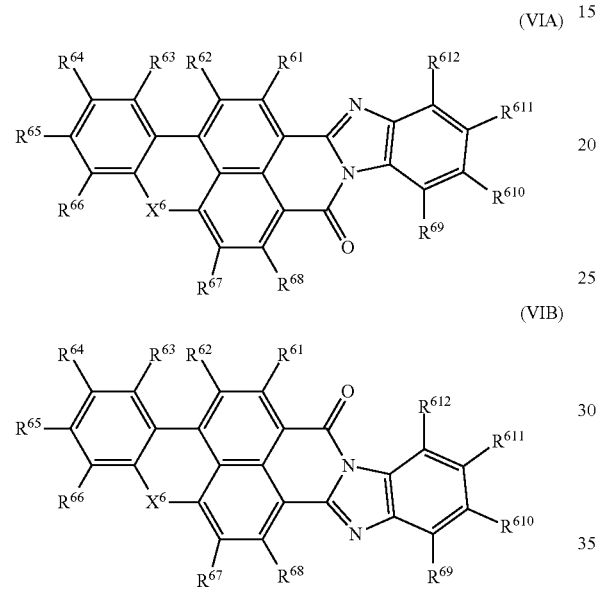

wherein
$X^6$ is oxygen or sulfur;
$R^{61}$, $R^{62}$, $R^{63}$, $R^{64}$, $R^{65}$, $R^{66}$, $R^{67}$, $R^{68}$, $R^{69}$, $R^{610}$, $R^{611}$ and $R^{612}$ are independently of each other selected from hydrogen, halogen, $R^{661}$, $OR^{661}$, $NHR^{661}$ and $NR^{661}R^{662}$
wherein
each $R^{661}$ is selected from $C_1$-$C_{18}$-alkyl, $C_6$-$C_{24}$-aryl and heteroaryl; and
each $R^{662}$ is selected from $C_1$-$C_{18}$-alkyl, $C_6$-$C_{24}$-aryl and heteroaryl;
and mixtures thereof;
(B6) fluorescent compound comprising at least one structural unit of formula (VII)

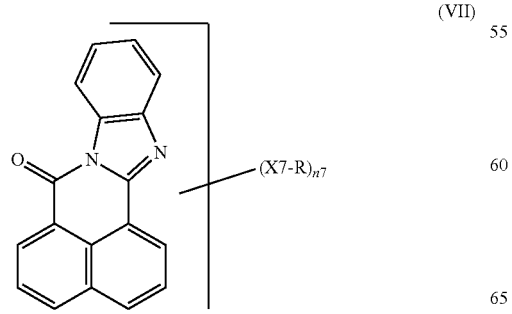

where one or more CH groups of the six-membered ring of the benzimidazole structure shown may be replaced by nitrogen and where the symbols are each defined as follows:
n7 is a number from 0 to (10-p7) for each structural unit of the formula (VII); where p7 is the number of CH units which have been replaced by nitrogen in the six-membered ring of the benzimidazole structure shown
X7 is a chemical bond, O, S, SO, $SO_2$, $NR^{71}$; and
R is an aliphatic radical, cycloaliphatic radical, aryl, heteroaryl, each of which may bear substituents,
an aromatic or heteroaromatic ring or ring system, each of which is fused to other aromatic rings of the structural unit of the formula (VII),
is F, Cl, Br, CN, H when X7 is not a chemical bond;
where two R radicals may be joined to give one cyclic radical and where X7 and R, when n7>one, may be the same or different;
$R^{71}$ is each independently hydrogen, $C_1$-$C_{18}$-alkyl or cycloalkyl, the carbon chain of which may comprise one or more —O—, —S—, —CO—, —SO— and/or —$SO_2$— moieties and which may be mono- or polysubstituted;
aryl or heteroaryl which may be mono- or polysubstituted;
and mixtures thereof;
(B7) a perylene compound of formulae (VIII) or (IX)

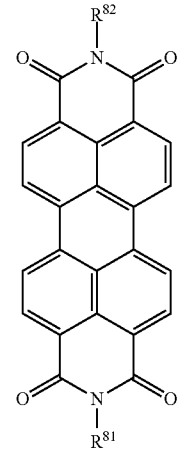

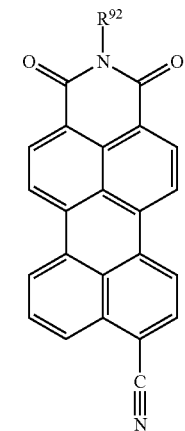

where

R$^{81}$, R$^{82}$ are each independently C$_1$-C$_{30}$-alkyl, C$_2$-C$_{30}$-alkyl which is interrupted by one or more oxygen, C$_3$-C$_8$-cycloalkyl, C$_6$-C$_{10}$-aryl, heteroaryl, C$_6$-C$_{10}$-aryl-C$_1$-C$_{10}$-alkylene, where the aromatic ring in the three latter radicals is unsubstituted or mono- or polysubstituted by C$_1$-C$_{10}$-alkyl;

R$^{92}$ is C$_1$-C$_{30}$-alkyl, C$_3$-C$_8$-cycloalkyl, aryl, heteroaryl, aryl-C$_1$-C$_{10}$-alkylene, where the aromatic ring in the three latter radicals is unsubstituted or mono- or polysubstituted by C$_1$-C$_{10}$-alkyl;

(B8) a naphthalene monoimide compound of formula (X)

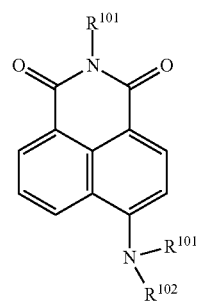
(X)

wherein each R$^{101}$ independently of each other is hydrogen, C$_1$-C$_{30}$-alkyl, C$_2$-C$_{30}$-alkyl which is interrupted by one or more oxygen, C$_3$-C$_8$-cycloalkyl, C$_6$-C$_{10}$-aryl, heteroaryl, C$_6$-C$_{10}$-aryl-C$_1$-C$_{10}$-alkylene, where the aromatic ring in the three latter radicals is unsubstituted or mono- or polysubstituted by C$_1$-C$_{10}$-alkyl;

R$^{102}$ is hydrogen, C$_1$-C$_{30}$-alkyl, C$_2$-C$_{30}$-alkyl which is interrupted by one or more oxygen, C$_3$-C$_8$-cycloalkyl, C$_6$-C$_{10}$-aryl, heteroaryl, C$_6$-C$_{10}$-aryl-C$_1$-C$_{10}$-alkylene, where the aromatic ring in the three latter radicals is unsubstituted or mono- or polysubstituted by C$_1$-C$_{10}$-alkyl;

(B9) 7-(diethylamino)-3-(5-methylbenzo[d]oxazol-2-yl)-2H-chromen-2-one;

(B10) a perylene compound of formulae (XIA) or (XIB)

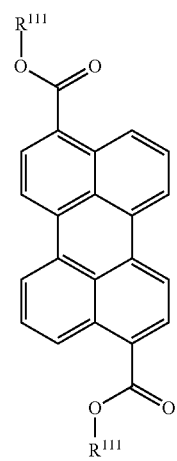
(XIA)

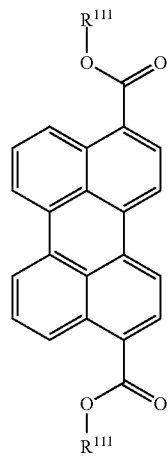
(XIB)

wherein each R$^{111}$ independently of each other is C$_1$-C$_{18}$ alkyl, C$_4$-C$_8$ cycloalkyl, which may be mono- or polysubstituted by halogen or by linear or branched C$_1$-C$_{18}$ alkyl, or phenyl or naphthyl which may be mono- or polysubstituted by halogen or by linear or branched C$_1$-C$_{18}$ alkyl;

and mixtures thereof;

(B11) a cyanated perylene compound of formulae (XIIA) or (XII B)

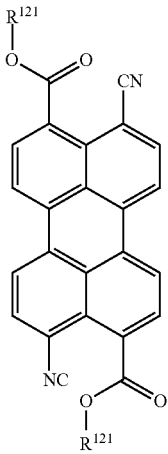
(XIIA)

-continued

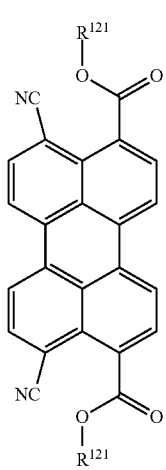

(XIIB)

wherein
each $R^{121}$ independently of each other is $C_1$-$C_{18}$ alkyl, $C_4$-$C_8$ cycloalkyl, which may be mono- or polysubstituted by halogen or by linear or branched $C_1$-$C_{18}$ alkyl, or phenyl or naphthyl which may be mono- or polysubstituted by halogen or by linear or branched $C_1$-$C_{18}$ alkyl;
and mixtures thereof;
(B12) a naphthoylbenzimidazole compound of formula (XIII)

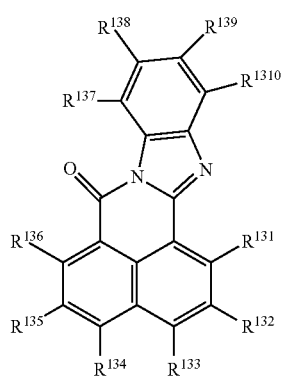

(XIII)

wherein
at least one of the radicals $R^{131}$, $R^{132}$, $R^{133}$, $R^{134}$, $R^{135}$, $R^{136}$, $R^{137}$, $R^{138}$, $R^{139}$ and $R^{1310}$ independently of each other is aryl which carries one, two or three cyano groups and 0, 1, 2, 3 or 4 substituents $R^{Ar13}$ and the remaining radicals $R^{131}$, $R^{132}$, $R^{133}$, $R^{134}$, $R^{135}$, $R^{136}$, $R^{137}$, $R^{138}$, $R^{139}$ and $R^{1310}$ independently of each other are selected from hydrogen and aryl which is unsubstituted or carries 1, 2, 3, 4 or 5 substituents $R^{Ar13}$, where
$R^{Ar13}$ independently of each other and independently of each occurrence is selected from halogen, $C_1$-$C_{30}$-alkyl, $C_2$-$C_{30}$-alkenyl, $C_2$-$C_{30}$-alkynyl, where the three latter radicals are unsubstituted or carry one or more $R^{13a}$ groups, $C_3$-$C_8$-cycloalkyl, 3- to 8-membered heterocyclyl, where the two latter radicals are unsubstituted or carry one or more $R^{13b}$ groups, aryl and heteroaryl, where the two latter radicals are unsubstituted or carry one or more $R^{13c}$ groups, where
$R^{13a}$ independently of each other and independently of each occurrence is selected from cyano, halogen, $C_3$-$C_8$-cycloalkyl, 3- to 8-membered heterocyclyl, aryl and heteroaryl, where $C_3$-$C_8$-cycloalkyl, 3- to 8-membered heterocyclyl are unsubstituted or bear one or more $R^{13b1}$ groups, and where aryl and heteroaryl are unsubstituted or bear one or more $R^{13c1}$ groups;
$R^{13b}$ independently of each other and independently of each occurrence is selected from cyano, halogen, $C_1$-$C_{18}$-alkyl, $C_3$-$C_8$-cycloalkyl, 3- to 8-membered heterocyclyl, aryl and heteroaryl, where $C_3$-$C_8$-cycloalkyl, 3- to 8-membered heterocyclyl are unsubstituted or bear one or more $R^{13b1}$ groups, and where aryl and heteroaryl are unsubstituted or bear one or more $R^{13c1}$ groups;
$R^{13c}$ independently of each other and independently of each occurrence is selected from cyano, halogen, $C_1$-$C_{18}$-alkyl, $C_3$-$C_8$-cycloalkyl, 3- to 8-membered heterocyclyl, aryl and heteroaryl, where $C_3$-$C_8$-cycloalkyl, 3- to 8-membered heterocyclyl are unsubstituted or bear one or more $R^{13b}1$ groups, and where aryl and heteroaryl are unsubstituted or bear one or more $R^{13c1}$ groups;
$R^{13b1}$ independently of each other and independently of each occurrence is selected from halogen, $C_1$-$C_{18}$-alkyl and $C_1$-$C_{18}$-haloalkyl,
$R^{13c1}$ independently of each other and independently of each occurrence is selected from halogen, $C_1$-$C_{18}$-alkyl and $C_1$-$C_{18}$-haloalkyl;
and mixtures thereof;
(B13) a perylene compound of formula (XIV)

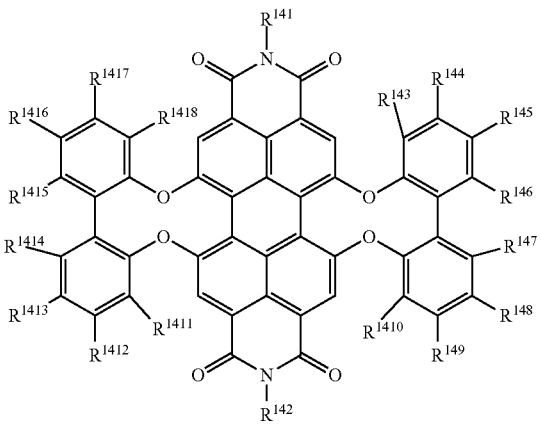

(XIV)

wherein
$R^{141}$ and $R^{142}$, independently of each other, are selected from hydrogen, in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkyloxy, $C_6$-$C_{24}$-aryl and $C_6$-$C_{24}$-aryloxy;
$R^{143}$, $R^{144}$, $R^{145}$, $R^{146}$, $R^{147}$, $R^{148}$, $R^{149}$, $R^{1410}$, $R^{1411}$, $R^{1412}$, $R^{1413}$, $R^{1414}$, $R^{1415}$, $R^{1416}$, $R^{1417}$ and $R^{1418}$ independently of each other, are selected from hydrogen, halogen, cyano, hydroxyl, mercapto, nitro, —$NE^{141}E^{142}$, —$NR^{Ar141}COR^{A142}$, —$CONR^{Ar141}R^{Ar142}$, —$SO_2NR^{A141}R^{A142}$, —$COOR^{Ar141}$, —$SO_3R^{Ar142}$ in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkoxy, $C_6$-$C_{24}$-aryl, $C_6$-$C_{24}$-aryloxy and $C_6$-$C_{24}$-arylthio, where $R^{143}$ and $R^{144}$, $R^{144}$ and $R^{145}$, $R^{145}$ and $R^{146}$, $R^{146}$ and $R^{147}$, $R^{147}$ and $R^{148}$, $R^{148}$ and $R^{149}$, $R^{149}$ and $R^{1410}$, $R^{1411}$ and $R^{1412}$, $R^{1412}$ and $R^{1413}$, $R^{1413}$ and $R^{1414}$, $R^{1414}$ and $R^{1415}$, $R^{1415}$ and $R^{1416}$, $R^{1416}$ and $R^{1417}$ and/or $R^{1417}$ and $R^{1418}$ together with the carbon atoms of the biphenylyl moiety to which they are bonded, may also form a further fused aromatic or non-aromatic ring system wherein the fused ring system is unsubstituted or substituted;

where $E^{141}$ and $E^{142}$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl;

$R^{Ar141}$ and $R^{Ar142}$, each independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl;

and mixtures thereof;

(B14) a perylene bisimide compound of formula (XV) different from compound (I)

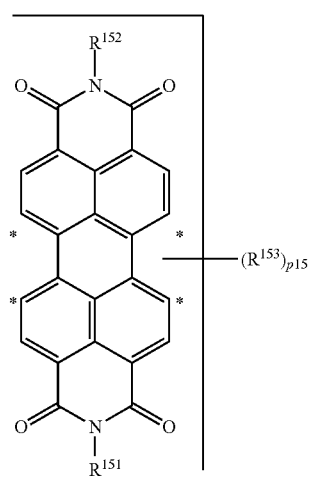

(XV)

wherein p15 is 1, 2, 3 or 4;

$R^{151}$ and $R^{152}$ independently of each other are $C_1$-$C_{10}$-alkyl, which is unsubstituted or substituted by $C_6$-$C_{10}$-aryl which in turn is unsubstituted or substituted by 1, 2 or 3 $C_1$-$C_{10}$-alkyl, $C_2$-$C_{20}$-alkyl, which is interrupted by one or more oxygen, $C_3$-$C_8$-cycloalkyl, which is unsubstituted or substituted by 1, 2 or 3 $C_1$-$C_{10}$-alkyl, or $C_6$-$C_{10}$-aryl which is unsubstituted or substituted by 1, 2 or 3 $C_1$-$C_{10}$-alkyl;

each $R^{153}$ independently of each other is fluorine, chlorine, $C_1$-$C_{16}$-alkyl, $C_2$-$C_{16}$-alkyl interrupted by one or more oxygen, $C_1$-$C_{16}$-alkoxy, $C_6$-$C_{10}$-aryloxy which is unsubstituted or mono- or polysubstituted by fluorine, chlorine, $C_1$-$C_{16}$-alkyl, $C_2$-$C_{16}$-alkyl interrupted by one or more oxygen, $C_1$-$C_{16}$-alkoxy or $C_6$-$C_{10}$-aryl, which is unsubstituted or substituted by 1, 2 or 3 radicals selected from $C_1$-$C_6$-alkyl, $C_1$-$C_6$-alkoxy-$C_1$-$C_6$-alkyl and $C_1$-$C_6$-alkoxy, where the $R^{133}$ radicals are at the positions indicated by *;

and mixtures thereof.

Organic Fluorescent Colorant (B1)

Cyanated naphthoylbenzimidazole compounds of formula (II) are known from WO2015/019270. Compounds of formula (II) are usually green, yellow-green or yellow fluorescent colorants. With regard to the use in the color converter of the present invention, the compound (11) is preferably selected from a compound of formula (II-A)

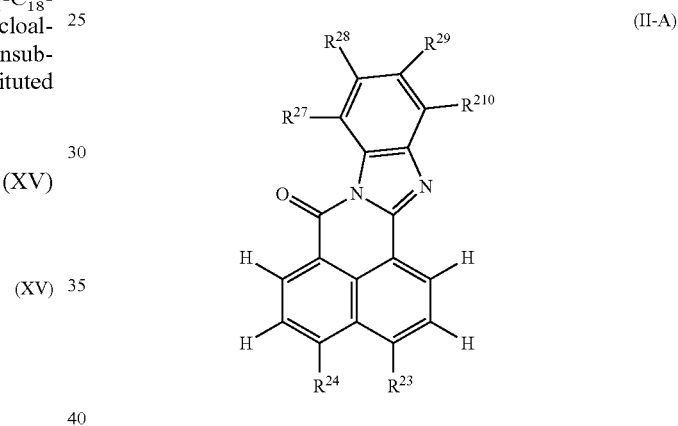

(II-A)

and mixtures thereof, in which $R^{23}$ and $R^{24}$ are each independently cyano, phenyl, 4-cyanophenyl or phenyl which carries 1, 2 or 3 substituents selected from $C_1$-$C_{10}$-alkyl, especially cyano, phenyl or 4-cyanophenyl; and $R^{27}$, $R^{28}$, $R^{29}$ and $R^{210}$ are each independently hydrogen, cyano, phenyl, 4-cyanophenyl or phenyl which carries 1, 2 or 3 substituents selected from $C_1$-$C_{10}$-alkyl, especially hydrogen, cyano, phenyl or 4-cyanophenyl.

More preferred are the compounds specified in WO 2015/019270 on page 16, 2$^{nd}$ paragraph to page 20, 3$^{rd}$ paragraph. With regard to the use in the color converter of the present invention, especially preferred are compounds of formula (II) selected from compounds of formulae (II-1), (II-2), (II-3), (II-4), (II-5), (II-6), (II-7), (II-8), (II-9), (II-10), (II-11), (II-12), (II-13), (II-14), (II-15), (II-16), (II-17), (II-18), (II-19), (II-20), (II-21), (II-22), (II-23), (II-24), (II-25), (II-26), (II-27), (II-28), (II-29), (II-30), (II-31), (II-32), (II-33), (II-34), (II-35), (II-36), (II-37), (II-38), (II-39), (II-40), (II-41), (II-42), (II-43), (II-44), (II-45), (II-46), (II-47), (II-48), (II-49), and (II-50) and mixtures thereof (II-1)
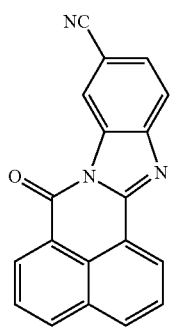
(II-2)
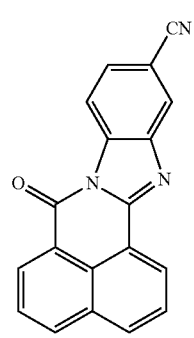
(II-3)
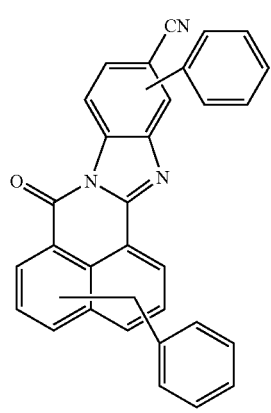
(II-4)
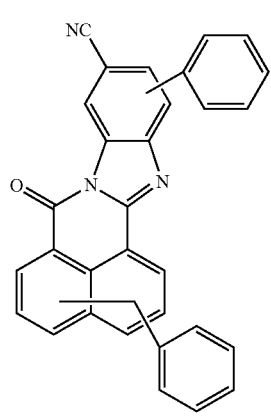
-continued
(II-5)
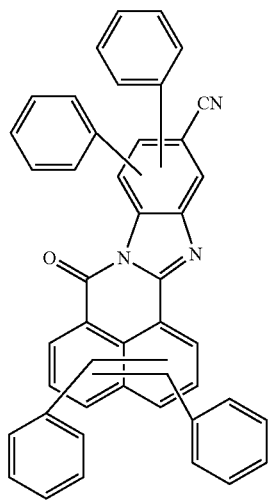
(II-6)
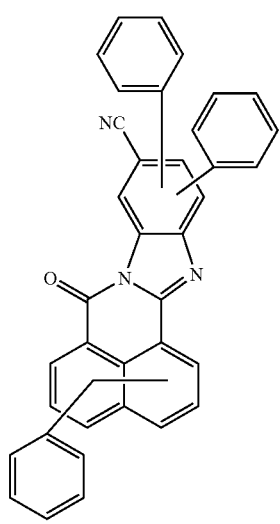
(II-7)
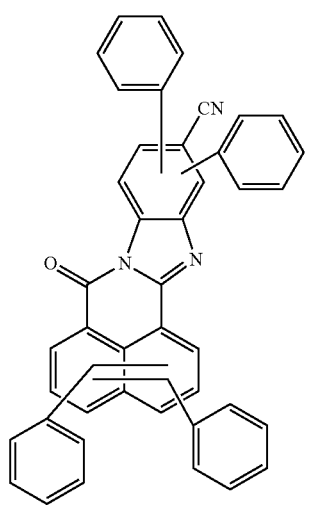

(II-8)
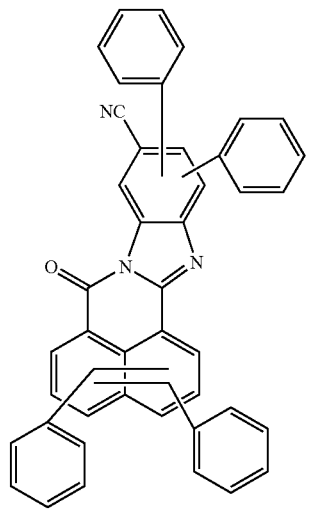
(II-9)
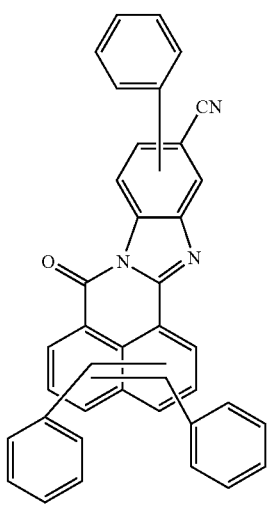
(II-10)
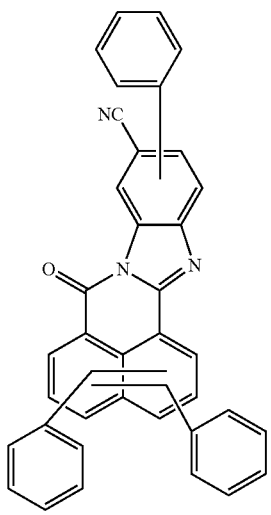
(II-11)
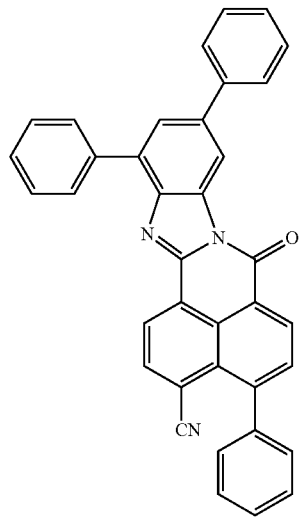
(II-12)
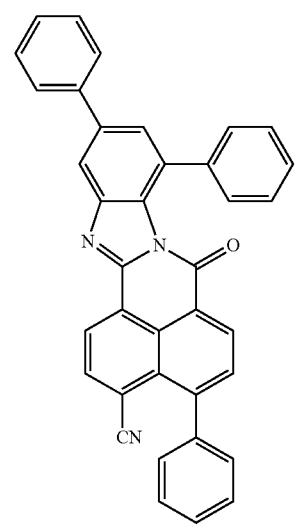
(II-13)
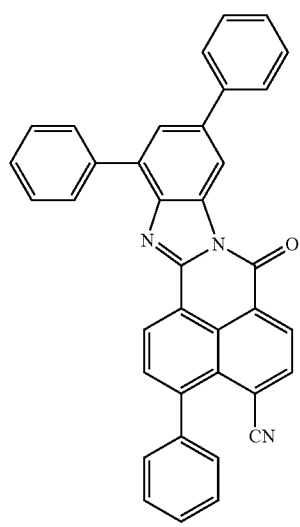

(II-14)
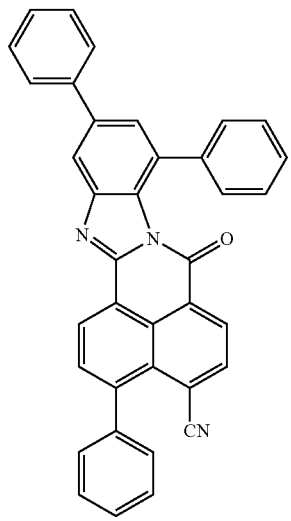
(II-15)
(II-16)
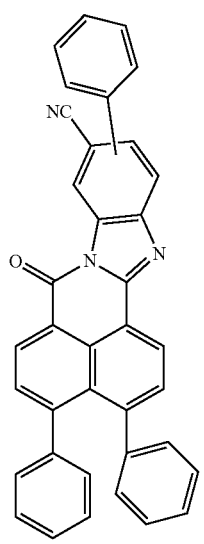
(II-17)
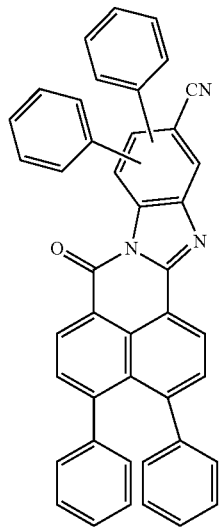
(II-18)
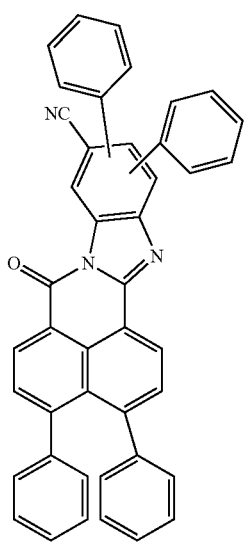
(II-19)
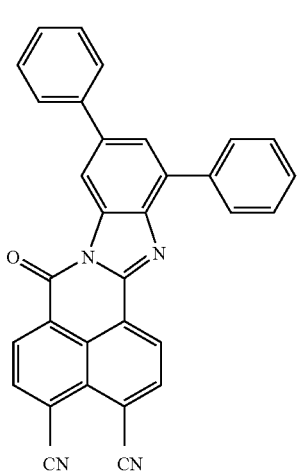

(II-20)
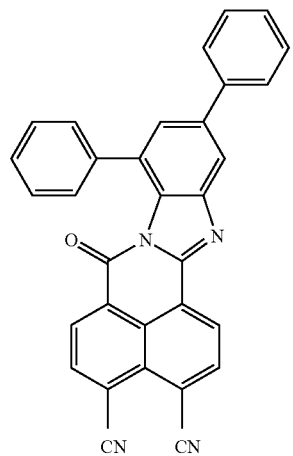
(II-21)
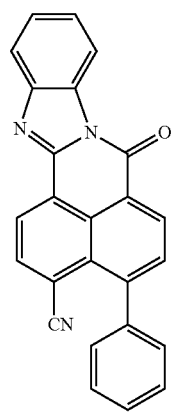
(II-22)
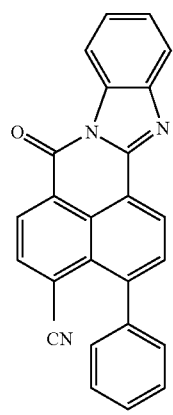
(II-23)
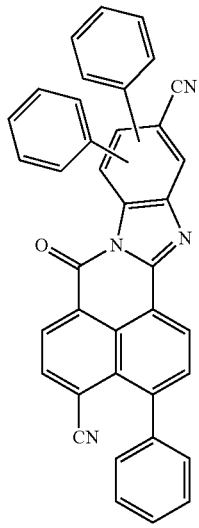
(II-24)
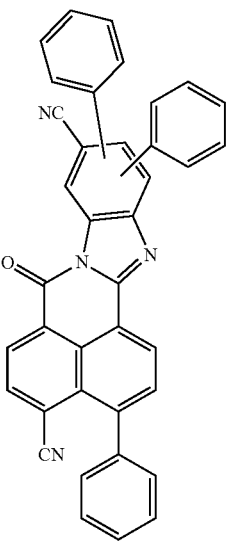
(II-25)
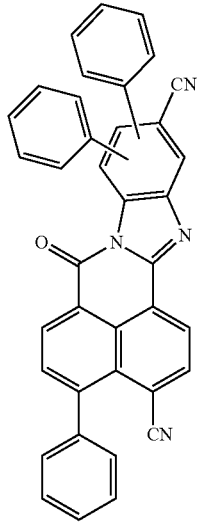

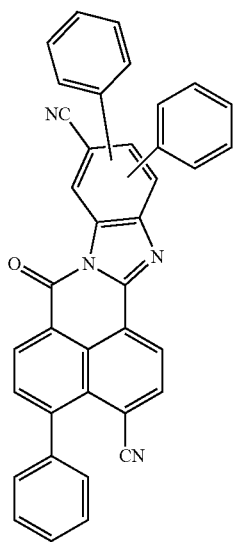
(II-26)
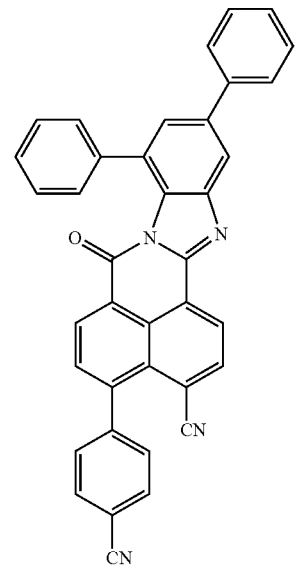
(II-28)
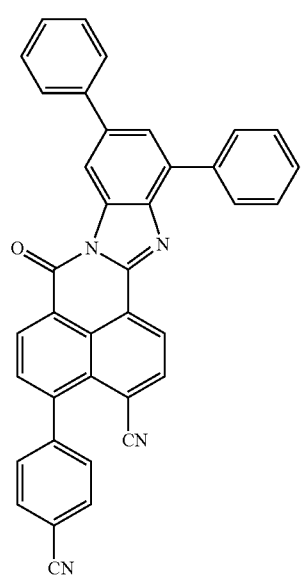
(II-27)
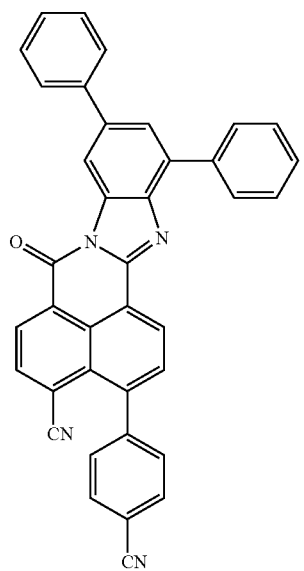
(II-29)

(II-30)

(II-31)

(II-32)

(II-33)

(II-34)

(II-35)

(II-36)
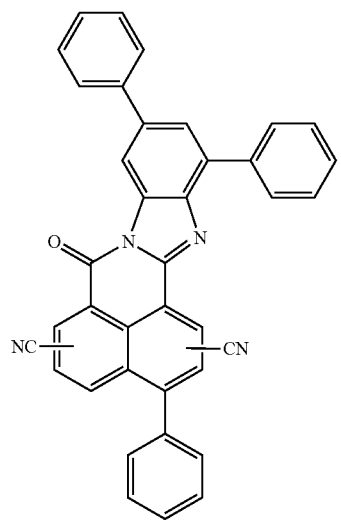
(II-37)
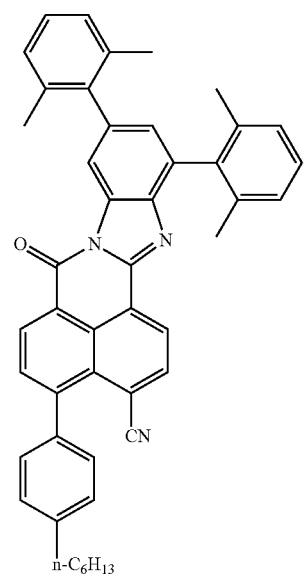
(II-38)
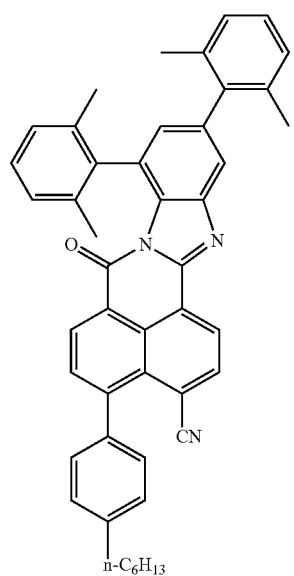
(II-39)
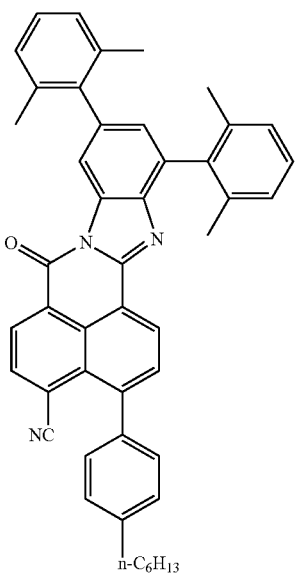
(II-40)
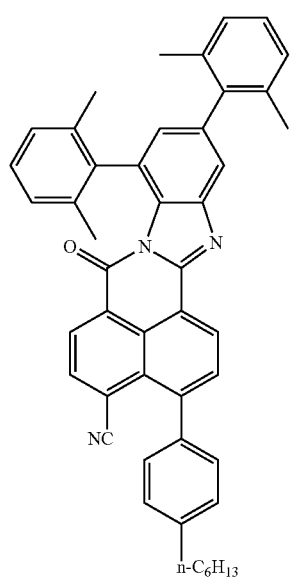
(II-41)
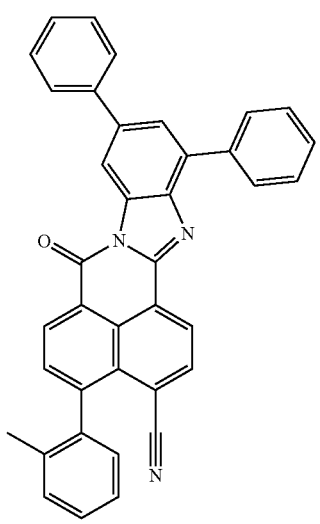

(II-42)
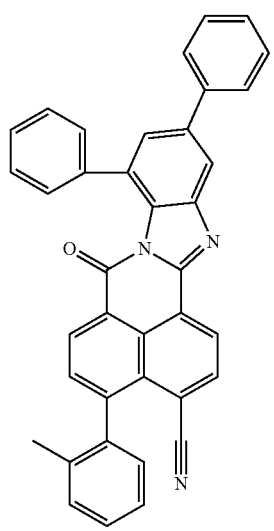
(II-43)
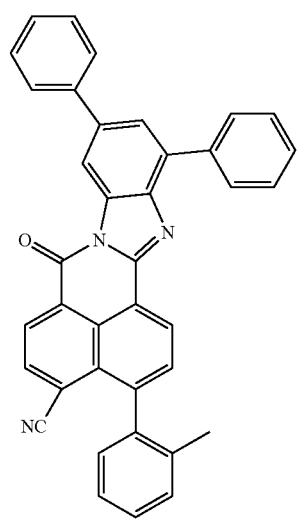
(II-44)
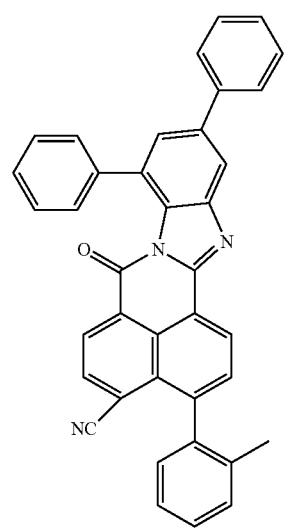
(II-45)
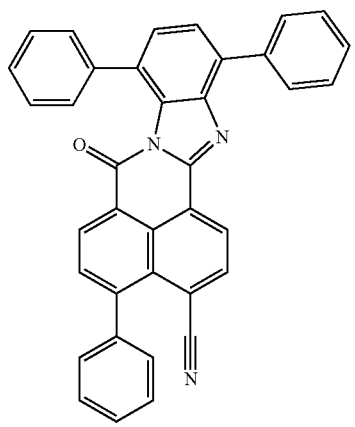
(II-46)
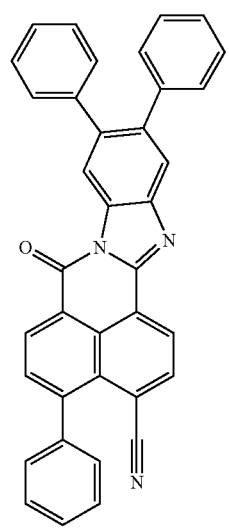
(II-47)
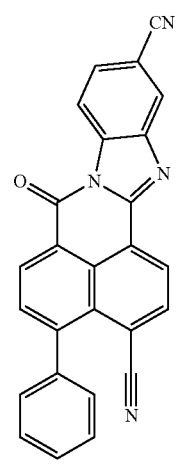

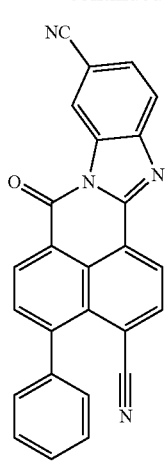

(II-48)

(II-49)

(II-50)

More especially preferred are compounds (II-11), (II-12), (II-13) and (II-14) and mixtures thereof.

Organic Fluorescent Colorant (B2)

Compounds of formula (III) are known from WO 2015/169935. Compounds of formula (III) are usually yellow or yellow-green fluorescent colorants. With regard to the use in the color converter of the present invention, the compound of formula (III) encompasses the following compounds of formulae (III-a) and (III-b) as well as compounds of formulae (III-c) and (IIII-d):

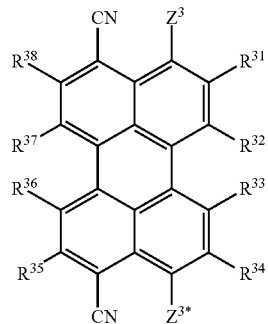

(III-a)

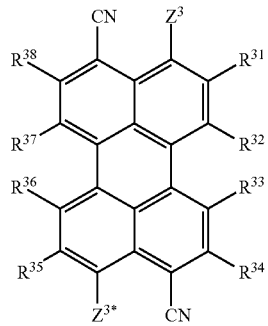

(III-b)

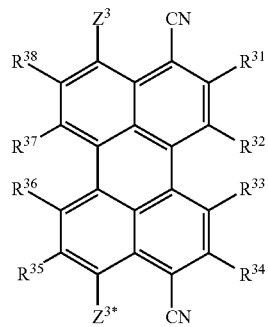

(III-c)

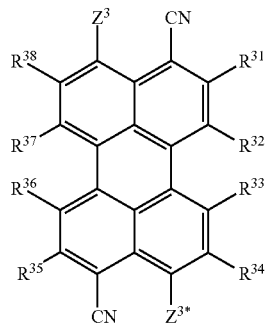

(III-d)

individually and mixtures thereof, in which $R^{31}$, $R^{32}$, $R^{33}$, $R^{34}$, $R^{35}$, $R^{36}$, $R^{37}$, $R^{38}$, $Z^3$ and $Z^{3*}$ are each as defined above.

In particular, preference is given to the compounds specified in WO 2015/169935 on page 12, line 9 to page 13, line 31. With regard to the use in the color converter of the present invention, preferred are compounds of formula (III) selected from compounds of formulae (III-1), (III-2), (III-3), (III-4), (III-5), (III-6), (III-7), (III-8), (III-9), (III-10), (III-11), (III-12), (III-13), (III-14), (III-15), (III-16), (III-17), (III-18), (III-19), (III-20)
(III-1)
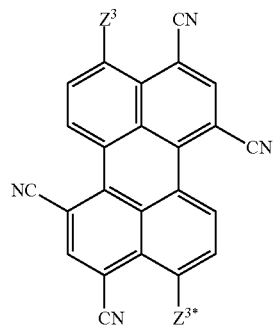
(III-2)
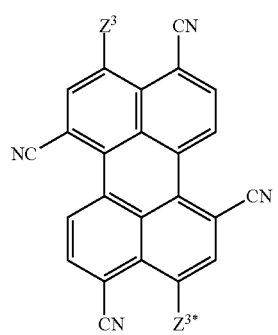
(III-3)
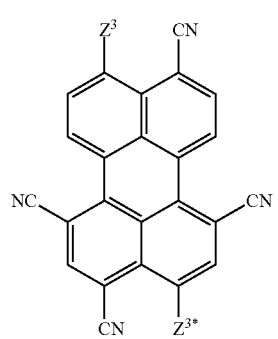
(III-4)
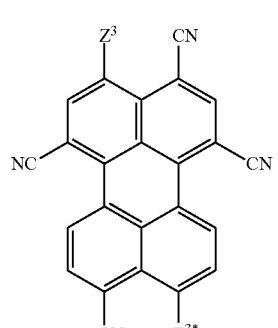
-continued
(III-5)
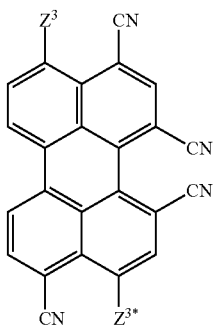
(III-6)
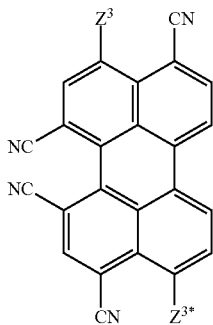
(III-7)
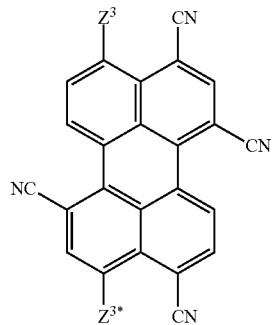
(III-8)
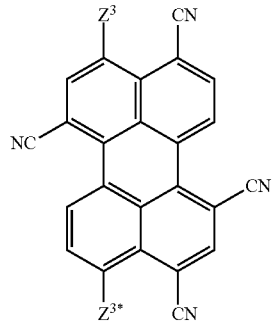
(III-9)
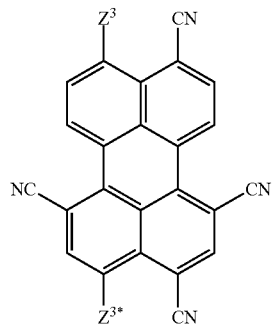

(III-10)
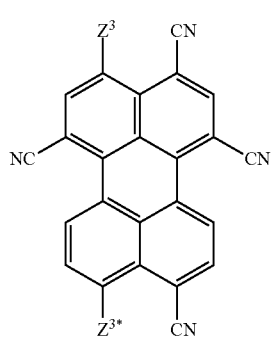
(III-11)
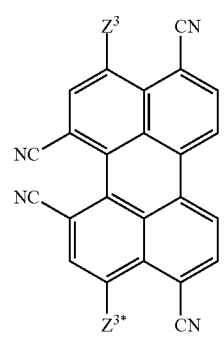
(III-12)
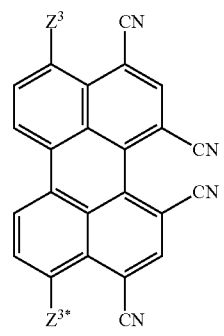
(III-13)
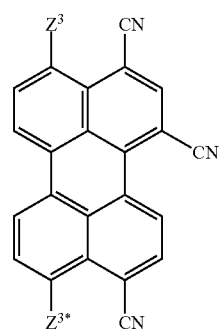
(III-14)
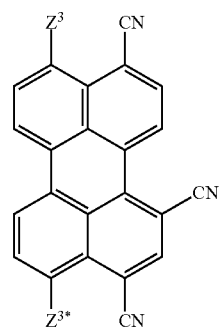
(III-15)
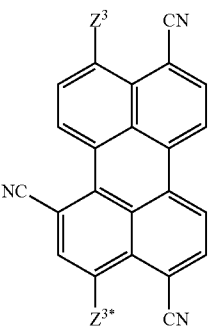
(III-16)
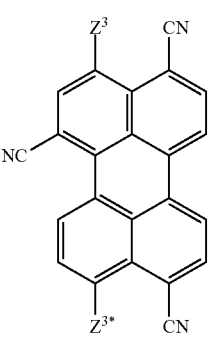
(III-17)
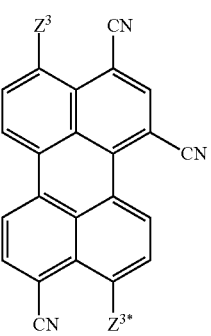
(III-18)
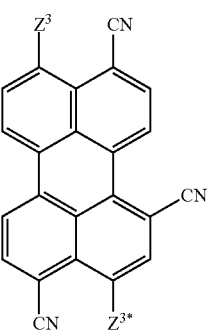
(III-19)
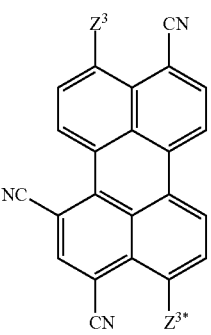

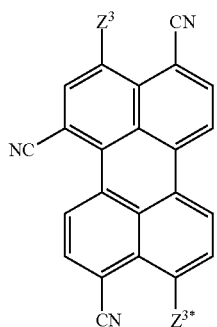

(III-20)

and mixtures thereof,
in which
$Z^3$ is selected from $C_1$-$C_6$-alkyl, $C_1$-$C_6$-alkoxycarbonyl, phenyl, and phenyl bearing 1, 2 or 3 $C_1$-$C_4$-alkyl groups; and
$Z^{3*}$ is selected from $C_1$-$C_6$-alkyl, $C_1$-$C_6$-alkoxycarbonyl, phenyl, and phenyl bearing 1, 2 or 3 $C_1$-$C_4$-alkyl groups.

In a special embodiment $Z^{3*}$ has the same meaning as $Z^3$.

Among these, specific preference is given to perylene compounds of formulae (10.a), (10.b)

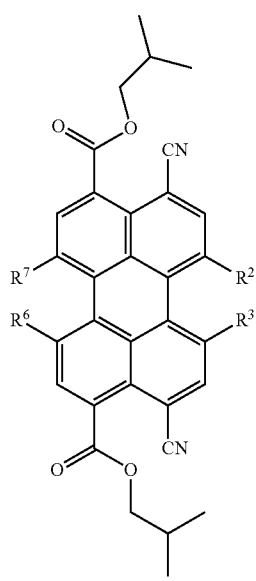

(10.a)

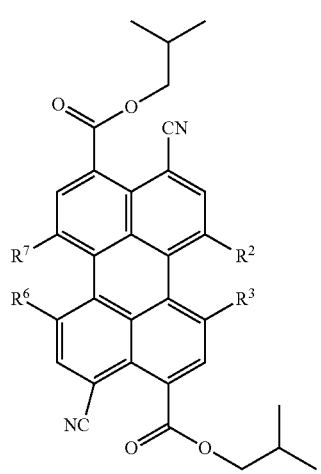

(10.b)

and mixtures thereof in which
three of the $R^2$, $R^3$, $R^6$ and $R^7$ substituents are hydrogen; and one of the $R^2$, $R^3$, $R^6$ and $R^7$ substituents is cyano.

Organic Fluorescent Colorant (B3)

Cyanated compounds of formula (IV) are subject-matter of WO 2016/151068. Compounds of formula (IV) are usually yellow or yellow-green fluorescent colorants. With regard to the use in the color converter of the present invention, the compound of formula (IV) is preferably a compound, wherein $X^{40}$ is O. Also preferred are compounds of formula (IV), wherein $X^{40}$ is S. Preferrence is given to the compounds specified in WO 2016/151068 on page 24, line 10 to page 34, line 4.

Among these, compounds of formula (IV) are especially preferred, wherein A is a radical of formula (A.2). Compounds of formula (IV), where A is a radical of formula (A.2) are also referred to as compounds of formula (IV-A.2),

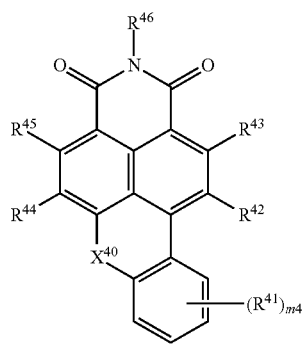

(IV-A.2)

wherein
m4, $X^{40}$, $R^{41}$, $R^{42}$, $R^{43}$, $R^{44}$, $R^{45}$ and $R^{46}$ are as defined above.

In the compounds of formula (I-A.2), $R^{46}$ is preferably selected from hydrogen, linear $C_1$-$C_{24}$-alkyl, branched $C_3$-$C_{24}$-alkyl, $C_6$-$C_{10}$-aryl and $C_6$-$C_{10}$-aryl-$C_1$-$C_{10}$-alkylene, where the aryl ring in the two last mentioned moieties is unsubstituted or substituted with 1, 2, 3, 4 or 5 identical or different radicals $R^{46a}$. Especially, $R^{46}$ is selected from linear $C_1$-$C_{24}$-alkyl, a radical of formula (B.1) and a radical of formula (B.2)

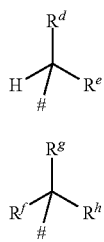

(B.1)

(B.2)

in which
# is the bonding site to the nitrogen atom;
$R^d$ and $R^e$, in the formula (B.1), independently from each other are selected from $C_1$-$C_{23}$-alkyl, where the sum of the carbon atoms of the $R^d$ and $R^e$ radicals is an integer from 2 to 23;
$R^f$, $R^g$ and $R^h$, in the formula (B.2) are independently selected from $C_1$- to $C_{20}$-alkyl, where the sum of the carbon atoms of the $R^f$, $R^g$ and $R^h$ radicals is an integer from 3 to 23.

Preferred radicals of formula (B.1) are: 1-methylethyl, 1-methylpropyl, 1-methylbutyl, 1-methylpentyl, 1-methylhexyl, 1-methylheptyl, 1-methyloctyl, 1-ethylpropyl, 1-ethylbutyl, 1-ethylpentyl, 1-ethylhexyl, 1-ethylheptyl, 1-ethyloctyl, 1-propylbutyl, 1-propylpentyl, 1-propylhexyl, 1-propylheptyl, 1-propyloctyl, 1-butylpentyl, 1-butylhexyl, 1-butylheptyl, 1-butyloctyl, 1-pentylhexyl, 1-pentylheptyl, 1-pentyloctyl, 1-hexylheptyl, 1-hexyloctyl, 1-heptyloctyl.

A particularly preferred radical of formula (B.2) is tert.-butyl.

Likewise especially, $R^{46}$ is a radical of formula (C.1), a radical of formula (C.2) or a radical of formula (C.3)

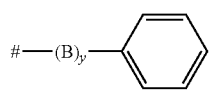

(C.1)

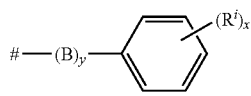

(C.2)

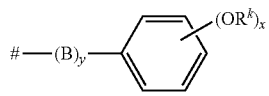

(C.3)

where
# represents the bonding side to the nitrogen atom,
B where present, is a $C_1$-$C_{11}$-alkylene group which may be interrupted by one or more nonadjacent groups selected from —O— and —S—,
y is 0 or 1,
$R^i$ is independently of one another selected from $C_1$-$C_{24}$-alkyl, $C_1$-$C_{24}$-fluoroalkyl, fluorine, chlorine or bromine, $R^k$ is independently of one another selected from $C_1$-$C_{24}$-alkyl,
x in formulae C.2 and C.3 is 1, 2, 3, 4 or 5.

Preferably, y is 0, i.e. the variable B is absent.

Irrespectively of its occurrence, $R^i$ is preferably selected from $C_1$-$C_{24}$-alkyl, more preferably linear $C_1$-$C_{10}$-alkyl or branched $C_3$-$C_{10}$-alkyl, especially isopropyl. Irrespectively of its occurrence, $R^k$ is preferably selected from linear $C_1$-$C_{10}$-alkyl or branched $C_3$-$C_{10}$-alkyl. The variable x in formulae (C.2) and (C.3) is preferably 1, 2 or 3.

A special group of embodiments relates to compounds of formula (IV-A.2), wherein the variables m4, $X^{40}$, $R^{41}$, $R^{42}$, $R^{43}$, $R^{44}$, and $R^{45}$ independently of each other or in particular in combination, have the following meanings:

$X^{40}$ is O or S;
$R^{42}$ and $R^{44}$ are each cyano;
$R^{43}$ and $R^{45}$ are each hydrogen or one of $R^{43}$ and $R^{45}$ is bromine and the other of $R^{43}$ and $R^{45}$ is hydrogen;
$R^{41}$ is selected from cyano, bromine, and phenyl which is unsubstituted or carries 1 or 2 radicals selected from $C_1$-$C_4$-alkyl;
$R^{46}$ is selected from hydrogen, $C_1$-$C_{24}$-linear alkyl, branched $C_3$-$C_{24}$-alkyl, a radical of formula (C.1), a radical of formula (C.2) and a radical of formula (C.3);
m4 is 0 or 1.

Even more preferably,
$X^{40}$ is O or S;
$R^{42}$ and $R^{44}$ are each cyano;
$R^{43}$ and $R^{45}$ are each hydrogen;
$R^{41}$ is selected from cyano, bromine, and phenyl which is unsubstituted or carries 1 or 2 radicals selected from $C_1$-$C_4$-alkyl; especially cyano;
$R^{46}$ is selected from linear $C_1$-$C_{24}$-alkyl, branched $C_3$-$C_{24}$-alkyl, a radical of formula (C.1), a radical of formula (C.2) and a radical of formula (C.3); especially linear $C_1$-$C_{24}$-alkyl, branched $C_3$-$C_{24}$-alkyl, or phenyl which carries 1 or 2 radicals selected from $C_1$-$C_4$-alkyl such as 2,6-diisopropylphenyl;
m4 is 0 or 1.

Examples for preferred compounds of formula (IV-A.2) are shown below:

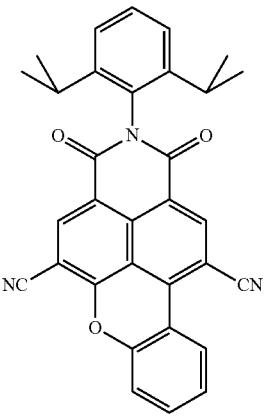

(IV-A.2-1)

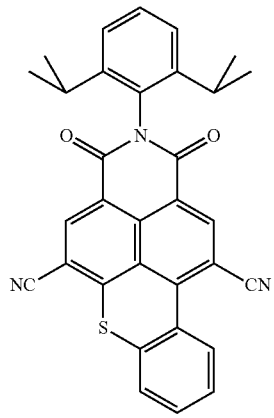 (IV-A.2-2)
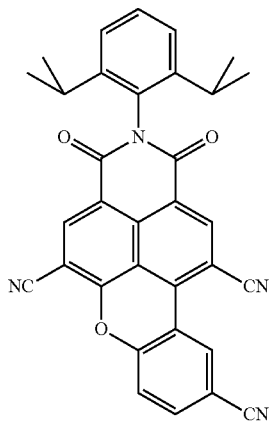 (IV-A.2-5)
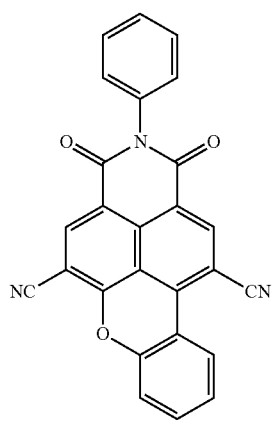 (IV-A.2-3)
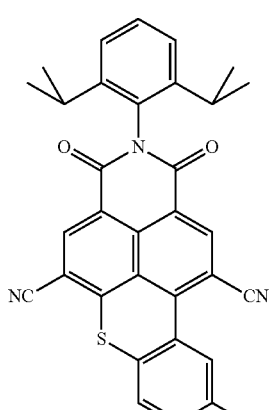 (IV-A.2-6)
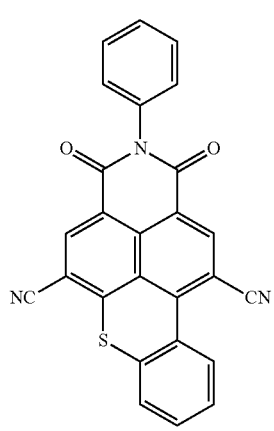 (IV-A.2-4)
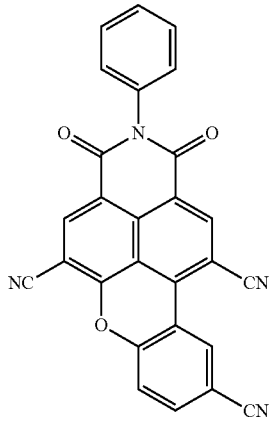 (IV-A.2-7)

(IV-A.2-8)
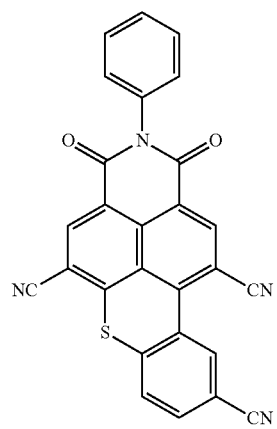
(IV-A.2-10)
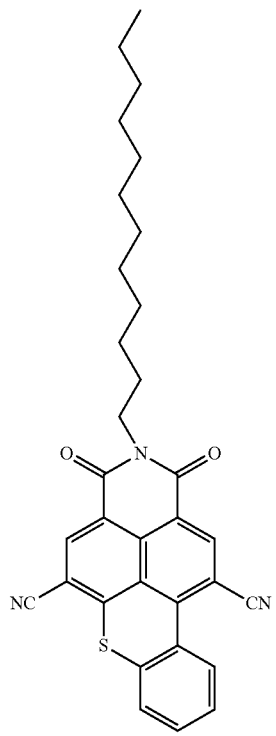
(IV-A.2-9)
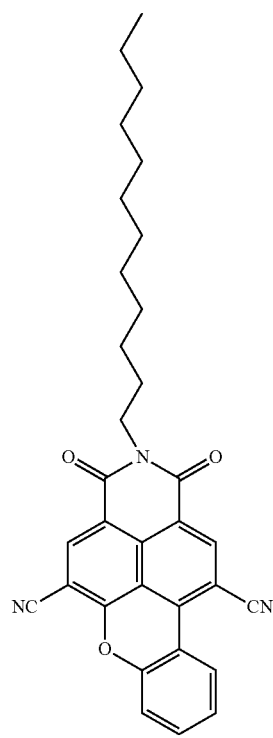
(IV-A.2-11)
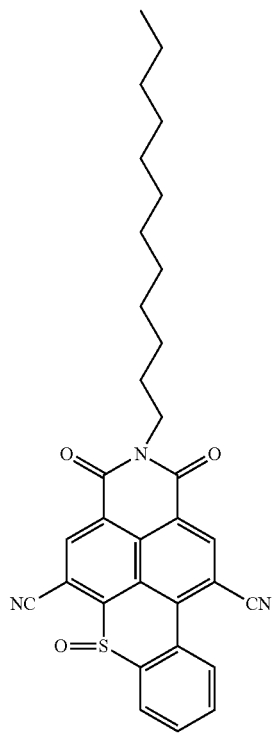

(IV-A.2-12)
(IV-A.2-14)
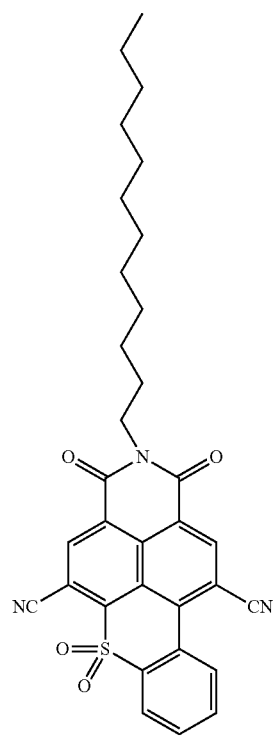
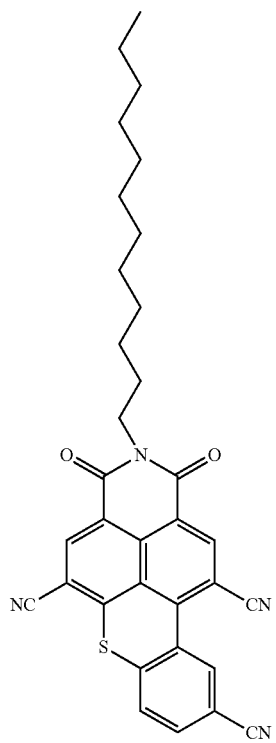
(IV-A.2-13)
(IV-A.2-15)

-continued (IV-A.2-16)

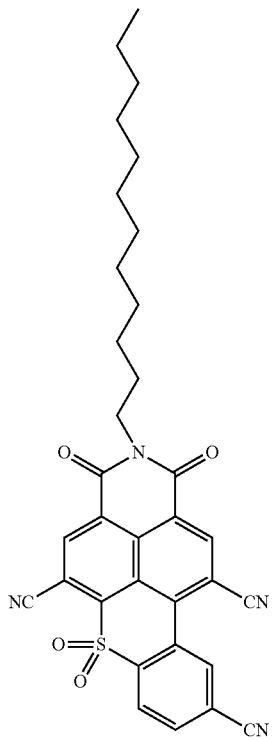

In particular, organic fluorescent colorant (B4) is selected from compounds IV-A.2-1, IV-A.2-6 and IV-A.2-9.

Organic Fluorescent Colorant (B4)

Benzoxanthene compounds of formula (V) are known from WO 2014/131628. They are usually yellow fluorescent. Suitable compounds are depicted in in FIG. 2A, FIG. 2B and FIG. 2C of WO 2014/131628. They are usually yellow or yellow-green fluorescent colorants. Benzothioxanthene compounds of formula (V) are known for example from U.S. Pat. No. 3,357,985. Preferred are benz(othi)oxanthene compounds of formula (V), wherein $X^5$ is O or S, $R^{51}$ is $C_1$-$C_{24}$-alkyl and $R^{52}$—$R^{59}$ are hydrogen. Preferably, $R^{51}$ is $C_6$-$C_{20}$-alkyl.

Organic Fluorescent Colorant (B5)

Benzimidazoxanthenisoquinoline compounds of formula (VIA) and (VIB) are known from WO 2015/062916. Suitable compounds are depicted at page 3, line 24 to page 8, line 24, especially FIG. 3A, FIG. 3B, FIG. 3C of WO 2015/062916.

Organic Fluorescent Colorant (B6)

Compounds having a structural unit of formula (VII) are known from WO 2012/168395. In general, they are yellow fluorescent colorants. With regard to the use in the color converter of the present invention, the compound having a structural unit of formula (VII) is preferably a compound as specified in WO 2012/168395, at page 28, line 14 to page 32, line 5.

With regard to the use in the colour converter of the present invention, the compound having a structural unit of formula (VII) is more preferably selected from compounds of formulae (VII-1), (VII-2), (VII-3), (VII-4), (VII-5), (VII-6), (VII-7), (VII-8), (VII-9), (VII-10), (VII-11), (VII-12), (VII-13), (VII-14), (VII-15), (VII-16), (VI-17), (VII-18), (VII-19), (VII-20), (VII-21), (VII-22), (VII-23), (VII-24), (VII-25), (VII-26), (VII-27), (VII-28), (VII-29), (VII-30), (VII-31), (VII-32), (VII-33), (VII-34), (VII-35), (VII-36), (VII-37), (VII-38), (VII-39), (VII-40), (VII-41), (VII-42), (VII-43), (VII-44), (VII-45), (VII-46), (VII-47), (VII-48), (VII-49), (VII-50), (VII-51), (VII-52), (VII-53), (VII-54), (VII-55), and mixtures thereof

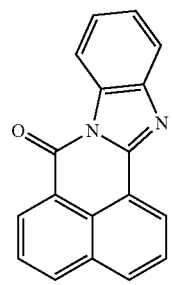

(VII-1)

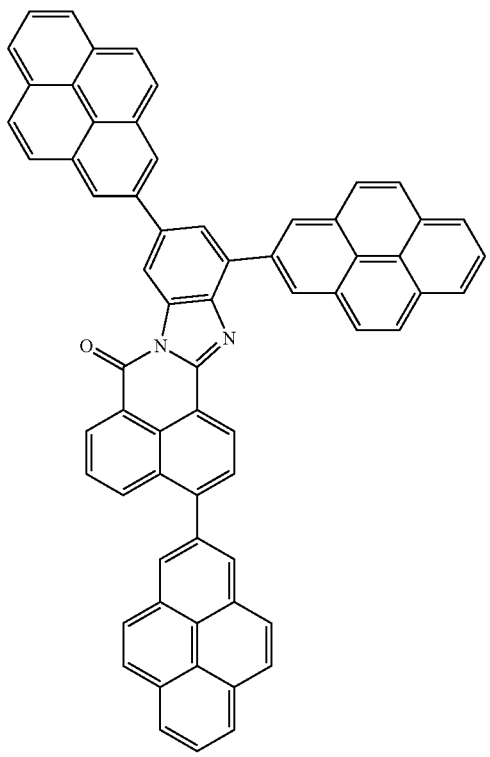

(VII-2)

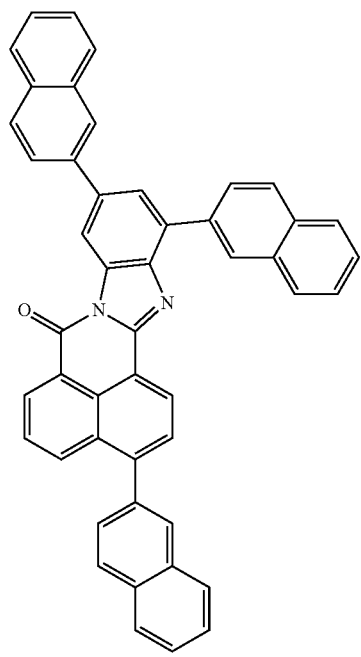
(VII-3)
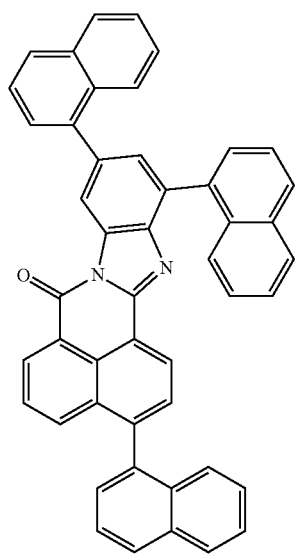
(VII-4)
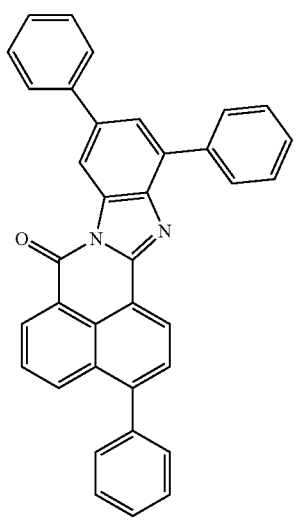
(VII-5)
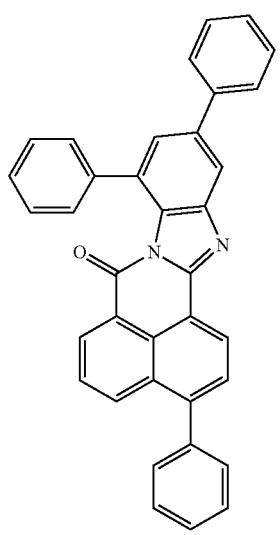
(VII-6)
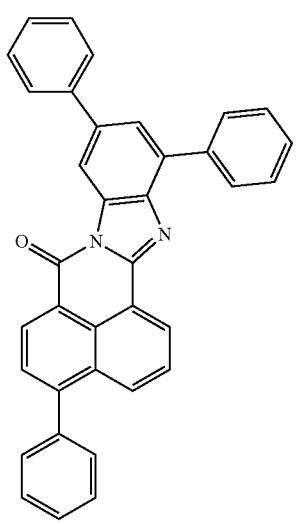
(VII-7)

(VII-8)
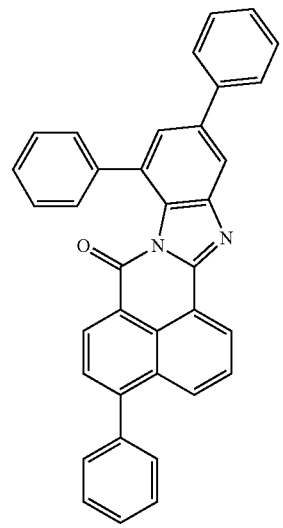
(VII-9)
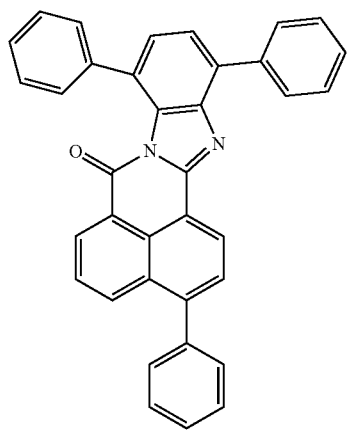
(VII-10)
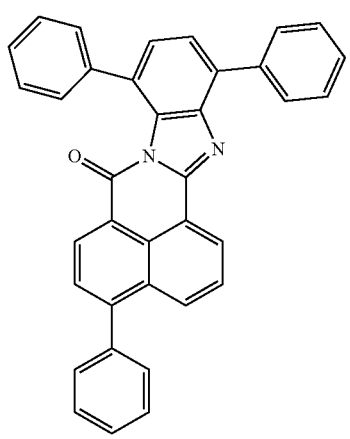
(VII-11)
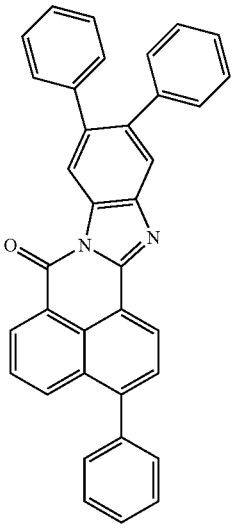
(VII-12)
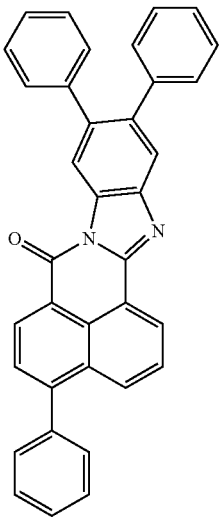
(VII-13)
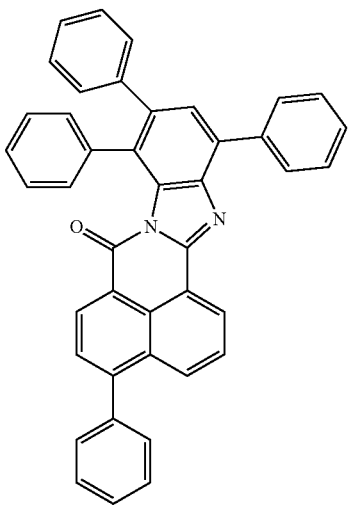

(VII-14)
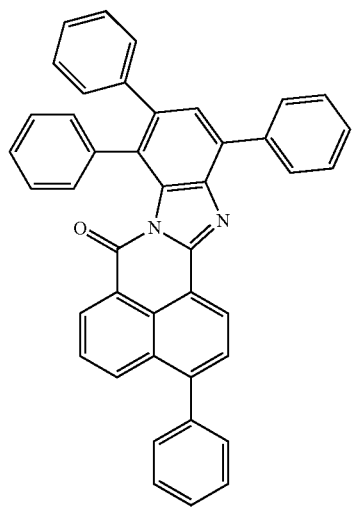
(VII-15)
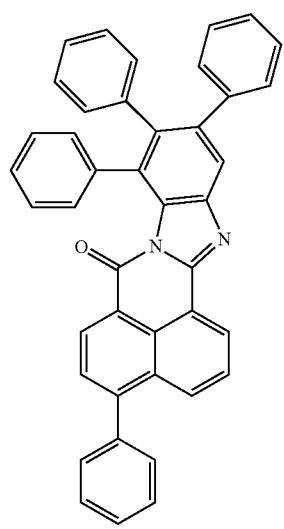
(VII-16)
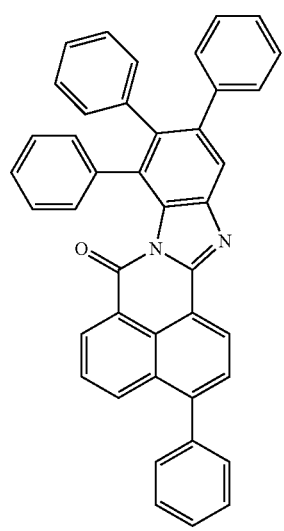
(VII-17)
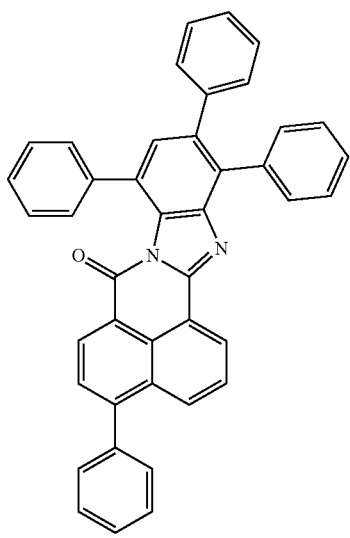
(VII-18)
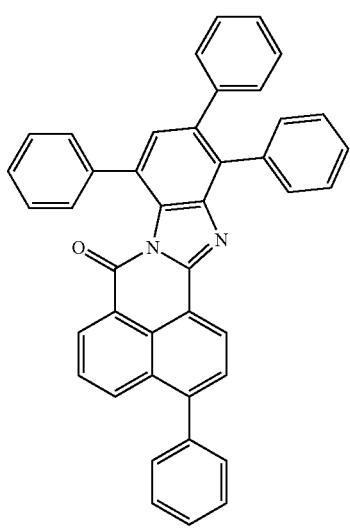
(VII-19)
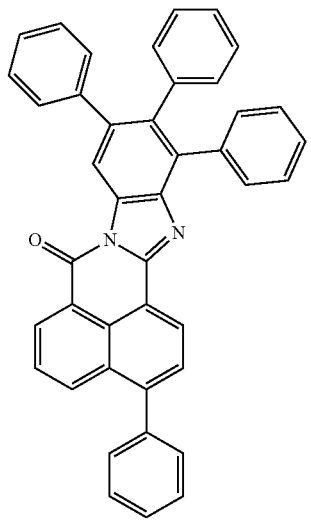

(VII-20)
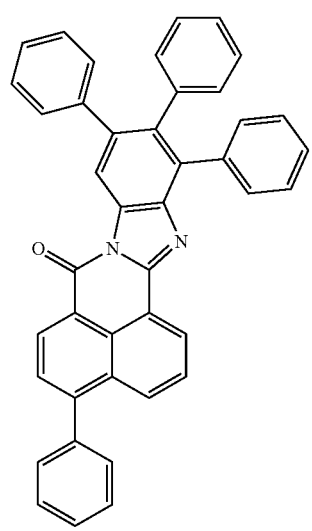
(VII-21)
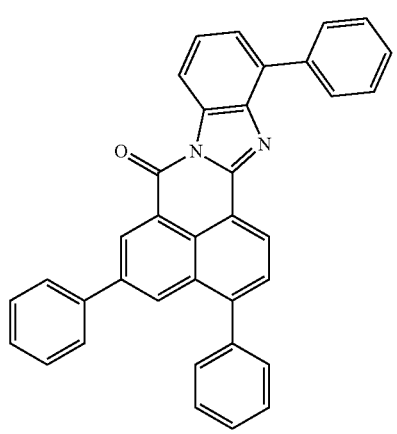
(VII-22)
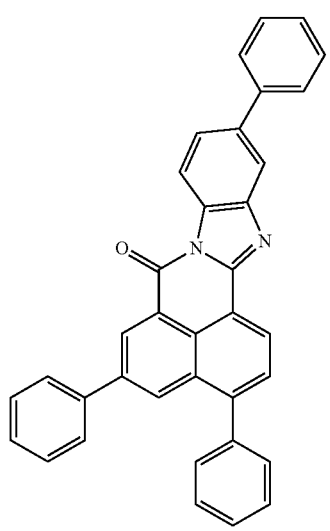
(VII-23)
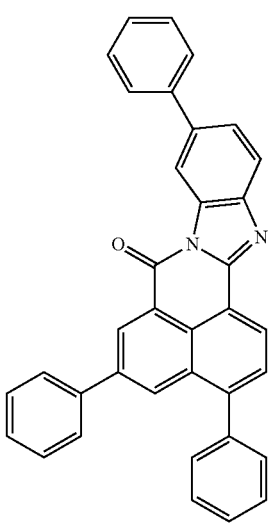
(VII-24)
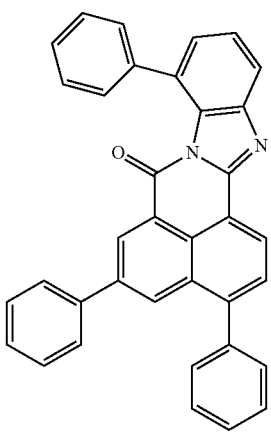
(VII-25)
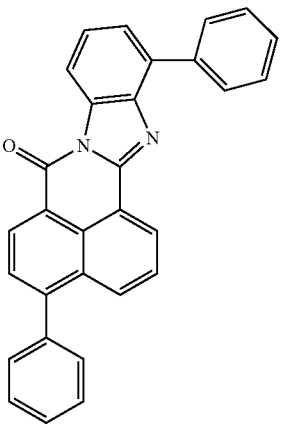

-continued
(VII-26)
(VII-27)
(VII-28)
(VII-29)
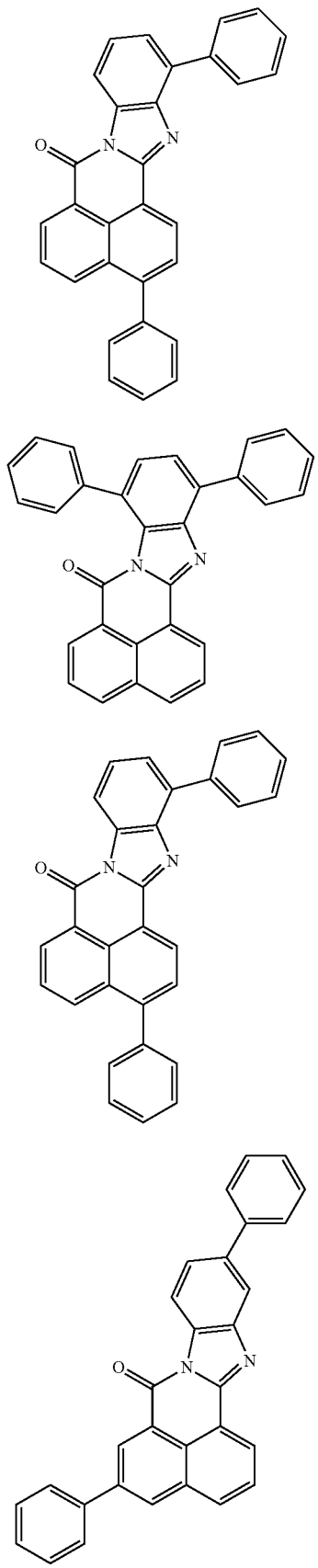
-continued
(VII-30)
(VII-31)
(VII-32)
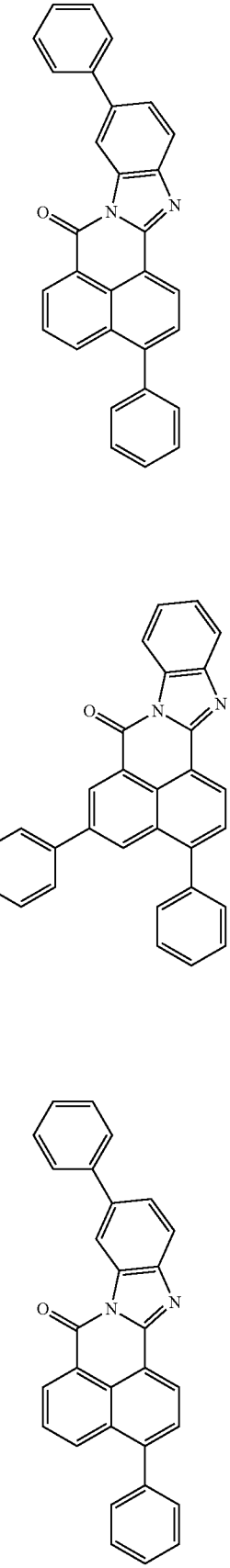

(VII-33)
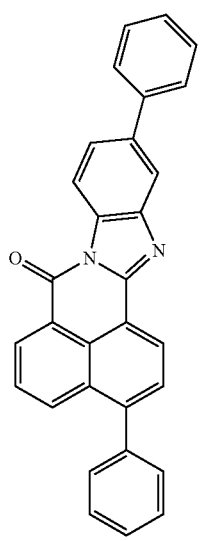
(VII-34)
(VII-35)
(VII-36)
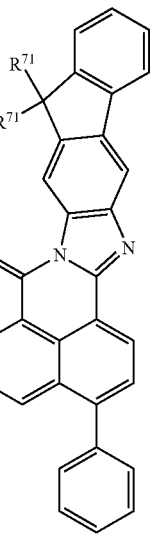
(VII-37)
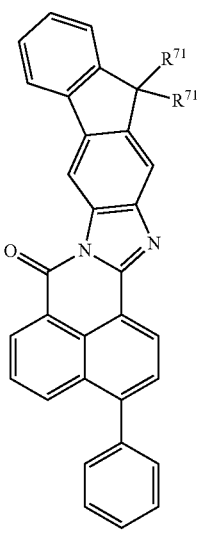
(VII-38)

(VII-39)
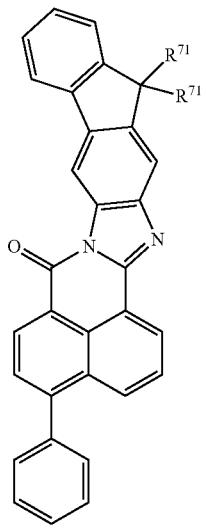
(VII-40)
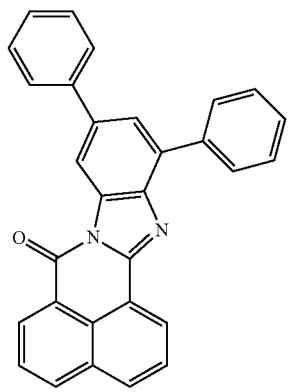
(VII-41)
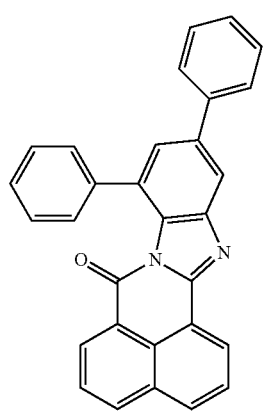
(VII-42)
(VII-43)
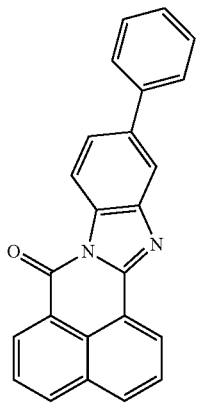
(VII-44)
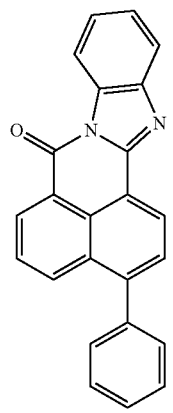
(VII-45)
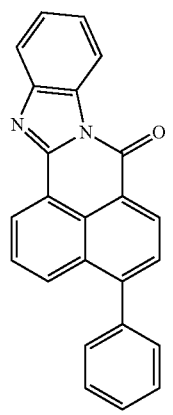

(VII-46)
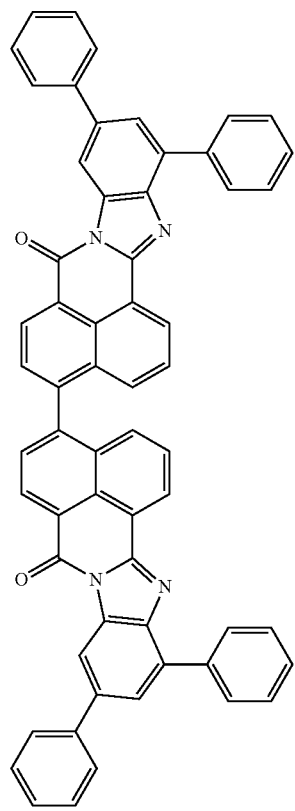
(VII-47)
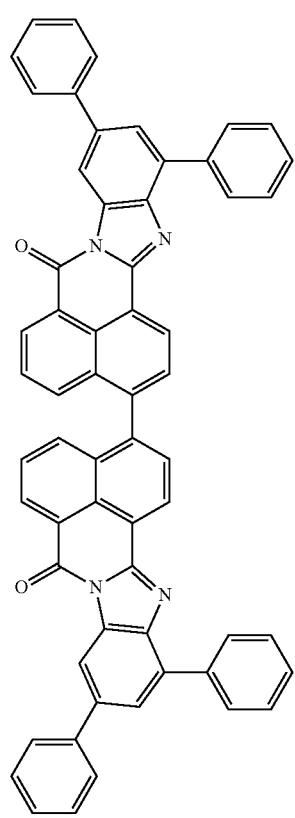
(VII-48)
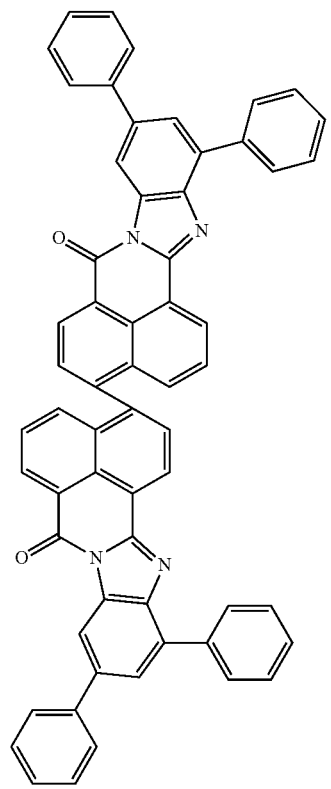
(VII-49)
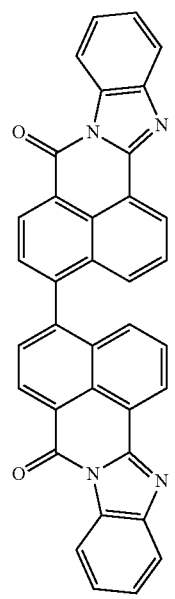

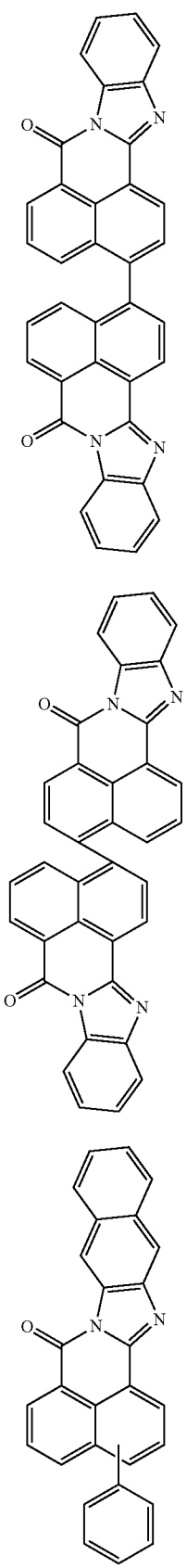
(VII-50)
(VII-51)
(VII-52)
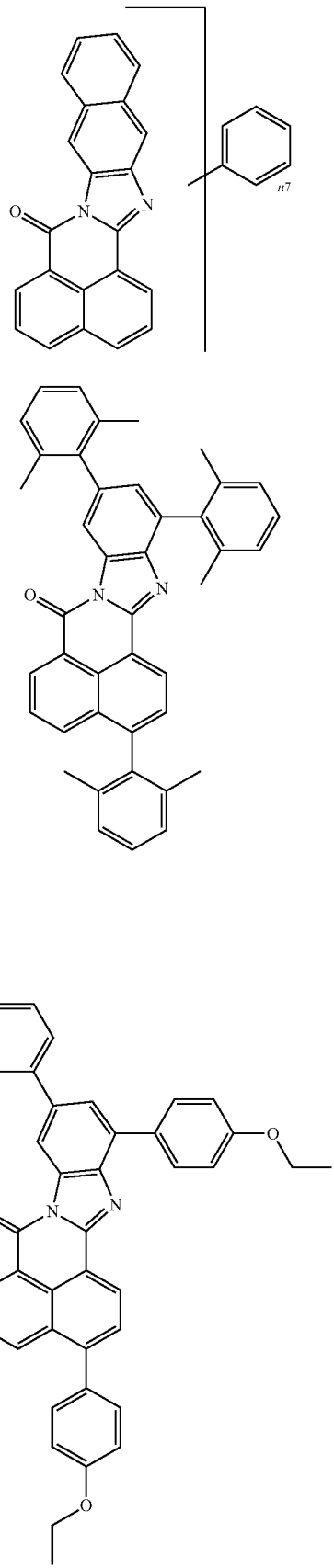
(VII-53)
(VII-54)
(VII-55)

(VII-56)

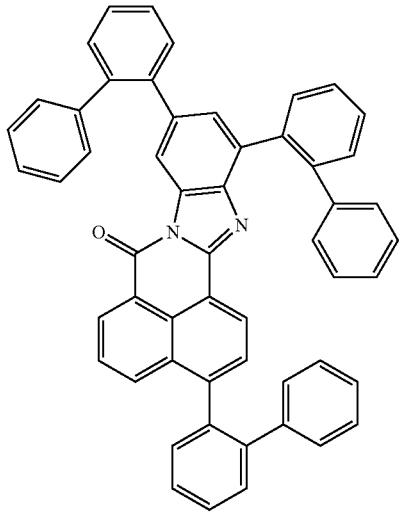

(VII-57)

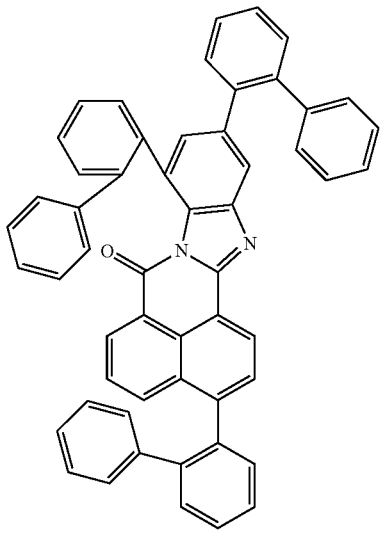

(VII-58)

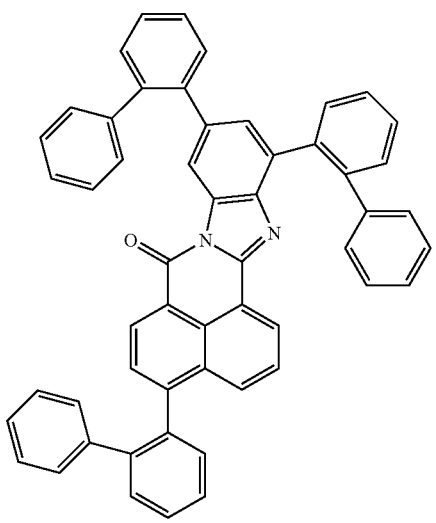

(VII-59)

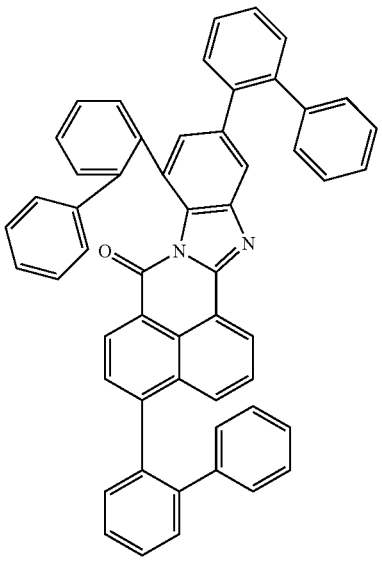

and mixtures thereof,
where n7 is a number from 0, 1, 2, 3, 4, 5, 6, 7, 8, 9 or 10;
$R^{71}$ is independently hydrogen, $C_1$-$C_{18}$-alkyl or cycloalkyl, the carbon chain of which may comprise one or more —O—, —S—, —CO—, —SO— and/or —SO$_2$-moieties and which may be mono- or polysubstituted;
aryl or heteroaryl which may be mono- or polysubstituted.
Especially preferred are the compounds of formulae (VII-5), (VII-6), (VII-7) and (VII-8) and mixtures thereof. Especially preferred are also the compounds of formulae (VII-56), (VII-57), (VII-58) and (VII-59) and mixtures thereof.

Organic Fluorescent Colorant (B7)

Perylene imide compounds of formula (VIII) and (IX) are well known in the art, e.g. from WO 2007/006717 or U.S. Pat. No. 6,472,050. 9-Cyano substituted perylene-3,4-dicarboxylic acid monoimides of formula (IX) are also known from WO 2004/029028. They are usually orange fluorescent colorants.

Preferably, in compounds of the formula (VIII), $R^{81}$ and $R^{82}$ are a linear or branched $C_1$-$C_{18}$ alkyl radical, a $C_4$-$C_8$ cycloalkyl radical which may be mono- or polysubstituted by halogen or by linear or branched $C_1$-$C_{18}$ alkyl, or phenyl or naphthyl which may be mono- or polysubstituted by halogen or by linear or branched $C_1$-$C_{18}$ alkyl.

Preferably, $R^{81}$ and $R^{82}$ have the same meaning.

In one embodiment, $R^{81}$ and $R^{82}$ in formula VIII represents compounds with what is called swallowtail substitution, as specified in WO 2009/037283 A1 at page 16 line 19 to page 25 line 8. In a preferred embodiment, $R^{81}$ and $R^{82}$, independently of each other, are a 1-alkylalkyl, for example 1-ethylpropyl, 1-propylbutyl, 1-butylpentyl, 1-pentylhexyl or 1-hexylheptyl.

In a specific embodiment, the organic fluorescent colorant (B7) is selected from compounds (VIII-1)

(VIII-1)

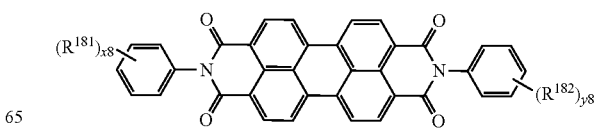

wherein
x8 is 1, 2 or 3;
y8 is 1, 2 or 3;
$R^{181}$ is $C_1$-$C_4$-alkyl; and
$R^{182}$ is $C_1$-$C_4$-alkyl.

Preferably, x8 is 2. Preferably, y8 is 2. Preferably, $R^{181}$ and $R^{182}$ are selected from isopropyl and tert-butyl.

A preferred compound of formula (VIII) is N,N'-bis(2,6-diisopropylphenyl)-3,4,9,10-perylenetetracarboxylic diimide (CAS-number: 82953-57-9).

Suitable 9-cyano substituted perylene-3,4-dicarboxylic acid monoimides of formula (IX) are preferably those, wherein $R^{92}$ is a linear or branched $C_1$-$C_{18}$ alkyl radical, a $C_4$-$C_8$ cycloalkyl radical which may be mono- or polysubstituted by halogen or by linear or branched $C_1$-$C_{18}$ alkyl, or phenyl or naphthyl which may be mono- or polysubstituted by halogen or by linear or branched $C_1$-$C_{18}$ alkyl.

In one embodiment, $R^{92}$ in formula IX represents compounds with what is called swallowtail substitution, as specified in WO 2009/037283 A1 at page 16 line 19 to page 25 line 8. In a preferred embodiment, $R^{92}$, is a 1-alkylalkyl, for example 1-ethylpropyl, 1-propylbutyl, 1-butylpentyl, 1-pentylhexyl or 1-hexylheptyl.

In a preferred embodiment, $R^{92}$ is 2,4-di(tert-butyl)phenyl 2,6-diisopropylphenyl or 2,6-di(tert-butyl)phenyl. In particular, $R^{92}$ is 2,6-diisopropylphenyl.

Organic Fluorescent Colorant (B8)

4-Amino-substituted naphthalimide compounds of formula (X) are known in the art. Suitable 4-amino substituted naphthalimide compounds of formula (X) are preferably those, wherein $R^{101}$ is linear or branched $C_1$-$C_{10}$-alkyl, $C_2$-$C_{10}$-alkyl which is interrupted by one or more oxygen, or $C_3$-$C_8$-cycloalkyl. $R^{102}$ is preferably hydrogen. A suitable compound of formula (X) is 4-(butylamino)-N-butyl-1,8-naphthalimide (CAS Number: 19125-99-6). Likewise preferably, $R^{102}$ is linear or branched $C_1$-$C_{10}$-alkyl. The compounds of formula (X) can be synthesized in two steps. The first step may be the condensation of 4-chloro-1,8-naphthalic anhydride with amines in a solvent such as 1,4-dioxane or 2-methoxyethanol under reflux yielding the corresponding 4-chloro-1,8-naphthalimides. The second step involves the substitution of the chlorine atom with aliphatic primary or secondary amines.

Organic Fluorescent Colorant (B9)

7-(Diethylamino)-3-(5-methylbenzo[d]oxazol-2-yl)-2H-chromen-2-one is also known as Disperse Yellow (CAS Registry no. 34564-13-1).

Organic Fluorescent Colorant (B10)

Compounds of formulae (XIA) and (XIB) are known from U.S. Pat. No. 5,470,502. They are usually yellow fluorescent colorants. Preferred are compounds of formulae (XIA) and (XIB), wherein $R^{111}$ is linear $C_1$-$C_{10}$-alkyl or branched $C_3$-$C_{10}$-alkyl. Preferred examples are diisobutyl-3,9-perylenedicarboxylate, diisobutyl-3,10-perylenedicarboxylate and mixtures thereof. Especially preferred is a mixture of diisobutyl-3,9-perylenedicarboxylate and diisobutyl-3,10-perylenedicarboxylate.

Organic Fluorescent Colorant (B11)

Compounds of formulae (XIIA) and (XIIB) are known from U.S. Pat. No. 5,470,502. They are usually yellow fluorescent colorants. Preferred are compounds of formulae (XIIA) and (XIIB), wherein $R^{121}$ is linear $C_1$-$C_{10}$-alkyl or branched $C_3$-$C_{10}$-alkyl. Preferred examples are diisobutyl 4,10-dicyanoperylene-3,9-dicarboxylate and diisobutyl 4,9-dicyano-perylene-3,10-dicarboxylate and mixtures thereof.

Especially preferred is a mixture of diisobutyl 4,10-dicyanoperylene-3,9-dicarboxylate and diisobutyl 4,9-dicyanoperylene-3,10-dicarboxylate.

Organic Fluorescent Colorant (B12)

Naphthoylbenzimidazole compounds of formula (XIII) are known from EP 17151931.7. Compounds of formula (XIII) are usually yellow fluorescent compounds.

With regard to the use in color converters, compounds of formula (XIII) are preferred which correspond to a compound of formula (XIII-A)

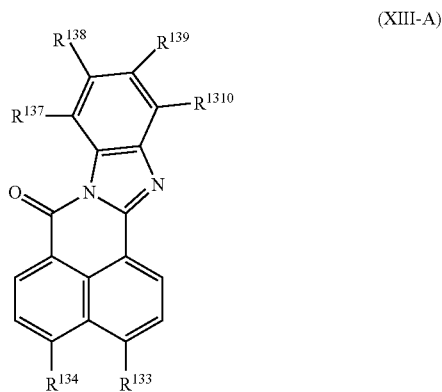

(XIII-A)

wherein
$R^{133}$ and $R^{134}$ are each independently hydrogen; phenyl; phenyl which carries 1 or 2 cyano groups; or phenyl which carries 1, 2 or 3 substituents selected from $C_1$-$C_{10}$-alkyl; and
$R^{137}$, $R^{138}$, $R^{139}$ and $R^{1310}$ are each independently hydrogen; phenyl; phenyl which carries 1 or 2 cyano groups; or phenyl which carries 1, 2 or 3 substituents selected from $C_1$-$C_{10}$-alkyl.

Among the compounds of formula (XIII-A), preference is given to compounds, in which $R^{138}$ and $R^{1310}$ have the same meaning. Likewise, preference is given to compounds, in which $R^{137}$ and $R^{139}$ have the same meaning and are in particular hydrogen. In particular, $R^{138}$ and $R^{1310}$ have the same meaning and $R^{137}$ and $R^{139}$ have the same meaning.

A particular preferred embodiment of the invention relates to compounds of formula (XIII-A), wherein
$R^{133}$ and $R^{134}$ are each independently selected from hydrogen; phenyl; phenyl which carries 1 or 2 cyano groups; and phenyl which carries 1, 2 or 3 $C_1$-$C_{10}$-alkyl substituents; in particular hydrogen, phenyl or phenyl which carries 1 cyano group;
$R^{137}$ is hydrogen;
$R^{138}$ is phenyl which carries 1 or 2 cyano groups; phenyl; or phenyl which carries 1, 2 or 3 substituents $C_1$-$C_{10}$-alkyl; in particular 4-cyanophenyl
$R^{139}$ is hydrogen; and
$R^{1310}$ is phenyl which carries 1 or 2 cyano groups; phenyl; or phenyl which carries 1, 2 or 3 substituents $C_1$-$C_{10}$-alkyl in particular 4-cyanophenyl.

A more particular preferred embodiment of the invention relates to compounds of formula (XIII-A), wherein
$R^{133}$ is phenyl; phenyl which carries 1 cyano group; or phenyl which carries 1 substituent selected from $C_1$-$C_{10}$-alkyl; in particular phenyl which carries 1 cyano group;
$R^{134}$ is hydrogen;
$R^{138}$ and $R^{1310}$ are each phenyl which carries 1 cyano group;
$R^{137}$ and $R^{139}$ are each hydrogen.

A further especially preferred embodiment of the invention relates to compounds of formula (XIII-A), wherein $R^{133}$ hydrogen;

$R^{134}$ is phenyl; phenyl which carries 1 cyano group; or phenyl which carries 1 substituent selected from $C_1$-$C_{10}$-alkyl; in particular phenyl which carries 1 cyano group;

$R^{138}$ and $R^{1310}$ are each phenyl which carries 1 cyano group;

$R^{137}$ and $R^{139}$ are each hydrogen.

Examples of preferred compounds of formula (XIII-A) are the compounds of formulae (XIII-A.1), (XIII-A.2) (XIII-A.3) and (XIII-A.4)

(XIII-A.1)

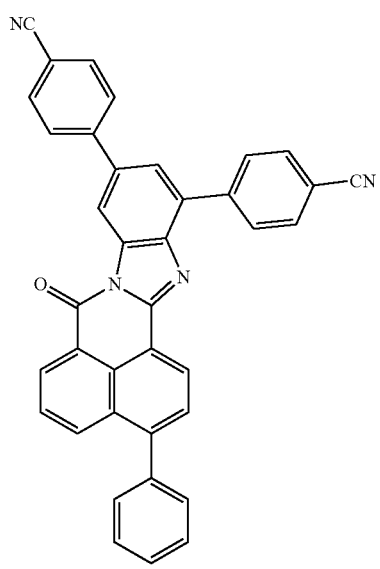

(XIII-A.2)

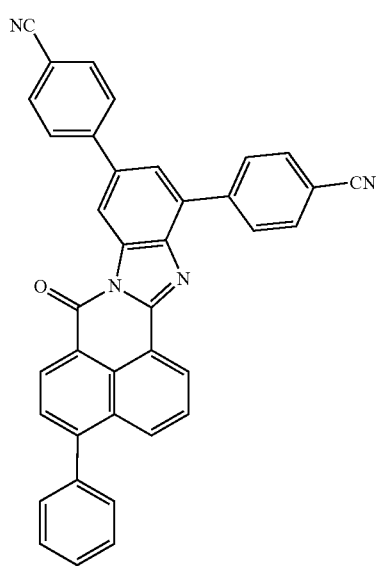

(XIII-A.3)

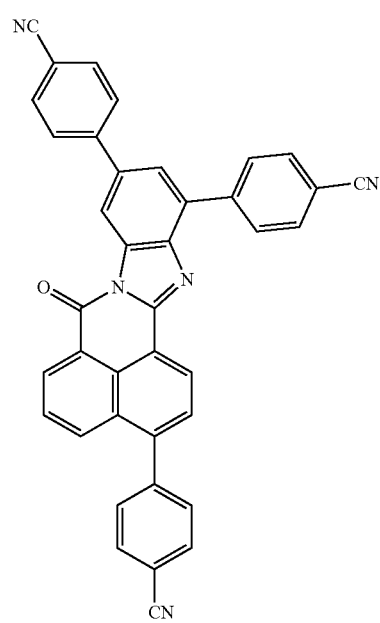

(XIII-A.4)

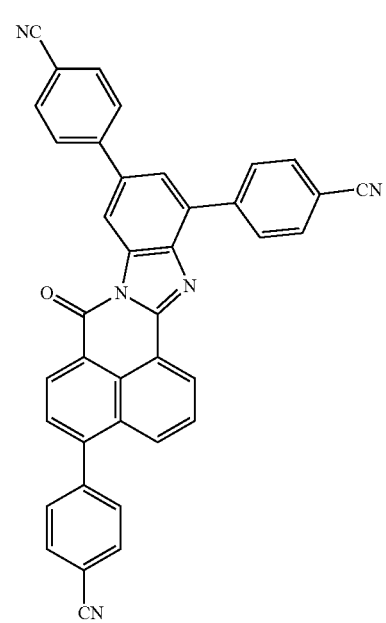

Compounds of formula (XIII) and mixtures thereof can be prepared in analogy to standard methods, for example as described in WO 2012/168395, especially on pages 64-81 or WO 2015/019270, on pages 21-30.

Organic Fluorescent Colorant (B13)

Compounds of formula (XIV) are subject matter of WO 2017/121833. Compounds of formula (XIV) are usually orange or red fluorescent colorants. Preference is given to compounds of formula (XIV), where $R^{141}$ and $R^{142}$ are, independently of each other, selected from phenyl which is unsubstituted or substituted by 1, 2 or 3 $C_1$-$C_6$-alkyl; and $R^{143}$, $R^{144}$, $R^{145}$, $R^{146}$, $R^{147}$, $R^{148}$, $R^{149}$, $R^{1410}$, $R^{1411}$, $R^{1412}$, $R^{1413}$, $R^{1414}$, $R^{1415}$, $R^{1416}$, $R^{1417}$ and $R^{1418}$ are each hydrogen. A preferred colorant of the formula (XIV) is the compound

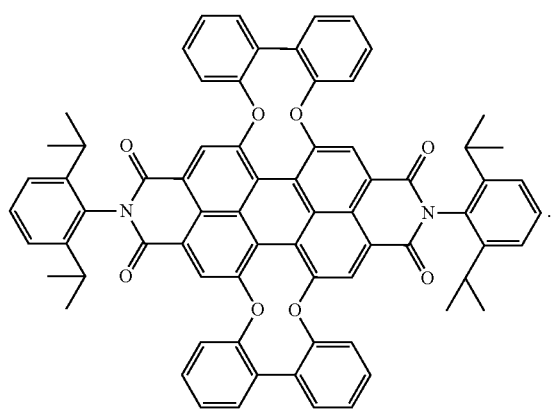 [SMILES: CC(C)c1cccc(C(C)C)c1N1C(=O)c2cc3c4c5c(cc6c7c(cc8c(c9c(cc(c2c49)C1=O)Oc1ccccc1-c1ccccc1O8)c75)C(=O)N(c1c(C(C)C)cccc1C(C)C)C6=O)Oc1ccccc1-c1ccccc1O3]

Organic Fluorescent Colorant (B14)

Suitable examples of compounds of formula (XV) are for example the perylene derivatives specified in WO 2007/006717, especially at page 1, line 5 to page 22, line 6; in U.S. Pat. No. 4,845,223, especially col. 2, line 54 to col. 6, line 54; in WO 2014/122549, especially at page 3, line 20 to page 9, line 11; in EP 3072887; and in EP 16192617.5, especially at page 35, line 34 to page 37, line 29. The compounds of formula (XV) are usually orange or red fluorescent colorants. Preferred are compounds of formula (XV), wherein $R^{151}$ and $R^{152}$ are each independently selected from $C_1$-$C_{10}$-alkyl, 2,6-di($C_1$-$C_{10}$-alkyl)aryl and 2,4-di($C_1$-$C_{10}$-alkyl)aryl. More preferably, $R^{151}$ and $R^{152}$ are identical. Very particularly, $R^{151}$ and $R^{152}$ are each 2,6-diisopropylphenyl or 2,4-di-tert-butylphenyl. $R^{153}$ is preferably phenoxy, which is unsubstituted or substituted by 1 or 2 identical or different substituents selected from fluorine, chlorine, $C_1$-$C_{10}$-alkyl and phenyl. Preferably, $p_{15}$ is 2, 3 or 4, in particular 2 or 4.

The compounds of formula (XV) can be prepared in analogy to the methods described for example in WO 2007/006717, U.S. Pat. No. 4,845,223, EP 3072887 and WO 2014/122549. Suitable organic fluorescent colorants B14 are, for example, N,N'-bis(2,6-diisopropylphenyl)-1,6,7,12-tetraphenoxyperylene-3,4:9,10-tetracarboximide, N,N'-bis(2,6-diisopropylphenyl)-1,7-di(2,6-diisopropylphenoxy)perylene-3,4:9,10-tetracarboximide, N,N'-bis(2,6-diisopropylphenyl)-1,6-di(2,6-diisopropylphenoxy)perylene-3,4:9,10-tetracarboximide, N,N'-bis(2,6-diisopropylphenyl)-1,7-di(p-tert-octylphenoxy)perylene-3,4:9,10-tetracarboximide, N,N'-bis(2,6-diisopropylphenyl)-1,7-diphenoxyperylene-3,4:9,10-tetracarboximide, N,N'-bis(2,6-diisopropylphenyl)-1,7-di(2,6-diphenylphenoxy)perylene-3,4:9,10-tetracarboximide, N,N'-bis(2,6-diisopropylphenyl)-1,6-di(2,6-diphenylphenoxy)perylene-3,4:9,10-tetracarboximide, N,N'-bis(2,6-diisopropylphenyl)-1,6,7,12-tetra(2-phenylphenoxy)perylene-3,4:9,10-tetracarboximide, N,N'-bis(2,6-diisopropylphenyl)-1,6,7,12-tetra(p-tert-octylphenoxy)perylene-3,4:9,10-tetracarboximide, N,N'-bis(2,6-diisopropylphenyl)-1,7-di(2,3-difluorophenoxy)perylene-3,4:9,10-tetracarboximide, N,N'-bis(2,6-diisopropylphenyl)-1,6,7,12-tetra(2,3-difluorophenoxy)perylene-3,4:9,10-tetracarboximide, N,N'-bis(2,6-diisopropylphenyl)-1,6,7,12-tetra(3-fluorophenoxy)perylene-3,4:9,10-tetracarboximide, N,N'-bis(2,6-diisopropylphenyl)-1,6,7,12-tetra(2,6-difluorophenoxy)perylene-3,4:9,10-tetracarboximide, N,N'-bis(2,6-diisopropylphenyl)-1,6,7,12-tetra(2,5-difluorophenoxy)perylene-3,4:9,10-tetracarboximide, N,N'-bis(2,6-diisopropylphenyl)-1,6,7,12-tetra(2,3-dichlorophenoxy)perylene-3,4:9,10-tetracarboximide, N,N'-bis(2,6-diisopropylphenyl)-1,6,7,12-tetra(3-chlorophenoxy)perylene-3,4:9,10-tetracarboximide, N,N'-bis(2,6-diisopropylphenyl)-1,6,7,12-tetra(2,6-dichlorophenoxy)perylene-3,4:9,10-tetracarboximide, N,N'-bis(2,6-diisopropylphenyl)-1,6,7,12-tetra(2,5-dichlorophenoxy)perylene-3,4:9,10-tetracarboximide.

The color converter may comprise, as well as the at least one organic fluorescent colorant present in accordance with the invention 1, 2, 3, 4, 5, 6, 7 or more than 7 organic fluorescent colorants (B) as defined above, each colorant generating a different color such that the mixed light, for example, generates white light having specific color temperature and/or color rendering index. Preferably, the color converter additionally comprises 1 or 2 organic fluorescent colorants B. In a specific embodiment, the color converter comprises a compound of formula (I) and a yellow emitting colorant. It may also be beneficial to use two different colorants (B), such as a combination of a yellow emitting colorant (B) and a red emitting colorant (B).

In a specific embodiment, the color converter may especially comprise at least one compound comprising at least one structural unit of formula (VII) as defined above, especially one mentioned as being preferred.

In a further specific embodiment, the color converter may especially comprise at least one compound of formula (VIII). In a further specific embodiment, the color converter may especially comprise at least one compound of formula (IX). In a further specific embodiment, the color converter may especially comprise at least one compound of formula (XIA), especially one mentioned as being preferred. In a further specific embodiment, the color converter may especially comprise at least one compound of formula (XIB), especially one mentioned as being preferred. In a further specific embodiment, the color converter may especially comprise at least one compound of formula (XIIA), especially one mentioned as being preferred. In a further specific embodiment, the color converter may especially comprise at least one compound of formulae (XIIB), especially one mentioned as being preferred. In a further specific embodiment, the color converter may especially comprise at least one compound of formula (XIII).

The concentration of the compound of formula (I) and the organic fluorescent colorant(s) (B) as defined above in the polymer matrix is set as a function of the thickness of the color converter and the type of polymer. If a thin polymer layer is used, the concentration of these organic fluorescent colorants is generally higher than in the case of a thick polymer layer. Typically, the total amount of organic fluorescent colorants in the polymer also depends on the correlated color temperature CCT to be achieved. A skilled person will appreciate that by increasing the concentration of yellow fluorescent colorant(s) and red fluorescent colorant(s), the light emitted from the LED is tuned to longer wavelength to obtain white light with a required CCT.

Typically, the total concentration of red organic fluorescent colorant(s) (i.e. the compound of formula (I) and optionally further red organic fluorescent colorant(s) B)) used in the color converter is in the range from 0.0001 to 0.5% by weight, preferably 0.001 to 0.1% by weight, based on the amount of polymer used. The total concentration of yellow or yellow-green organic fluorescent colorant(s) B typically is 0.002 to 0.5% by weight, preferably 0.003 to 0.4% by weight, based on the amount of the polymer used.

It may be advantageous, for example in view of CCT and/or color rendering index (CRI), to use a mixture of inventive fluorescent colorant of formula (I), yellow fluorescent colorant(s) and further red fluorescent colorant(s). The ratio of yellow or yellow-green emitting organic fluorescent colorant(s) to red organic fluorescent colorant(s) present in the color converter is typically in the range from 1:1 to 25:1, preferably 2:1 to 20:1, more preferably 2:1 to 15:1, such as 10:1 or 3:1 or 4:1. A skilled person will readily appreciate that the ratio of the colorants depends on the chosen light source. For a desired CCT, the ratio of yellow colorant/red colorant is much greater, if the light is generated by a blue LED with a center wavelength of emission between 420 nm and 480 nm in comparison to the ratio of yellow colorant/red colorant if the light is generated by a white LED having a CCT between 6 000 to 20 000 K.

According to any of the above embodiments, the color converter according to the present invention may optionally or alternatively comprise as further fluorescent material at least one inorganic fluorescent material. The at least one inorganic fluorescent material is preferably selected from garnets, silicates, sulfides, nitrides and oxynitrides.

Suitable examples of garnets, silicates, sulfides, nitrides and oxynitrides are compiled in table I below:

The group Ill-V compound semiconductor nanocrystal may include one selected from a group consisting of GaN, GaP, GaAs, AlN, AlP, AlAs, InN, InP, InAs, GaNP, GaNAs, GaPAs, AlNP, AlNAs, AlPAs, InNP, InNAs, InPAs, GaAINP, GaAINAs, GaAIPAs, GaInNP, GaInNAs, GaInPAs, InAINP, InAINAs, and InAIPAs. The IV-VI compound semiconductor nano crystal may be SnTe.

To synthesize a nanocrystal in form of a quantum dot, quantum dots may be prepared by vapor deposition such as metal organic chemical vapor deposition or molecular beam epitaxy, or by a wet chemical process in which a crystal is grown by adding one or more precursors into an organic solvent.

In a more preferred embodiment of the invention, the inventive color converter does not comprise quantum dots. Likewise, in a more preferred embodiment of the invention, the inventive color converter does not comprise inorganic fluorescent materials.

In one embodiment of the invention, inventive color converters have a laminate structure. They may either have a monolayer structure or a multilayer structure, generally composed of a plurality of polymer layers comprising one or

TABLE I

| Class | Compounds | Excitation Peak [nm] | Emission Peak [nm] | Reference |
|---|---|---|---|---|
| Garnets | YAG:Ce<br>($Y_3Al_5O_{12}$:Ce)<br>(Y,Gd,Tb,Lu)$_3Al_5O_{12}$:Ce | 460-470 | 550 | U.S. Pat. No. 5,998,925 |
|  | TAG:Ce<br>($Tb_3Al_5O_{12}$:Ce) | 460-470 | 575 | U.S. Pat. No. 6,669,866,<br>U.S. Pat. No. 6,812,500,<br>U.S. Pat. No. 6,576,930,<br>U.S. Pat. No. 6,0060,861,<br>U.S. Pat. No. 6,245,259,<br>U.S. Pat. No. 6,765,237 |
| Silicates | Eu-doped Silicates<br>$A_2Si(OD)_4$:Eu with A = Sr,<br>Ba, Ca, Mg, Zn and D = F,<br>Cl, S, N, Br | <460 | 510 to 610 | U.S. Pat. No. 7,311,858,<br>U.S. Pat. No. 7,267,787 |
|  | $(SrBaCa)_2SiO_4$:Eu |  |  | U.S. Pat. No. 6,809,347,<br>U.S. Pat. No. 6,943,380 |
|  | $Sr_3SiO_5$<br>$Ba_2MgSi_2O_7$:$Eu^{2+}$;<br>$Ba_2SiO_4$:$Eu^{2+}$<br>$(Ca, Ce)_3(Sc, Mg)_2Si_3O_{12}$ |  |  | U.S. Pat. No. 6,429,583<br>WO 02/11214 |
| Sulfides | (Ca, Sr)S:Eu | <460 | 615-660 |  |
| Nitrides | ($CaAlSiN_3$:$Eu^2$)<br>(Sr, Ca)$AlSiN_3$:$Eu^{2+}$ | 455 | red<br>orange | WO2005052087 |
| Oxy-nitrides | SiAlON:Ce<br>ß-SiAlON:Eu<br>Ca-alpha-SiAlON:Eu<br>($Ba_3Si_6O_{12}N_2$:Eu)<br>General formula<br>$Ca_xEu_y(Si,Al)_{12}(O,N)_{16}$ | 300-580 | 490<br>540<br>585-595 |  |

According to a further preferred embodiment, the inventive color converter comprises at least one quantum dot. Quantum dots are nanocrystals of a semiconductor material having a diameter of about 20 nm or less. The quantum dot may include one of a Si-based nanocrystal, a group II-VI compound semiconductor nanocrystal, a group Ill-V compound semiconductor nanocrystal, a group IV-VI compound nanocrystal and a mixture thereof. The group II-VI compound semiconductor nanocrystal may include one selected from a group consisting of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HggZnTe, CdZnSeS, CdZnSeTe, CdZnSTe, CdHgSeS, CdHgSeTe, CdHgSTe, HgZnSeS, HgZnSeTe and HgZnSTe.

more fluorescent colorants and/or scattering bodies. If the color converter has a multilayer structure, one layer comprises the fluorescent colorant according to the invention and another layer comprises at least one fluorescent colorant encompassed by the present invention.

In one embodiment, the at least one compound of formula (I) is present in the layer of the color converter facing the LED. In another embodiment, the at least one further fluorescent colorant is present in the layer of the color converter facing the LED.

If the inventive color converters comprise at least one further organic fluorescent colorant, it is possible in one embodiment of the invention for a plurality of fluorescent colorants to be present alongside one another in one layer. In another embodiment, the various fluorescent colorants are present in various layers.

In a specific embodiment, at least one of the layers or matrices comprising organic fluorescent colorants comprises scattering bodies for light.

In a special embodiment, the color converter has a multilayer structure, preferably a two-layer structure, wherein each layer comprises at least one organic fluorescent colorant. In this embodiment, one of the layers or more than one but not all of the layers or all of the layers comprise a scattering body, preferably $TiO_2$.

In one embodiment, the color converters consist of a plurality of polymer layers which have been laminated together to form a composite and wherein the various fluorescent colorants and/or scattering bodies may be present in different polymer layers.

In a further embodiment, at least one polymer layer of the color converter has been mechanically reinforced with glass fibers.

Suitable color converters may be in any desired geometric arrangement. The color converters may, for example, be in the form of films, sheets or plaques. Equally, the matrix containing organic fluorescent colorants may be in droplet form or hemispherical form or in the form of lenses with convex and/or concave, flat or spherical surfaces. "Casting" refers to the embodiment where LEDs or components comprising LEDs are fully cast or enveloped with a polymer comprising organic fluorescent colorant. In one embodiment of the invention, the polymer layers (matrices) comprising at least one organic fluorescent colorant are 25 to 1000 micrometers (μm) thick, preferably 35 to 400 μm and particularly 50 to 300 μm.

In another embodiment, the polymer layers comprising organic fluorescent colorants are 0.2 to 5 millimeters thick, preferably 0.3 to 3 mm and more preferably 0.4 to 1 mm.

If the color converters consist of one layer or they have a laminate structure, the individual layers, in a preferred embodiment, are continuous and do not have any holes or interruptions.

Inventive color converters may optionally comprise further constituents, such as a backing layer.

Backing layers serve to impart mechanical stability to the color converter. The type of material for the backing layers is not crucial, provided that it is transparent and has the desired mechanical strength. Suitable materials for backing layers are, for example, glass or transparent rigid organic polymers, such as polycarbonate, polystyrene or polymethacrylates or polymethyl methacrylates.

Backing layers generally have a thickness of 0.1 mm to 10 mm, preferably 0.2 mm to 5 mm, more preferably 0.3 mm to 2 mm.

In one embodiment of the invention, inventive color converters have at least one barrier layer against oxygen and/or water, as disclosed in WO 2012/152812. Examples of suitable barrier materials for barrier layers are, for example, glass, quartz, metal oxides, $SiO_2$, a multilayer system composed of alternating layers of $Al_2O_3$ and $SiO_2$ layers, titanium nitride, $SiO_2$/metal oxide multilayer materials, polyvinyl alcohol, polyacrylonitrile, polyvinylidene chloride (PVDC), liquid crystal polymers (LCP), polystyrene-acrylonitrile (SAN), polybutylene terephthalate (PBT), polybutylene naphthalate (PBN), polyethylene terephthalate (PET), polyethylene naphthalate (PEN), polyvinyl butyrate (PBT), polyvinyl chloride (PVC), polyamides, polyoxymethylenes, polyimides, polyetherimides, epoxy resins, polymers which derive from ethylene-vinyl acetate (EVA) and polymers which derive from ethylene-vinyl alcohol (EVOH). A preferred material for barrier layers is glass or a multilayer system composed of alternating layers of $Al_2O_3$ and $SiO_2$ layers. Preferably, suitable barrier layers have low permeability for oxygen. More preferably, suitable barrier layers have low permeability for oxygen and water.

Inventive color converters can be produced by different processes. In one embodiment, the process for producing inventive color converters comprises the dissolution of the at least one polymer and of the at least one organic fluorescent colorant in a solvent and subsequent removal of the solvent. In another embodiment, the process for production of inventive color converters comprises the extrusion of the at least one organic fluorescent colorant with the at least one polymer.

Inventive color converters are especially suitable for use in displays.

Inventive color converters are especially suitable for the conversion of blue light to white light. More particularly, they are suitable for conversion of light generated by a blue LED with a center wavelength of emission between 400 nm and 480 nm to provide white light. Suitable blue LEDs are, for example, those based on gallium nitride (GaN) or indium gallium nitride (InGaN). They are commercially available Inventive color converters are also especially suitable for conversion of light generated by a cool white LED having a correlated color temperature between 3 000 K and 20 000 K to provide white light having a lower correlated color temperature. With regard to suitable white LEDs, reference is made to what is said herein above. Cool white LEDs with a CCT between 3 000 to 20 000K, especially 4 000 K to 20 000 K are also commercially available.

Likewise possible is their use for conversion of light produced by mercury lamps or by organic light-emitting diodes (OLEDs).

Inventive color converters for use in lighting devices are used in a remote phosphor setup. In this case, the color converter is spatially separated from the LED. In general, the distance between LED and color converter is larger than 0.1 mm, such as 0.2 mm or more, and in some embodiments equal to or larger than 0.1 to 10 cm such as 0.3 to 5 cm or 0.5 to 3 cm. Between color converter and LED may be different media such as air, noble gases, nitrogen or other gases or mixtures thereof.

The inventive color converters are additionally suitable for applications as a light-collecting system (fluorescence collector) in photovoltaics and in fluorescence conversion solar cells.

A further aspect of the present invention relates to a lighting device (illumination device) comprising
(i) at least one LED selected from a blue LED with a center wavelength of emission from 400 nm to 480 nm and a cool white LED having a correlated color temperature between 3 000 K and 20 000 K, especially 4 000 to 20 000 K; and
(ii) at least one color converter as defined herein above, wherein the at least one color converter is in a remote arrangement from the at least one LED, i.e. the color converter is spatially separated from the LED.

In one embodiment, inventive lighting devices comprise exactly one LED. In another embodiment, inventive lighting devices comprise several LEDs. In one embodiment, inventive lighting devices comprise several LEDs, all of which are blue. In another embodiment, inventive lighting devices comprise several LEDs, at least one LED being blue and at least one LED not being blue, but rather emitting light in another color.

In general, the type of LED used is not crucial for the inventive lighting devices. In a preferred embodiment, the power density of the blue LED light impinging the surface of the converter plate is usually less than 200 mW/cm², preferably less than 120 mW/cm², more preferably less than 80 mW/cm². The use of LEDs of higher power densities, such as 150 or 200 mW/cm², is likewise possible.

The color converter may, for example, be arranged concentrically around the LED or have a planar geometry. It may take the form, for example, of a plaque, sheet or film, be in droplet form or take the form of a casting.

Inventive lighting devices are suitable for lighting in interiors, outdoors, of offices, of vehicles, in torches, games consoles, streetlights, traffic signs. Inventive lighting devices exhibit warm-tone white light with a high average color rendering index. In addition, they have a long lifetime, especially a high photostability on illumination with blue light. Inventive lighting devices exhibit a high quantum yield. In addition, they have a long lifetime, especially a high photostability on illumination with blue light. They emit pleasant light with good color reproduction.

The present invention further provides a device producing electric power upon illumination comprising a photovoltaic cell (solar cell) and the color converter as defined herein above, where at least a part of the light not absorbed by the photovoltaic cell (solar cell) is absorbed by the color converter. The color converter is usually on top of the photovoltaic cell. The color converter is used to modify the spectrum such that UV and visible light are converted to a more bathochromic spectrum that is converted at higher efficiency by the solar cell.

Inventive compounds of formula (I) and mixtures thereof are notable for use in color converters for converting light emitted from a blue LED with a center wavelength of emission between 400 nm and 480 nm into light of a second, longer wavelength or for converting light emitted from a cool-white LED having a correlated color temperature between 3 000 K and 20 000 K to provide white light having a lower correlated color temperature, for coloring coatings, printing inks and plastics, producing aqueous polymer dispersions which absorb and/or emit electromagnetic radiation, for data storage, for data transmission, for optical labels, for security labels in documents and for brand protection or as a fluorescent label for biomolecules.

Owing to their short fluorescence decay time, usually in the range from 0.1 to 9 ns, perylene bisimide compounds of formula (I) are also of particular interest for use in color converters for data transmission in light fidelity applications comprising a transmitter for transmitting data and for emitting electromagnetic radiation in the visible range.

Accordingly, the present invention also relates to a transmitter for transmitting data and for emitting electromagnetic radiation in the visible spectral range, said transmitter comprising:
 a radiation source for generating and emitting first electromagnetic radiation and
 a modulator being adapted to modulate the first electromagnetic radiation depending on the data to be transmitted generating modulated first electromagnetic radiation,
characterized in that the transmitter further comprises
 a color converter for converting at least a part of the modulated first electromagnetic radiation into modulated second electromagnetic radiation, said modulated second electromagnetic radiation being different from the modulated first electromagnetic radiation,
wherein the color converter comprises the compound of formula (I) as defined in above and a polymer matrix.

Many different radiation sources may be used by the transmitter of the present invention. However, according to an embodiment of the present invention, the radiation source is a light emitting diode (LED). Furthermore, a laser diode may be used as radiation source. Preferably, the radiation source of the transmitter of the present invention is selected from the group consisting of an UV-LED, a blue LED, a RGB LED system, an organic LED and a cool white LED.

As regards the color converter used in the transmitter, reference is made to what is said herein above. In particular, the distance between the radiation source and the color converter in the range from 0.01 to 10 cm.

A special field of application for fluorescent materials regards inks for printing processes, which are used for security printing.

Accordingly, the present invention also relates to a printing ink formulation for security printing, comprising at least one compound of the formula (I) or a mixture thereof as defined above. The compounds of formula (I) exhibit strong fluorescence at 580-650 nm under excitation at 450 nm.

Security printing is the field that deals with the printing of items such as currency, passports, tamper-evident labels, stock certificates, tax stamps, postage stamps, identity cards, etc. The main goal of security printing is to prevent forgery, tampering or counterfeiting. All security documents are required to have good stability and durability. In the case of bank notes, these requirements are extreme, as bank notes are subjected to toughest use conditions by the public—they are subjected to material stress by folding, crumpling etc., subjected to abrasion, exposed to weather, exposed to bodily fluids such as perspiration, laundered, dry-cleaned, ironed etc.—and, after having been subjected to this, are expected to be as legible as when they started. Furthermore, it is essential that the documents nevertheless should have a reasonable life time, ideally of some years, despite suffering the afore-mentioned conditions. During this time, the documents, and thus the inks on them (including invisible security markings), should be resistant to fading or colour change. Hence, any ink used in a security printing process should, when cured, be robust, water-resistant, resistant to various chemicals and flexible. Moreover, as certain states are moving away from the use of paper as the substrate for bank notes, the employed printing ink formulations should be useable on plastics as well as paper. It has now been found that the compounds of the general formula (I) because of their unique application properties are especially suitable for printing ink formulations that are employed for security printing and in particular for bank notes.

In security printing, the fluorescent colorant of formula (I) is added to a printing ink formulation. Suitable printing inks are water-based, oil-based, or solvent-based printing inks, based on pigment or dye, for inkjet printing, flexographic printing, gravure printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing, letterpress printing and intaglio printing are usually formulated as high-viscosity paste printing inks, whereas printing inks for flexographic printing and inkjet printing are usually formulated as liquid printing inks with comparatively low viscosity.

In the context of the present invention, the expression "printing ink" also encompasses formulations that in addition to at least one fluorescent colorant of the general formula (I) comprise a colorant. The expression "printing ink" also encompasses printing lacquers that comprise no colorant.

The printing ink formulation for security printing according to the invention preferably comprises a) at least one compound of the formula (I) or a mixture thereof as defined herein above;
b) a polymeric binder;
c) optionally an organic solvent;
d) optionally at least one colorant; and
e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"-Ullmann's Encyclopedia of Industrial Chemistry, Sixth Edition, 1999 Electronic Release.

The printing ink formulation according to the invention contains in general from 0.0001 to 25% by weight, preferably from 0.001 to 15% by weight, in particular from 0.01 to 5% by weight, based on the total weight of the printing ink formulation, of component a).

The compounds of the general formula (I) are present in the printing ink formulation in dissolved form or in solid form (in a finely divided state).

The printing ink formulation according to the invention contains in general from 5 to 75% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 0 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvents are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains from 0 to 25% by weight, more preferably from 0.1 to 20% by weight, in particular from 1 to 15% by weight, based on the total weight of the printing ink formulation, of a colorant d).

Suitable colorants d) are selected from conventional dyes and in particular conventional pigments. The term "pigment" is used in the context of this invention comprehensively to identify all pigments and fillers, examples being colour pigments, white pigments, and inorganic fillers. These include inorganic white pigments, such as titanium dioxide, preferably in the rutile form, barium sulfate, zinc oxide, zinc sulfide, basic lead carbonate, antimony trioxide, lithopones (zinc sulfide+barium sulfate), or coloured pigments, examples being iron oxides, carbon black, graphite, zinc yellow, zinc green, ultramarine, manganese black, antimony black, manganese violet, Paris blue or Schweinfurt green. Besides the inorganic pigments the printing ink formulation of the invention may also comprise organic colour pigments, examples being sepia, gamboge, Cassel brown, toluidine red, para red, Hansa yellow, indigo, azo dyes, anthraquinonoid and indigoid dyes, and also dioxazine, quinacridone, phthalocyanine, isoindolinone, isoindoline, perylene and metal complex pigments. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains from 0 to 25% by weight, more preferably from 0.1 to 20% by weight, in particular from 1 to 15% by weight, based on the total weight of the printing ink formulation, of at least one component e).

Suitable additives (component e)) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains
a) 0.0001 to 25% by weight of at least one compound of the formula (I) or a mixture thereof as defined above;
b) 5 to 75% by weight of at least one polymeric binder,
c) 0 to 94.9999% by weight of at least one solvent,
d) 0 to 25% by weight of at least one colorant, and
e) 0 to 25% by weight of at least one further additive,
wherein the sum of components a) to e) adds up to 100%.

The printing ink formulations according to the invention are advantageously prepared in a conventional manner, for example by mixing the individual components. As mentioned earlier, the fluorescent colorant of formula (I) is present in the printing ink formulations in a dissolved or finely divided solid form. Additional colorants may be employed in the printing ink formulation of the invention or in a separate ink formulation. When additional colorants are to be employed in a separate formulation, the time of application of the printing ink formulation according to the invention is usually immaterial. The printing ink formulation according to the invention can for example be applied first and then be overprinted with conventional printing inks. But it is also possible to reverse this sequence or, alternatively, to apply the printing ink formulation according to the invention in a mixture with conventional printing inks. In every case the prints are readable with suitable light sources.

Primers can be applied prior to the printing ink formulation according to the invention. By way of example, the primers are applied in order to improve adhesion to the substrate. It is also possible to apply additional printing lacquers, e.g. in the form of a covering to protect the printed image. Additional printing lacquers may also be applied to serve aesthetic purposes, or serve to control application-related properties. By way of example, suitably formulated additional printing lacquers can be used to influence the roughness of the surface of the substrate, the electrical properties, or the water-vapour-condensation properties. Printing lacquers are usually applied in-line by means of a lacquering system on the printing machine employed for printing the printing ink formulation according to the invention.

The printing ink formulations according to the invention are also suitable for use in multilayer materials. Multilayer materials are e.g. composed of two or more plastics foils, such as polyolefin foils, metal foils, or metallised plastics foils, which are bonded to one another, by way of example, via lamination or with the aid of suitable laminating adhesives. These composites may also comprise other functional layers, such as optically variable layers, odour-barrier layers or water-vapour barriers.

The printing ink formulations according to the present invention are especially suitable for offset, letterpress, gravure and intaglio printing.

When a transparent substrate is used, the type of lamp for exciting the fluorescent colorant of formula (I) is generally not critical, i.e. all light sources emitting light at wavelength within the absorption profile of the fluorescent colorant of formula (I).

A further object of the present invention is a process for the manufacture of a security document comprising the steps printing on a substrate a printing ink formulation as defined above.

A further object is a security document, comprising a substrate, a cured ink which ink comprises at least one compound of the formula (I) or a mixture thereof as defined above.

A further object is a security document as defined above obtainable by a printing process wherein a printing ink formulation as defined above is employed. The security document is preferably selected from a bank note, a passport, a check, a voucher, an ID- or transaction card, a stamp and a tax label. The security document can also be part of a rigid or flexible packaging, of a carton board or of a brand or product label.

EXAMPLES

The following examples serve to illustrate the invention and should not be interpreted as limiting.

Example 1

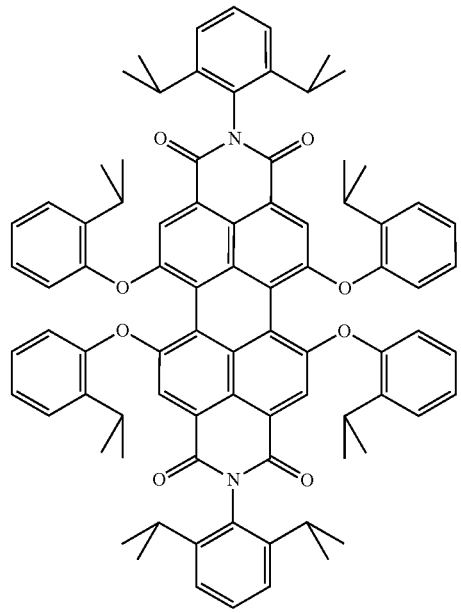 [SMILES: CC(C)c1ccccc1Oc1cc2c3c(cc(Oc4ccccc4C(C)C)c4c5c(Oc6ccccc6C(C)C)cc6c7c(cc(Oc8ccccc8C(C)C)c(c1c34)c75)C(=O)N(c1c(C(C)C)cccc1C(C)C)C6=O)C(=O)N(c1c(C(C)C)cccc1C(C)C)C2=O]

A mixture of 2.2 g (2.6 mmol) of 1,6,7,12-tetrachloro-N,N'-2,6-diisopropylphenyl-perylene-3,4,9,10-tetracarboxylic acid diimide, 4.25 g (31.2 mmol) of 2-isopropylphenol, 2.52 g (18.2 mmol) of $K_2CO_3$ and 170 mL of N-methylpyrrolidone were heated to 90° C. for 17 hours. Afterwards the mixture was heated to 110° C. for 10 hours. Further 2.12 g (15.6 mmol) of 2-isopropylphenol and 1.26 g of $K_2CO_3$ were added and heating continued for 23 hours. Further 2.12 g (15.6 mmol) of 2-isopropylphenol and 1.26 g of $K_2CO_3$ were added and heating continued for 6 hours. The product was precipitated with 1 L of diluted HCl. After extraction with dichloromethane 7.5 g of a liquid crude material was obtained which was further purified by column chromatography using toluene dicholoromethane. 1.66 g (51.4%) of pure title compound were isolated.

Rf (petroleum ether/ethylacetate 8:1)=0.3.
Lambda max emission: 616 nm (in polycarbonate).
Lambda max emission: 620 nm (in polystyrene).

Photostability Test:

The photostability of the compound of example 1 and of a comparative compound C-1, namely N,N'-bis(2,6-diisopropylphenyl)-1,6,7,12-tetraphenoxyperylene-3,4:9,10-tetracarboximide,

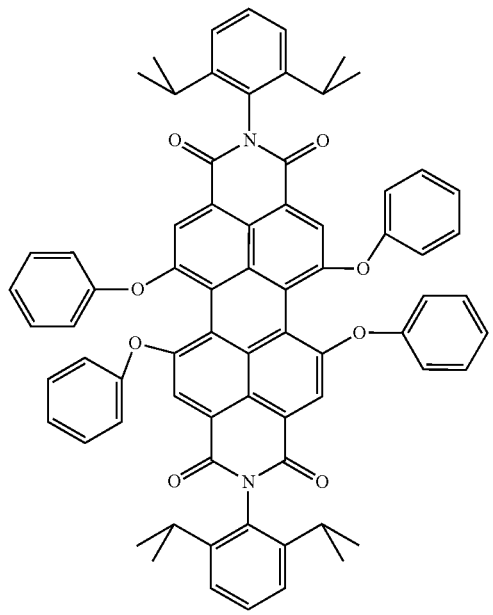

(C-1)

were tested. The compound of example 1 differs from the comparative compound C-1 in the substituents attached at 1-, 6-, 7- and 12-positions. The compound of inventive example 1 carries a 2-isopropylphenoxy substituent at that positions, whereas compound C-1 carries a phenoxy substituent.

To this end, polycarbonate films (Macrolon® 2808 from Bayer) with fluorescent colorants according to table II hereinbelow were prepared. The films were illuminated with blue light of 450 nm at a light flux intensity of 100 mW/cm² using a Fortimo LED DLM 2000 21W/830 Gen5 from Philips. The fluorescence intensity was measured as a function of irradiation time. Illumination was stopped when the fluorescence intensity reached 80% (T80) of its initial value. The results are summarized in table II.

TABLE II

| Lifetime (days) upon irradiation (T80) | | | |
|---|---|---|---|
| | Concentration [% by weight] | Absorption | T80 [days] |
| compound of example 1 | 0.03 | 41% | 255 |
| compound C-1 | 0.03 | 50% | 150 |

As can be seen from table II, the compound according to the present invention has a substantial longer lifetime under the irradiation conditions than structurally similar compound C-1 known from prior art.

The invention claimed is:

1. A perylene bisimide compound of formula (I)

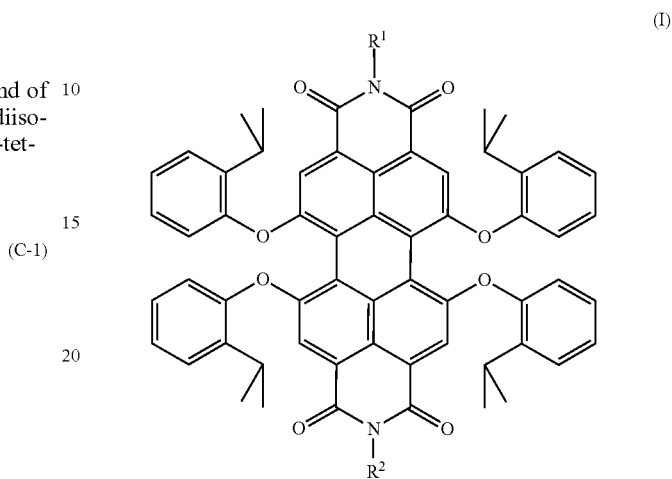

(I)

wherein $R^1$ and $R^2$ independently of each other are $C_6$-$C_{24}$-aryl which is substituted with 1, 2, 3, 4 or 5 identical or different radicals $R^a$;
where $R^a$ is $C_1$-$C_{24}$-alkyl, $C_1$-$C_{24}$-fluoroalkyl, $C_1$-$C_{24}$-alkoxy, fluorine, chlorine or bromine.

2. The perylene bisimide compound of formula (I) according to claim 1, wherein $R^1$ and $R^2$ are 2,6-diisopropylphenyl.

3. The perylene bisimide compound of formula (I) according to claim 1, wherein $R^a$ is $C_1$-$C_{24}$-alkyl.

4. The perylene bisimide compound of formula (I) according to claim 1, wherein $R^1$ and $R^2$, independently of each other, are a radical of the formula (B.2)

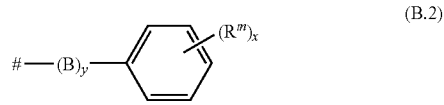

(B.2)

in which # represents the bonding site to the nitrogen atom;
y is 0;
$R^m$ is, independently of one another, selected from $C_1$-$C_{24}$-alkyl;
x, in formulae (B.2) is 2.

5. A color converter, comprising at least one polymer as a matrix and at least one perylene bisimide compound of formula (I) according to claim 1 as a fluorescent colorant, wherein the at least one polymer consists essentially of polystyrene, polycarbonate, polyacrylate, polymethylmethacrylate, polymethacrylate, polyvinylpyrrolidone, polyvinyl acetate, polyvinyl chloride, polybutene, silicone, epoxy resin, polyvinyl alcohol, poly(ethylene vinylalcohol)-copolymer, polyacrylonitrile, polyvinylidene chloride, polystyrene acrylonitrile, polybutylene terephthalate, polyethylene terephthalate, a 2,5-furandicarboxylate polyester, polyvinyl butyrate, polyvinyl chloride, polyamides, polyoxymethylenes, polyimides, polyetherimides or mixtures thereof.

6. The color converter according to claim 5, wherein the color converter additionally comprises at least one inorganic white pigment as a scattering body.

7. The color converter according to claim 5 or 6, comprising at least one further organic fluorescent colorant (B) selected from:
(B1) a cyanated naphthoylbenzimidazole compound of formula (II)

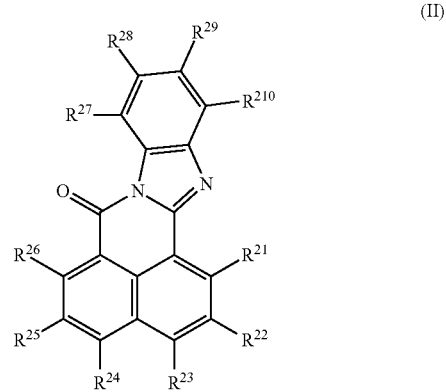

(II)

wherein $R^{21}$, $R^{22}$, $R^{23}$, $R^{24}$, $R^{25}$, $R^{26}$, $R^{27}$, $R^{28}$, $R^{29}$ and $R^{210}$ are each independently hydrogen, cyano or aryl which is unsubstituted or has one or more identical or different substituents $R^{24r}$,
where each $R^{24r}$ is independently selected from cyano, hydroxyl, mercapto, halogen, $C_1$-$C_{20}$-alkoxy, $C_1$-$C_{20}$-alkylthio, nitro, —$NR^{24r2}R^{24r3}$, —$NR^{24r2}COR^{24r3}$, —$CONR^{24r2}R^{24r3}$, —$SO_2NR^{24r2}R^{24r3}$, —$COOR^{24r2}$, —$SO_3R^{24r2}$, $C_1$-$C_{30}$-alkyl, $C_2$-$C_{30}$-alkenyl, $C_2$-$C_{30}$-alkynyl, where the three latter radicals are unsubstituted or bear one or more $R^{2a}$ groups, $C_3$-$C_8$-cycloalkyl, 3- to 8-membered heterocyclyl, where the two latter radicals are unsubstituted or bear one or more $R^{2b}$ groups, aryl, U-aryl, heteroaryl and U-heteroaryl, where the four latter radicals are unsubstituted or bear one or more $R^{2b}$ groups,
where each $R^{2a}$ is independently selected from cyano, hydroxyl, oxo, mercapto, halogen, $C_1$-$C_{20}$-alkoxy, $C_1$-$C_{20}$-alkylthio, nitro, —$NR^{24r2}R^{Ar3}$, —$NR^{24r2}COR^{24r3}$, —$CONR^{24r2}R^{Ar3}$, —$SO_2NR^{24r2}R^{Ar3}$, —$COOR^{24r2}$, —$SO_3R^{24r2}$, $C_3$-$C_8$-cycloalkyl, 3- to 8-membered heterocyclyl, aryl and heteroaryl, where the cycloalkyl, heterocyclyl, aryl and heteroaryl radicals are unsubstituted or bear one or more $R^{2b}$ groups;
each $R^{2b}$ is independently selected from cyano, hydroxyl, oxo, mercapto, halogen, $C_1$-$C_{20}$-alkoxy, $C_1$-$C_{20}$-alkylthio, nitro, —$NR^{24r2}R^{24r3}$, —$NR^{24r2}COR^{24r3}$, —$CONR^{24r2}R^{24r3}$, —$SO_2NR^{24r2}R^{24r3}$, —$COOR^{24r2}$, —$SO_3R^{24r2}$, $C_1$-$C_{18}$-alkyl, $C_2$-$C_{18}$-alkenyl, $C_2$-$C_{18}$-alkynyl, $C_3$-$C_8$-cycloalkyl, 3- to 8-membered heterocyclyl, aryl and heteroaryl, where the four latter radicals are unsubstituted or bear one or more $R^{2b1}$ groups,
each $R^{2b1}$ is independently selected from cyano, hydroxyl, mercapto, oxo, nitro, halogen, —$NR^{24r2}R^{24r3}$, —$NR^{24r2}COR^{24r3}$, —$CONR^{24r2}R^{24r3}$, —$SO_2NR^{24r2}R^{24r3}$, —$COOR^{24r2}$, —$SO_3R^{24r2}$, —$SO_3R^{24r2}$, $C_1$-$C_{18}$-alkyl, $C_2$-$C_{18}$-alkenyl, $C_2$-$C_{18}$-alkynyl, $C_1$-$C_{12}$-alkoxy, and $C_1$-$C_{12}$-alkylthio;
U is an —O—, —S—, —$NR^{24r1}$-, —CO—, —SO— or —$SO_2$— moiety; and $R^{24r1}$, $R^{24r2}$, $R^{24r3}$ are each independently hydrogen, $C_1$-$C_{18}$-alkyl, 3- to 8-membered cycloalkyl, 3- to 8-membered heterocyclyl, aryl or heteroaryl, where alkyl is unsubstituted or bears one or more $R^{2a}$ groups, where 3- to 8-membered cycloalkyl, 3- to 8-membered heterocyclyl, aryl and heteroaryl are unsubstituted or bear one or more $R^{2b}$ groups;
with the proviso that the compound of formula (II) comprises at least one cyano group,
and mixtures thereof;
(B2) a cyanated perylene compound of formula (III)

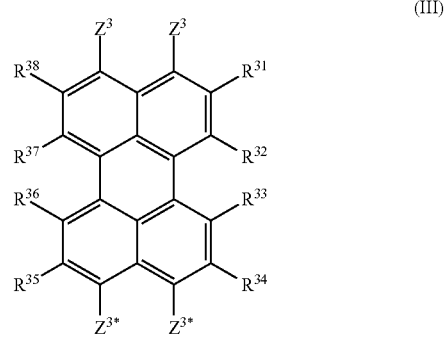

(III)

in which one of the $Z^3$ substituents is cyano and the other $Z^3$ substituent is $CO_2R^{39}$, $CONR^{310}R^{311}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where $C_1$-$C_{18}$-alkyl, $C_2$-$C_{18}$-alkenyl, $C_2$-$C_{18}$-alkynyl are unsubstituted or bear one or more identical or different $Z^{3a}$ substituents, $C_3$-$C_{12}$-cycloalkyl is unsubstituted or bears one or more identical or different $Z^{3b}$ substituents, and $C_6$-$C_{14}$-aryl is unsubstituted or bears one or more identical or different $Z^{3Ar}$ substituents;
one of the $Z^{3*}$ substituents is cyano and the other $Z^{3*}$ substituent is $CO_2R^{39}$, $CONR^{310}R^{311}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where $C_1$-$C_{18}$-alkyl, $C_2$-$C_{18}$-alkenyl, $C_2$-$C_{18}$-alkynyl are unsubstituted or bear one or more identical or different $Z^{3a}$ substituents, $C_3$-$C_{12}$-cycloalkyl is unsubstituted or bears one or more identical or different $Z^{3b}$ substituents, and $C_6$-$C_{14}$-aryl is unsubstituted or bears one or more identical or different $Z^{3Ar}$ substituents; and
$R^{31}$, $R^{32}$, $R^{33}$, $R^{34}$, $R^{35}$, $R^{36}$, $R^{37}$ and $R^{38}$ are each independently selected from hydrogen, cyano, bromine and chlorine,
with the proviso that 1, 2, 3, 4, 5, 6, 7 or 8 of the $R^{31}$, $R^{32}$, $R^{33}$, $R^{34}$, $R^{35}$, $R^{36}$, $R^{37}$ or $R^{38}$ substituents are cyano;
where $R^{39}$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where $C_1$-$C_{10}$-alkyl, $C_2$-$C_{10}$-alkenyl, $C_2$-$C_{10}$-alkynyl are unsubstituted or bear one or more identical or different $R^{3a}$ substituents, $C_3$-$C_{12}$-cycloalkyl is unsubstituted or bears one or more identical or different $R^{3b}$ substituents and $C_6$-$C_{14}$-aryl is unsubstituted or bears one or more identical or different $R^{3Ar}$ substituents;
$R^{310}$ and $R^{311}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where $C_1$-$C_{10}$-alkyl, $C_2$-$C_{10}$-alkenyl, $C_2$-$C_{10}$-alkynyl are unsubstituted or bear one or more identical or different $R^{3a}$ substituents, $C_3$-$C_{12}$-cycloalkyl is unsubstituted or bears one or more identical or different $R^{3b}$ substituents and $C_6$-$C_{14}$-aryl is unsubstituted or bears one or more identical or different $R^{3Ar}$ substituents;

each $Z^{3a}$ is independently halogen, hydroxyl, $NR^{310a}R^{311a}$, $C_1$-$C_{10}$-alkoxy, $C_1$-$C_{10}$-haloalkoxy, $C_1$-$C_{10}$-alkylthio, $C_3$-$C_{12}$-cycloalkyl, $C_6$-$C_{14}$-aryl, $C(=O)R^{39a}$; $C(=O)OR^{39a}$ or $C(O)NR^{310a}R^{311a}$, where $C_3$-$C_{12}$-cycloalkyl is unsubstituted or bears one or more identical or different $R^{3b}$ substituents and $C_6$-$C_{14}$-aryl is unsubstituted or bears one or more identical or different $R^{3Ar}$ substituents;

each $Z^{3b}$ and each $Z^{3Ar}$ is independently halogen, hydroxyl, $NR^{310a}R^{311a}$, $C_1$-$C_{10}$-alkyl, $C_1$-$C_{10}$-alkoxy, $C_1$-$C_{10}$-haloalkoxy, $C_1$-$C_{10}$-alkylthio, $C(=O)R^{39a}$; $C(=O)OR^{39a}$ or $C(O)NR^{310a}R^{311a}$;

each $R^{3a}$ is independently halogen, hydroxyl, $C_1$-$C_{10}$-alkoxy, $C_3$-$C_{12}$-cycloalkyl or $C_6$-$C_{14}$-aryl;

each $R^{3b}$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$-alkylthio, $C_2$-$C_{10}$-alkenyl, $C_2$-$C_{10}$-alkynyl, $C_3$-$C_{12}$-cycloalkyl or $C_6$-$C_{14}$-aryl;

each $R^{3Ar}$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$-alkylthio, $C_2$-$C_{10}$-alkenyl, $C_2$-$C_{10}$-alkynyl, $C_3$-$C_{12}$-cycloalkyl or $C_6$-$C_{14}$-aryl;

$R^{39a}$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl; and $R^{310a}$, $R^{311a}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, and mixtures thereof;

(B3) a cyanated compound of formula (IV)

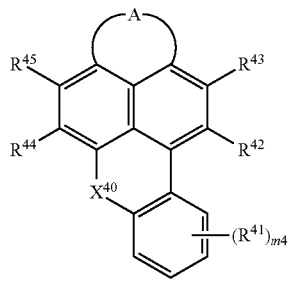

(IV)

wherein m4 is 0, 1, 2, 3 or 4;

each $R^{41}$ independently from each other is selected from bromine, chlorine, cyano, —$NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, and $C_6$-$C_{24}$-aryl-$C_1$-$C_{10}$-alkylene, where the rings of cycloalkyl, heterocycloalkyl, heteroaryl, aryl, aryloxy in the six last-mentioned radicals are unsubstituted or substituted with 1, 2, 3, 4 or 5 identical or different radicals $R^{41a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from O, S and $NR^{4c}$;

at least one of the radicals $R^{42}$, $R^{43}$, $R^{44}$ and $R^{45}$ is CN, and the remaining radicals, independently from each other, are selected from hydrogen, chlorine and bromine;

$X^{40}$ is O, S, SO or $SO_2$; and

A is a diradical selected from diradicals of the general formulae (A.1), (A.2), (A.3), and (A.4)

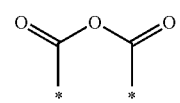

(A.1)

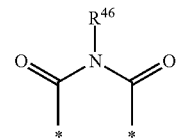

(A.2)

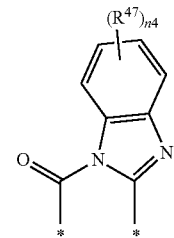

(A.3)

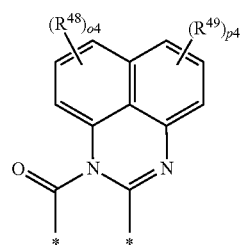

(A.4)

wherein * in each case denotes the point of attachments to the remainder of the molecule;

n4 is 0, 1, 2, 3 or 4;

o4 is 0, 1, 2 or 3;

p4 is 0, 1, 2 or 3;

R46 is hydrogen, $C_1$-$C_{24}$-alkyl, $C_1$-$C_{24}$-haloalkyl, $C_3$-$C_{24}$-cycloalkyl, $C_6$-$C_{24}$-aryl or $C_6$-$C_{24}$-aryl-$C_1$-$C_{10}$-alkylene, where the rings of cycloalkyl, aryl, and aryl-alkylene in the three last-mentioned radicals are unsubstituted or substituted with 1, 2, 3, 4 or 5 identical or different radicals $R^{46a}$, and where $C_1$-$C_{24}$-alkyl, $C_1$-$C_{24}$-haloalkyl and the alkylene moiety of $C_6$-$C_{24}$-aryl-$C_1$-$C_{10}$-alkylene may be interrupted by one or more heteroatoms or heteroatomic groups selected from O, S and $NR^{4c}$;

each $R^{47}$ independently from each other is selected from bromine, chlorine, cyano, —$NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, and $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{47a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;

each $R^{48}$ independently from each other is selected from bromine, chlorine, cyano, $NR^{4a}R^{4b}$, $C_1$-$C_{24}$-alkyl, C$_1$-C$_{24}$-haloalkyl, C$_1$-C$_{24}$-alkoxy, C$_1$-C$_{24}$-haloalkoxy, C$_3$-C$_{24}$-cycloalkyl, heterocycloalkyl, heteroaryl, C$_6$-C$_{24}$-aryl, C$_6$-C$_{24}$-aryloxy, and C$_6$-C$_{24}$-aryl-C$_1$-C$_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals R$^{48a}$ and where C$_1$-C$_{24}$-alkyl, C$_1$-C$_{24}$-haloalkyl, C$_1$-C$_{24}$-alkoxy, C$_1$-C$_{24}$-haloalkoxy, and the alkylene moiety of C$_6$-C$_{24}$-aryl-C$_1$-C$_{10}$-alkylene may be interrupted by one or more groups selected from O, S and NR$^{4c}$;

each R$^{49}$ independently from each other is selected from bromine, chlorine, cyano, NR$^{4a}$R$^{4b}$, C$_1$-C$_{24}$-alkyl, C$_1$-C$_{24}$-haloalkyl, C$_1$-C$_{24}$-alkoxy, C$_1$-C$_{24}$-haloalkoxy, C$_3$-C$_{24}$-cycloalkyl, heterocycloalkyl, heteroaryl, C$_6$-C$_{24}$-aryl, C$_6$-C$_{24}$-aryloxy, and C$_6$-C$_{24}$-aryl-C$_1$-C$_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals R$^{49a}$ and where C$_1$-C$_{24}$-alkyl, C$_1$-C$_{24}$-haloalkyl, C$_1$-C$_{24}$-alkoxy, C$_1$-C$_{24}$-haloalkoxy, and the alkylene moiety of C$_6$-C$_{24}$-aryl-C$_1$-C$_{10}$-alkylene may be interrupted by one or more groups selected from O, S and NR$^{4c}$;

R$^{41a}$, R$^{46a}$, R$^{47a}$, R$^{48a}$, R$^{49a}$ are independently of one another selected from C$_1$-C$_{24}$-alkyl, C$_1$-C$_{24}$-fluoroalkyl, C$_1$-C$_{24}$-alkoxy, fluorine, chlorine and bromine; and R$^{4a}$, R$^{4b}$, R$^{4c}$ are independently of one another are selected from hydrogen, C$_1$-C$_{20}$-alkyl, C$_3$-C$_{24}$-cycloalkyl, heterocycloalkyl, heteroaryl and C$_6$-C$_{24}$-aryl;

and mixtures thereof;

(B4) a benz(othi)oxanthene compound of formula (V)

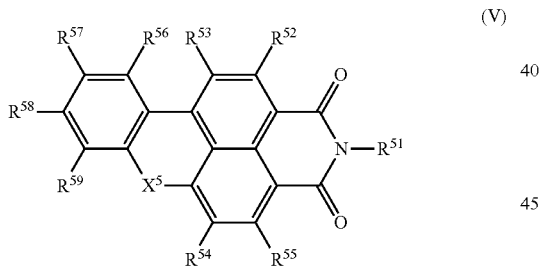

(V)

wherein X$^5$ is oxygen or sulfur;

R$^{51}$ is phenyl which is unsubstituted or carries 1, 2, 3, 4, or 5 substituents selected from halogen, R$^{511}$, OR$^{552}$, NHR$^{552}$ and NR$^{552}$R$^{557}$; and R$^{52}$, R$^{53}$, R$^{54}$, R$^{55}$, R$^{56}$, R$^{57}$, R$^{58}$ and R$^{59}$ are independently of each other selected from hydrogen, halogen, R$^{553}$, OR$^{553}$, NHR$^{553}$ and NR$^{553}$R$^{554}$, wherein R$^{511}$ is selected from C$_1$-C$_{24}$-alkyl, C$_6$-C$_{24}$-aryl and heteroaryl;

R$^{552}$ and R$^{557}$ are independently of each other selected from C$_1$-C$_{18}$-alkyl, C$_6$-C$_{24}$-aryl and heteroaryl; and R$^{553}$ and R$^{554}$ are independently of each other selected from C$_1$-C$_{18}$-alkyl, C$_6$-C$_{24}$-aryl and heteroaryl;

and mixtures thereof;

(B5) a benzimidazoxanthenisoquinoline compound of formulae (VIA) or (VIB)

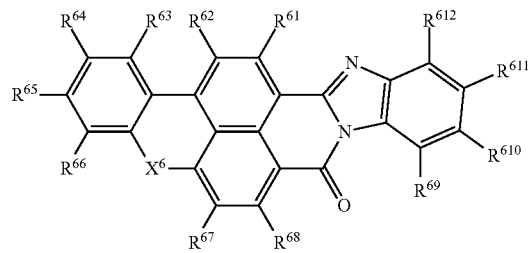

(VIA)

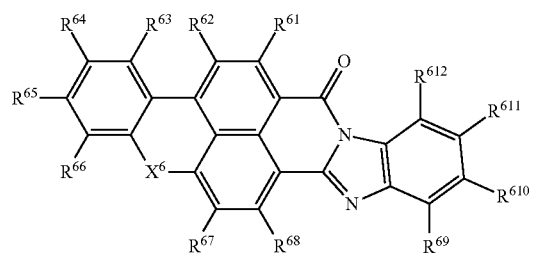

(VIB)

wherein

X$^6$ is oxygen or sulfur; and

R$^{61}$, R$^{62}$, R$^{63}$, R$^{64}$, R$^{65}$, R$^{66}$, R$^{67}$, R$^{68}$, R$^{69}$, R$^{610}$, R$^{611}$ and R$^{612}$ are independently of each other selected from hydrogen, halogen, R$^{661}$, OR$^{661}$, NHR$^{661}$ and NR$^{661}$R$^{662}$, wherein each R$^{661}$ is selected from C$_1$-C$_{18}$-alkyl, C$_6$-C$_{24}$-aryl and heteroaryl; and each R$^{662}$ is selected from C$_1$-C$_{18}$-alkyl, C$_6$-C$_{24}$-aryl and heteroaryl;

and mixtures thereof;

(B6) a fluorescent compound comprising at least one structural unit of formula (VII)

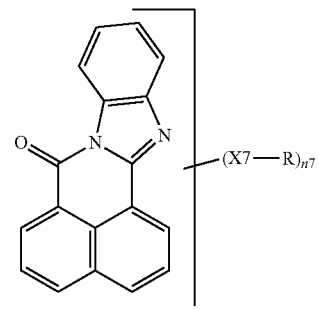

(VII)

where one or more CH groups of the six-membered ring of the benzimidazole structure shown may be replaced by nitrogen and where the symbols are each defined as follows:

n7 is a number from 0 to (10-p7) for each structural unit of formula (VII); where p7 is the number of CH units which have been replaced by nitrogen in the six-membered ring of the benzimidazole structure shown X7 is a chemical bond, O, S, SO, SO$_2$, or NR$^{71}$; and
R is an aliphatic radical, cycloaliphatic radical, aryl, heteroaryl, each of which may bear substituents, an aromatic or heteroaromatic ring or ring system, each of which is fused to other aromatic rings of the structural unit of formula (VII),
is F, Cl, Br, CN, H when X7 is not a chemical bond;
where two R radicals may be joined to give one cyclic radical and
where X7 and R, when n7>one, may be the same or different;
R$^{71}$ is each independently hydrogen, C$_1$-C$_{18}$-alkyl or cycloalkyl, the carbon chain of which may comprise one or more —O—, —S—, —CO—, —SO— and/or —SO$_2$-moieties and which may be mono- or polysubstituted; aryl or heteroaryl which may be mono- or polysubstituted;
and mixtures thereof;
(B7) a perylene compound of formulae (VIII) or (IX)

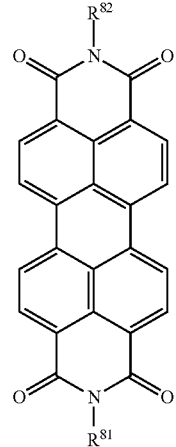

(VIII)

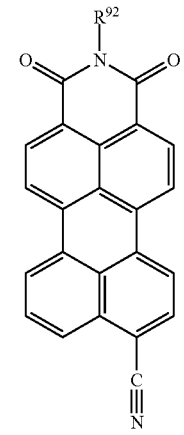

(IX)

where R$^{81}$, R$^{82}$ are each independently C$_1$-C$_{30}$-alkyl, C$_2$-C$_{30}$-alkyl which is interrupted by one or more oxygen, C$_3$-C$_8$-cycloalkyl, C$_6$-C$_{10}$-aryl, heteroaryl, C$_6$-C$_{10}$-aryl-C$_1$-C$_{10}$-alkylene, where the aromatic ring in the three latter radicals is unsubstituted or mono- or polysubstituted by C$_1$-C$_{10}$-alkyl; and R$^{92}$ is C$_1$-C$_{30}$-alkyl, C$_3$-C$_8$-cycloalkyl, or aryl, heteroaryl, aryl-C$_1$-C$_{10}$-alkylene, where the aromatic ring in the three latter radicals is unsubstituted or mono- or polysubstituted by C$_1$-C$_{10}$-alkyl;

(B8) a naphthalene monoimide compound of formula (X)

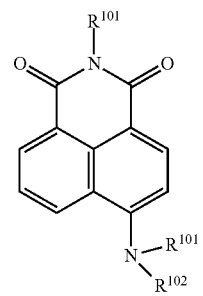

(X)

wherein each R$^{101}$ independently of each other is hydrogen, C$_1$-C$_{30}$-alkyl, C$_2$-C$_{30}$-alkyl which is interrupted by one or more oxygen, C$_3$-C$_8$-cycloalkyl, or C$_6$-C$_{10}$-aryl, heteroaryl, C$_6$-C$_{10}$-aryl-C$_1$-C$_{10}$-alkylene, where the aromatic ring in the three latter radicals is unsubstituted or mono- or polysubstituted by C$_1$-C$_{10}$-alkyl; and R$^{102}$ is hydrogen, C$_1$-C$_{30}$-alkyl, C$_2$-C$_{30}$-alkyl which is interrupted by one or more oxygen, C$_3$-C$_8$-cycloalkyl, C$_6$-C$_{10}$-aryl, heteroaryl, C$_6$-C$_{10}$-aryl-C$_1$-C$_{10}$-alkylene, where the aromatic ring in the three latter radicals is unsubstituted or mono- or polysubstituted by C$_1$-C$_{10}$-alkyl;

(B9) 7-(diethylamino)-3-(5-methylbenzo[d]oxazol-2-yl)-2H-chromen-2-one;

(B10) a perylene compound of formulae (XIA) or (XIB)

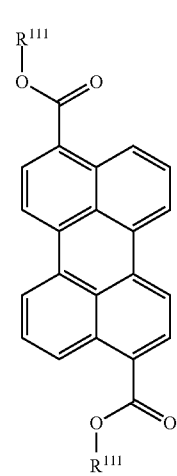

(XIA)

(XIB)

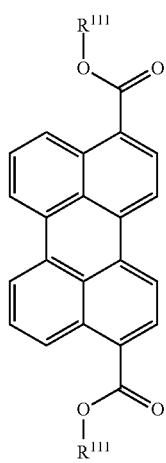

wherein each $R^{111}$ independently of each other is $C_1$-$C_{18}$ alkyl, $C_4$-$C_8$ cycloalkyl, which may be mono- or polysubstituted by halogen or by linear or branched $C_1$-$C_{18}$ alkyl, or phenyl or naphthyl which may be mono- or polysubstituted by halogen or by linear or branched $C_1$-$C_{18}$ alkyl;

and mixtures thereof;

(B11) a cyanated perylene compound of formulae (XIIA) or (XIIB)

(XIIA)

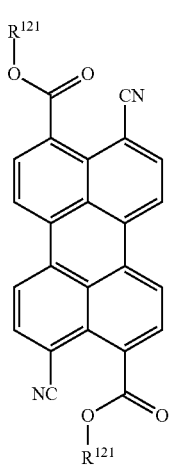

(XIIB)

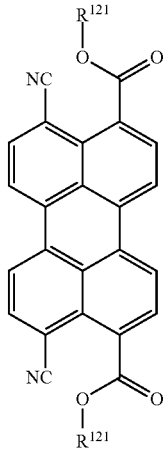

wherein each $R^{121}$ independently of each other is $C_1$-$C_{18}$ alkyl, $C_4$-$C_8$ cycloalkyl, which may be mono- or polysubstituted by halogen or by linear or branched $C_1$-$C_{18}$ alkyl, or phenyl or naphthyl which may be mono- or polysubstituted by halogen or by linear or branched $C_1$-$C_{18}$ alkyl;

and mixtures thereof;

(B12) a naphthoylbenzimidazole compound of formula (XIII)

(XIII)

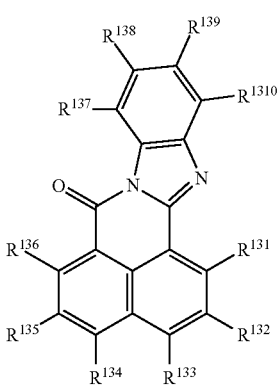

wherein at least one of the radicals $R^{131}$, $R^{132}$, $R^{133}$, $R^{134}$, $R^{135}$, $R^{136}$, $R^{137}$, $R^{138}$, $R^{139}$ and $R^{1310}$ independently of each other is aryl which carries one, two or three cyano groups and 0, 1, 2, 3 or 4 substituents $R^{Ar13}$ and the remaining radicals $R^{131}$, $R^{132}$, $R^{133}$, $R^{134}$, $R^{135}$, $R^{136}$, $R^{137}$, $R^{138}$, $R^{139}$ and $R^{1310}$ independently of each other are selected from hydrogen and aryl which is unsubstituted or carries 1, 2, 3, 4 or 5 substituents $R^{Ar13}$, where $R^{Ar13}$ independently of each other and independently of each occurrence is selected from halogen, $C_1$-$C_{30}$-alkyl, $C_2$-$C_{30}$-alkenyl, $C_2$-$C_{30}$-alkynyl, where the three latter radicals are unsubstituted or carry one or more $R^{13a}$ groups, $C_3$-$C_8$-cycloalkyl, 3- to 8-membered heterocyclyl, where the two latter radicals are unsubstituted or carry one or more $R^{13b}$ groups, aryl and heteroaryl, where the two latter radicals are unsubstituted or carry one or more $R^{13c}$ groups, where $R^{13a}$ independently of each other and independently of each occurrence is selected from cyano, halogen, $C_3$-$C_8$-cycloalkyl, 3- to 8-membered heterocyclyl, aryl and heteroaryl, where $C_3$-$C_8$-cycloalkyl, 3- to 8-membered heterocyclyl are unsubstituted or bear one or more $R^{13b1}$ groups, and where aryl and heteroaryl are unsubstituted or bear one or more $R^{13c1}$ groups;

$R^{13b}$ independently of each other and independently of each occurrence is selected from cyano, halogen, $C_1$-$C_{18}$-alkyl, $C_3$-$C_8$-cycloalkyl, 3- to 8-membered heterocyclyl, aryl and heteroaryl, where $C_3$-$C_8$-cycloalkyl, 3- to 8-membered heterocyclyl are unsubstituted or bear one or more $R^{13b1}$ groups, and where aryl and heteroaryl are unsubstituted or bear one or more $R^{13c1}$ groups;

$R^{13c}$ independently of each other and independently of each occurrence is selected from cyano, halogen, $C_1$-$C_{18}$-alkyl, $C_3$-$C_8$-cycloalkyl, 3- to 8-membered heterocyclyl, aryl and heteroaryl, where $C_3$-$C_8$-cycloalkyl, 3- to 8-membered heterocyclyl are unsubstituted or bear one or more $R^{13b1}$ groups, and where aryl and heteroaryl are unsubstituted or bear one or more $R^{13c1}$ groups;

$R^{13b1}$ independently of each other and independently of each occurrence is selected from halogen, $C_1$-$C_{18}$-alkyl and $C_1$-$C_{18}$-haloalkyl, and $R^{13c1}$ independently of each other and independently of each occurrence is selected from halogen, $C_1$-$C_{18}$-alkyl and $C_1$-$C_{18}$-haloalkyl;

and mixtures thereof;

(B13) a perylene compound of formula (XIV)

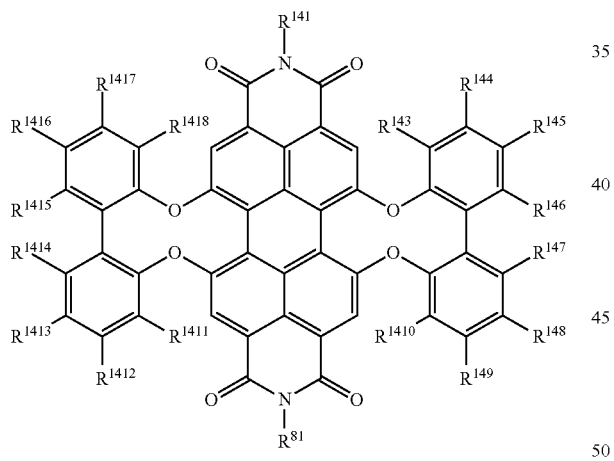

(XIV)

wherein $R^{141}$ and $R^{142}$, independently of each other, are selected from hydrogen, in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkyloxy, $C_6$-$C_{24}$-aryl and $C_6$-$C_{24}$-aryloxy;

$R^{143}$, $R^{144}$, $R^{145}$, $R^{146}$, $R^{147}$, $R^{148}$, $R^{149}$, $R^{1410}$, $R^{1411}$, $R^{1412}$, $R^{1413}$, $R^{1414}$, $R^{1415}$, $R^{1416}$, $R^{1417}$, and $R^{1418}$ independently of each other, are selected from hydrogen, halogen, cyano, hydroxyl, mercapto, nitro, —$NE^{141}E^{142}$, —$NR^{Ar141}COR^{Ar142}$, —$CONR^{Ar141}R^{Ar142}$, —$SO_2NR^{A141}R^{A142}$, —COO$R^{Ar141}$, —$SO_3R^{Ar142}$, in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkoxy, $C_6$-$C_{24}$-aryl, $C_6$-$C_{24}$-aryloxy and $C_6$-$C_{24}$-arylthio, where $R^{143}$ and $R^{144}$, $R^{144}$ and $R^{145}$, $R^{145}$ and $R^{146}$, $R^{146}$ and $R^{147}$, $R^{147}$ and $R^{148}$, $R^{148}$ and $R^{149}$, $R^{149}$ and $R^{1410}$, $R^{1411}$ and $R^{1412}$, $R^{1412}$ and $R^{1413}$, $R^{1413}$ and $R^{1414}$, $R^{1414}$ and $R^{1415}$, $R^{1415}$ and $R^{1416}$, $R^{1416}$ and $R^{1417}$ and/or $R^{1417}$ and $R^{1418}$ together with the carbon atoms of the biphenylyl moiety to which they are bonded, may also form a further fused aromatic or non-aromatic ring system wherein the fused ring system is unsubstituted or substituted;

where $E^{141}$ and $E^{142}$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl; and $R^{Ar141}$ and $R^{Ar142}$, each independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C6$-$C_{20}$-aryl or unsubstituted or substituted heteroaryl;

and mixtures thereof; and (B14) a perylene bisimide compound of formula (XV) different from compound (I)

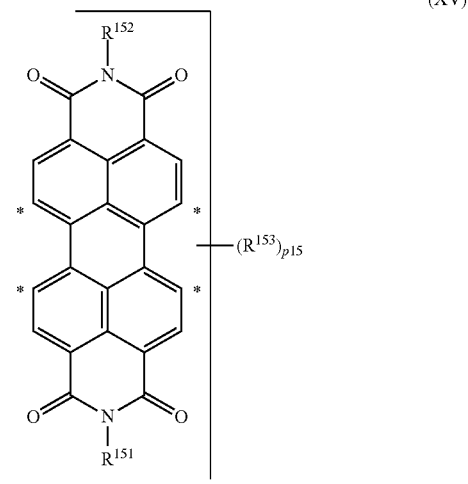

(XV)

wherein p15 is 1, 2, 3 or 4;

$R^{151}$ and $R^{152}$ independently of each other are $C_1$-$C_{10}$-alkyl, which is unsubstituted or substituted by $C_6$-$C_{10}$-aryl which in turn is unsubstituted or substituted by 1, 2 or 3 $C_1$-$C_{10}$-alkyl, $C_2$-$C_{20}$-alkyl, which is interrupted by one or more oxygen, $C_3$-$C_8$-cycloalkyl, which is unsubstituted or substituted by 1, 2 or 3 $C_1$-$C_{10}$-alkyl, or $C_6$-$C_{10}$-aryl which is unsubstituted or substituted by 1, 2 or 3 $C_1$-$C_{10}$-alkyl; and each $R^{153}$ independently of each other is fluorine, chlorine, $C_1$-$C_{16}$-alkyl, $C_2$-$C_{16}$-alkyl interrupted by one or more oxygen, $C_1$-$C_{16}$-alkoxy, $C_6$-$C_{10}$-aryloxy which is unsubstituted or mono- or polysubstituted by fluorine, chlorine, $C_1$-$C_{16}$-alkyl, $C_2$-$C_{16}$-alkyl interrupted by one or more oxygen, $C_1$-$C_{16}$-alkoxy or $C_6$-$C_{10}$-aryl, which is unsubstituted or substituted by 1, 2 or 3 radicals selected from $C_1$-$C_6$-alkyl, $C_1$-$C_6$-alkoxy-$C_1$-$C_6$-alkyl and $C_1$-$C_6$-alkoxy, where the $R^{133}$ radicals are at the positions indicated by *; and mixtures thereof.

8. The color converter according to claim 5, comprising as further fluorescent material at least one inorganic fluorescent material selected from garnets, silicates, sulfides, nitrides and oxynitrides.

9. The color converter according to claim 5, comprising at least one quantum dot from a crystalline semiconductor material.

10. A process for converting light generated by a blue LED with a center wavelength of emission between 400 nm and 480 nm to provide white light or for converting light generated by a cool white LED having a correlated color temperature between 4 000 K and 20 000 K to provide white light having a lower correlated color temperature, the process comprising exposing the color converter of claim 5 to light.

11. A display, comprising the color converter of claim 5.

12. A lighting device comprising
(i) at least one LED selected from a blue LED with a center wavelength of emission from 400 nm to 480 nm and a cool white LED having a correlated color temperature between 3 000 K and 20 000 K; and
(ii) at least one color converter as defined in claim 5,
wherein the at least one color converter is in a remote arrangement from the at least one LED.

13. A device capable of producing electric power upon illumination, the device comprising a photovoltaic cell and the color converter as defined in claim 5, where at least a part of the light not absorbed by the photovoltaic cell is absorbed by the color converter.

14. A process for converting light emitted from a blue LED with a center wavelength of emission between 400 nm and 480 nm into light of a second, longer wavelength or for converting light emitted from a cool-white LED having a correlated color temperature between 3 000 K and 20 000 K to provide white light having a lower correlated color temperature, for coloring coatings, printing inks and plastics, producing aqueous polymer dispersions which absorb and/or emit electromagnetic radiation, for data storage, for data transmission, for optical labels, for security labels in documents and for brand protection or as a fluorescent label for biomolecules, the process comprising exposing a perylene bisimide compound of formula (I) as defined in claim 1 to light.

15. A security ink for security printing, comprising the perylene bisimide compound of formula (I) as defined in claim 1.

16. A transmitter for transmitting data and for emitting electromagnetic radiation in the visible spectral range, said transmitter comprising:
a radiation source for generating and emitting first electromagnetic radiation and
a modulator being adapted to modulate the first electromagnetic radiation depending on the data to be transmitted for generating modulated first electromagnetic radiation,
wherein the transmitter further comprises
a color converter as defined in claim 5 for converting at least a part of the modulated first electromagnetic radiation into modulated second electromagnetic radiation, said modulated second electromagnetic radiation being different from the modulated first electromagnetic radiation.

17. A printing ink formulation for security printing, comprising at least one compound of formula (I) as defined in claim 1.

18. The printing ink formulation according to claim 17, further comprising
a polymeric binder;
optionally an organic solvent;
optionally at least one colorant; and
optionally at least one further additive.

* * * * *